United States Patent
Kassman

(10) Patent No.: US 6,569,083 B1
(45) Date of Patent: *May 27, 2003

(54) MALE, HERMAPHRODITIC, AND FEMALE CONDOMS EXERTING LATERAL PRESSURE ON THE PENIS AND THE VAGINA

(76) Inventor: Leon B. Kassman, 242 E. 24th St., New York, NY (US) 10010

( * ) Notice: Subject to any disclaimer, the term of this patent is extended or adjusted under 35 U.S.C. 154(b) by 0 days.

This patent is subject to a terminal disclaimer.

(21) Appl. No.: 09/274,522

(22) Filed: Mar. 23, 1999

Related U.S. Application Data

(63) Continuation-in-part of application No. 08/725,562, filed on Oct. 3, 1996, now Pat. No. 5,885,205.

(51) Int. Cl.7 .................................................. A61F 5/00
(52) U.S. Cl. ...................... 600/38; 128/842; 128/844; 128/918
(58) Field of Search ................................ 128/842, 844, 128/918; 604/347–353; 600/38

(56) References Cited

U.S. PATENT DOCUMENTS

| | | | | |
|---|---|---|---|---|
| 1,225,341 A | * | 5/1917 | Lederer | 600/38 |
| 3,495,589 A | * | 2/1970 | Clement | 600/38 |
| 3,536,066 A |   | 10/1970 | Ludwig | 128/132 |
| 4,004,591 A |   | 1/1977 | Freimark | 128/294 |
| 4,378,008 A | * | 3/1983 | Osbon | 600/38 |
| 4,523,584 A | * | 6/1985 | Yachia | 600/38 |
| 4,576,156 A |   | 3/1986 | Dyck et al. | 128/132 R |
| 4,664,104 A | * | 5/1987 | Jaicks | 604/353 |
| 4,671,262 A | * | 6/1987 | West | 600/39 |
| 4,735,621 A |   | 4/1988 | Hessel | 604/349 |
| 4,808,174 A |   | 2/1989 | Sorkin | 128/644 |
| 4,817,593 A |   | 4/1989 | Taller et al. | 128/844 |
| 4,829,991 A | * | 5/1989 | Boeck | 600/38 |
| 4,840,624 A |   | 6/1989 | Lee | 604/349 |
| 4,855,169 A |   | 8/1989 | McGlothlin | 428/35.2 |
| 4,867,176 A |   | 9/1989 | Lash | 128/830 |
| 4,898,184 A |   | 2/1990 | Skurkovich | 128/844 |
| 4,993,431 A |   | 2/1991 | Reddy | 128/830 |
| 4,993,433 A |   | 2/1991 | Reddy | 128/842 |
| 5,069,228 A |   | 12/1991 | Sorkin | 128/844 |
| 5,109,871 A | * | 5/1992 | Thornton | 128/844 |
| 5,112,900 A |   | 5/1992 | Buddenhagen | 524/484 |
| 5,325,871 A |   | 7/1994 | Reddy | 128/830 |
| 5,370,131 A | * | 12/1994 | Hess | 128/844 |
| 5,377,692 A | * | 1/1995 | Pfeil | 128/844 |
| 5,407,715 A |   | 4/1995 | Buddenhagen | 428/35.7 |
| 5,437,286 A |   | 8/1995 | Stratton | 128/844 |

(List continued on next page.)

OTHER PUBLICATIONS

"Female Condom Provides Option", Reuters, Medical News Service on Physicians' Online, Jul. 16, 1997.

"Careers in Medicine Cut Short by Growing Allergy to Latex", Jennifer Steinhauer, *New York Times*, Mar. 7, 1999.

*Primary Examiner*—Michael A. Brown
(74) *Attorney, Agent, or Firm*—Abelman, Frayne & Schwab

(57) ABSTRACT

Male, hermaphroditic, and female condoms that exert lateral pressure on the penis and the vagina of a man and a woman respectively are disclosed. The lateral pressure is exerted by the geometry of the condoms themselves upon application or is exerted by means for exerting such lateral pressure located or applied on the condoms which means are normally activated by the user after the condoms are applied. User activated lateral pressure is controllable by the user within safe limits or, once activated by the user, is designed to be within safe limits. The lateral pressure retains the condoms securely in position to act as contraceptive and prophylactic barriers between the male and female genital areas, while increasing stimulation during intercourse.

106 Claims, 23 Drawing Sheets

U.S. PATENT DOCUMENTS

| | | | |
|---|---|---|---|
| 5,458,114 A | * 10/1995 | Herr | 128/844 |
| 5,469,863 A | * 11/1995 | Shah | 128/844 |
| 5,471,998 A | 12/1995 | Kuyumciyan | 128/842 |
| 5,515,862 A | 5/1996 | Artsi et al. | 128/830 |
| 5,549,120 A | 8/1996 | Persson et al. | 128/842 |
| 5,549,424 A | * 8/1996 | Shlenker | 128/844 |
| 5,549,924 A | 8/1996 | Shlenker | 427/2.3 |
| 5,551,612 A | 9/1996 | Hochfeld | 224/219 |
| 5,596,997 A | 1/1997 | Abadi | 128/844 |
| 5,598,852 A | 2/1997 | Spery | 128/844 |
| 5,601,092 A | 2/1997 | Miller et al. | 128/844 |
| 5,603,335 A | 2/1997 | McClenahan | 128/844 |
| 5,623,945 A | 4/1997 | Shecterle | 128/842 |
| 5,623,946 A | 4/1997 | Hessel | 128/844 |
| 5,623,947 A | 4/1997 | Lawlor | 128/844 |
| 5,638,949 A | 6/1997 | Jones | 206/69 |
| 5,651,374 A | 7/1997 | Wester | 128/844 |
| 5,662,214 A | 9/1997 | Wood | 206/69 |
| 5,666,972 A | 9/1997 | Gifford | 128/842 |
| 5,713,830 A | * 2/1998 | Tucker | 600/38 |
| 5,715,839 A | * 2/1998 | Strauss | 128/844 |
| 5,803,085 A | * 9/1998 | Asinovsky | 128/844 |

* cited by examiner

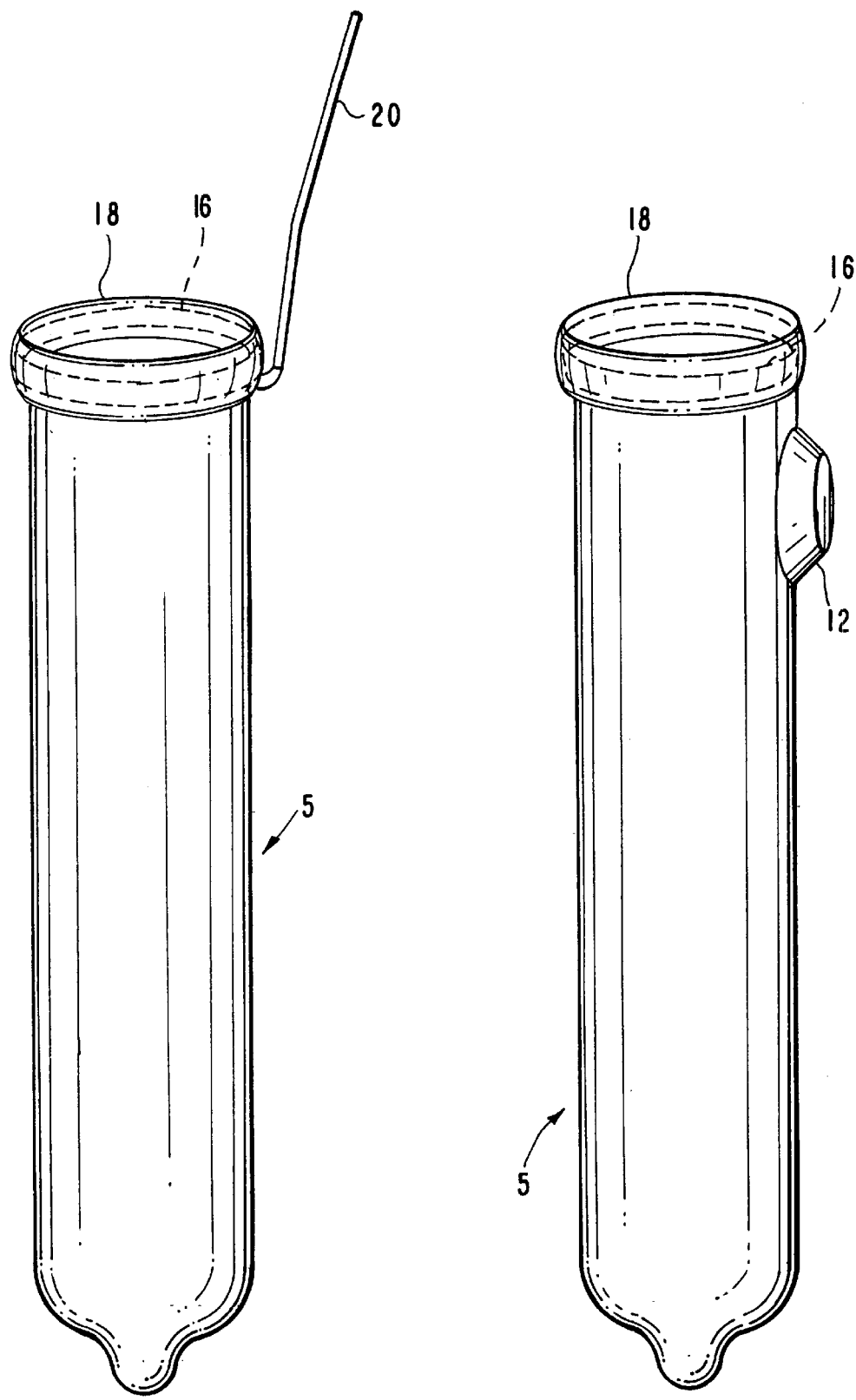

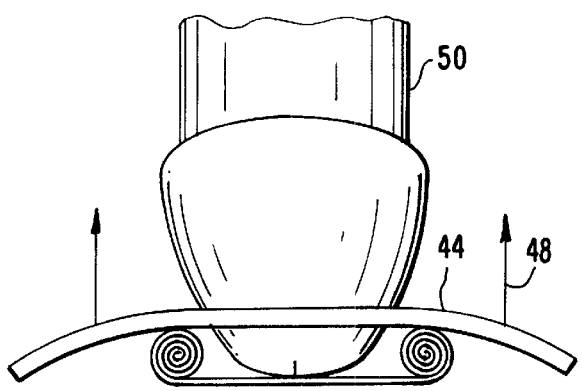
FIG.11a
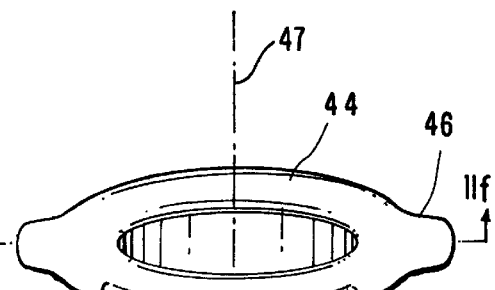
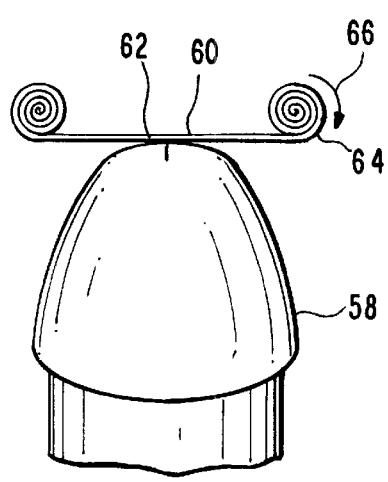
FIG.11b
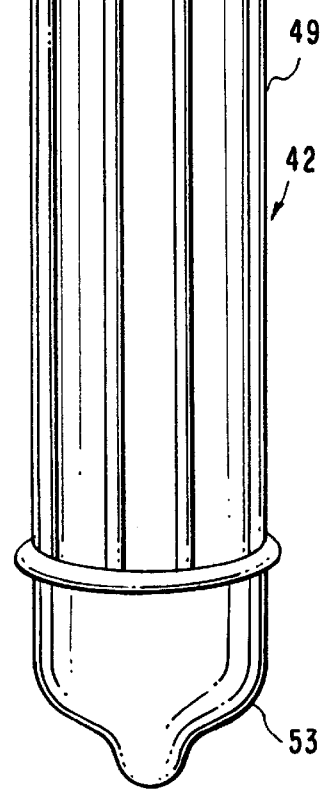
FIG.11
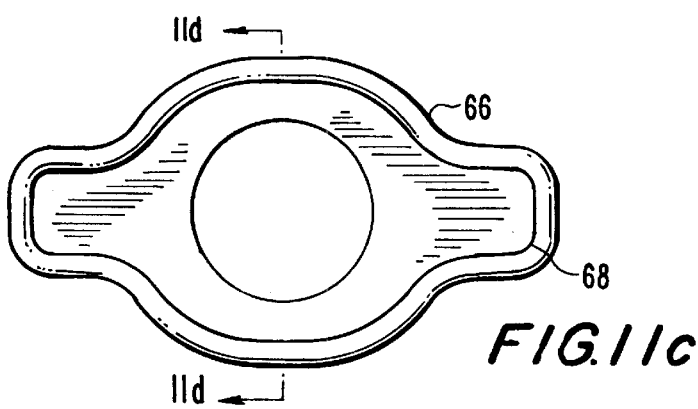
FIG.11c

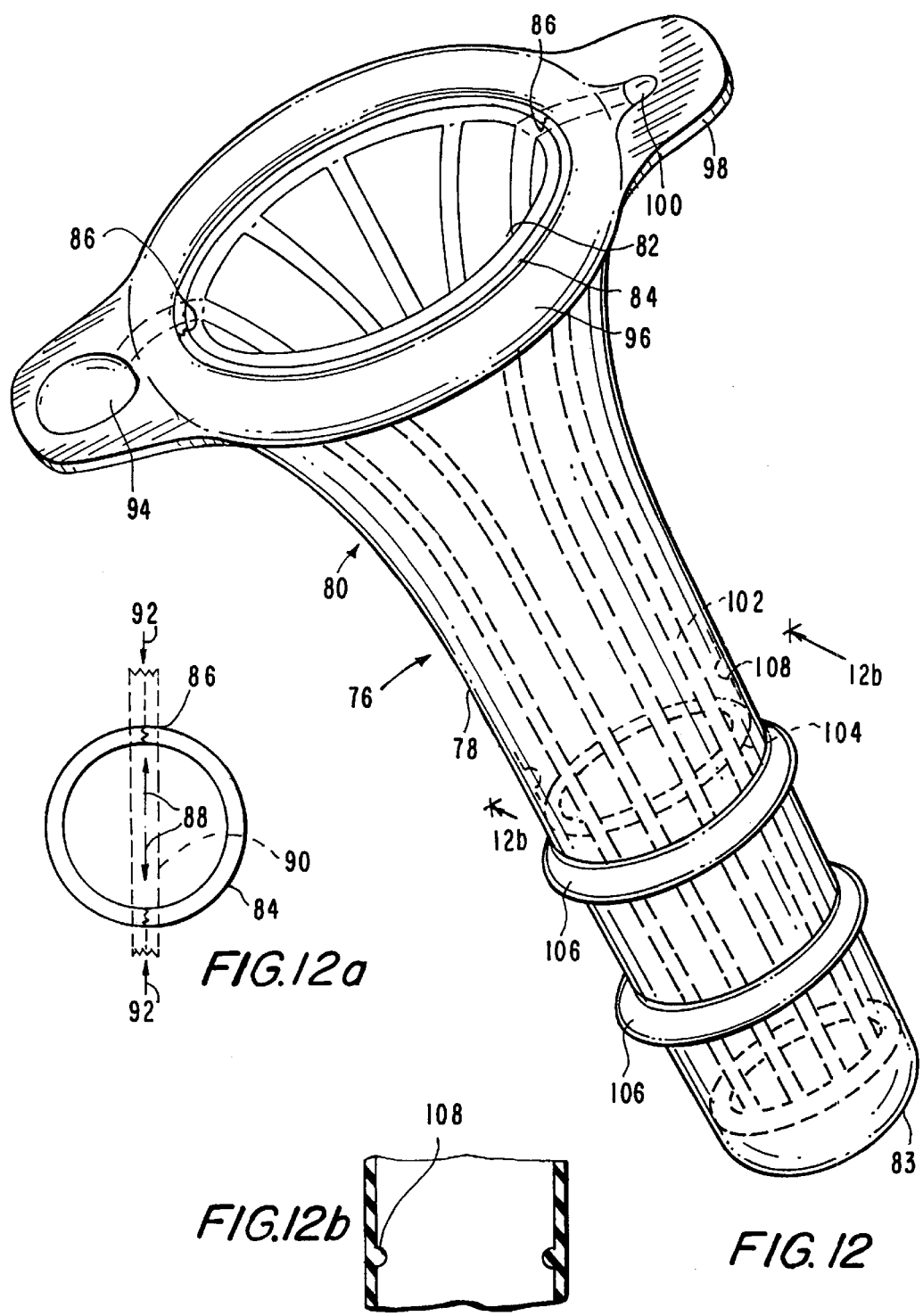

MALE, HERMAPHRODITIC, AND FEMALE CONDOMS EXERTING LATERAL PRESSURE ON THE PENIS AND THE VAGINA

CROSS-REFERENCE TO RELATED APPLICATION

This application is a continuation-in-part of U.S. application No. 08/725,562, filed on Oct. 3, 1996, U.S. Pat. No. 5,885,205.

BACKGROUND OF THE INVENTION

1. Field of the Invention

This invention relates to condoms for use by male and female persons during sexual intercourse and, more particularly, to condoms that are of variable stiffness.

2. Description of the Related Art

The earliest published description of the male condom was by the Italian anatomist Gabriel Fallopius in 1564. Early male condoms were generally made from animal intestines or fish membrane and were mostly used to prevent the sexual transmission of disease, a task which they often inefficiently performed. However, by the 17th century, male condoms were used as a contraceptive as well.

Most male condoms were made of vulcanized rubber from the 1840s to the 1930s after the discovery of the process for vulcanization of rubber by Charles Goodyear in 1839, and male condoms have been a popular, efficent, and generally convenient contraceptive method since the second half of the 19th century. Since the 1930s most male condoms have been made from latex. (The above historical material is based on information from *The New Encyclopedia Britannica,* Vol. 3, p. 522, Vol. 15, p. 114, 15th Edition, Encyclopedia Britannica, Inc., 1990.)

Recently with the large increase in births out of wedlock in the United States of America and many other western countries and the outbreak of Auto-Immune Deficiency Syndrome (AIDS) globally, the use of condoms as a contraceptive method and as a method of preventing the spread of sexually transmitted diseases has become urgent, both from a medical point of view and a societal point of view.

However, there are certain well known drawbacks to the use of male condoms, at least from the point of view of the male user. Some of these drawbacks are the inconvenience and delay occasioned by the necessity of applying a male condom immediately prior to intercourse when an erection of the penis is present. The often cumbersome process of applying the condom can result in a loss of erection during the time required for application making the condom useless and resulting in the frustration of the user. Even if application is successful, many male users complain of a loss of sensation and pleasure due to the interposition of the condom between the penis and the vagina during intercourse. Furthermore, such loss of sensation and pleasure may be additionally caused by the fact that conventional condoms do not closely conform to the geometry of an erect penis as such condoms are of circular cross-section, and an erect penis is of generally triangular cross-section as will be stated in further detail later. These drawbacks cause condoms to be irregularly used and, thus, to fail to fulfill their purposes.

U.S. Pat. No. 4,281,648 issued to Rogers discloses an inflatable male condom with a conventional tubular anterior portion apparently fitting over the base and lower shaft of the penis and an inflatable secondary portion extending from the anterior portion inflated by an air duct extending from the anterior portion to the secondary portion. Rogers purportedly enlarges the size of the penis in order to compensate for maladjustment in the two partners during coition.

However, Rogers seems to produce this enlargement only through the enlargement achieved by the inflatable secondary portion. In particular, there is minimal or no enlargement of the penis itself through lateral pressure since minimum ballooning of inner wall 12, presumably in contact with the penis after application of the condom, is desired when the expandible sheath 5 included in the secondary portion is inflated, (column 3, lines 37–41). Thus, it seems that Rogers increases the apparent size of the user's penis as sensed by the female participant without materially increasing the actual size of the user's penis or improving the user's erection. Moreover, the location of application of whatever pressure is exerted on the user's penis in Rogers seems to be at the end of the shaft of the user's penis and at the glans. Rogers fails to disclose or suggest pressure at the base of the penis, the most advantageous place to apply pressure in order to improve a user's erection and increase the size of the user's erect penis, as will be explained below.

This invention overcomes the drawbacks of Rogers by increasing the size of the user's erect penis, and increasing the duration and hardness of the user's erection through exertion of lateral pressure in locations designed to produce these results, especially including the base of the user's penis.

U.S. Pat. No. 4,432,357 issued to Pomeranz discloses a male condom which has a deformable chamber or chambers filled with a rheopexic fluid. A rheopexic fluid has the characteristic of thickening with increasing shear stress. The movements during intercourse allegedly create such shear stress causing the thickening of the fluid and the stiffening of the condom. This stiffening of the condom simulates an erection, (column 3, lines 32–36). This stiffening also creates pressure around the base end of the penis at least in one embodiment, thereby prolonging a user's erection by prolonging the time required for disengorgement of blood vessels within the penis, according to the disclosure in Pomeranz, (column 5, lines 1–8).

Pomeranz, although purportedly addressing the problem of a loss of pleasure, does not ameliorate the problem of a loss of erection during application since any stiffening effect would normally only occur during intercourse. Moreover, Pomeranz relies on the use of a rather exotic material, namely, the rheopexic fluid to achieve the desired stiffening effect.

This invention eliminates the drawbacks of Pomeranz by preventing a loss of erection during and after application of the condom and achieves its improvement of the user's erection with the use of readily available methods and substances and without resorting to the use of exotic substances.

This invention makes substantial progress in overcoming the problem of a loss of sensation and pleasure during intercourse, thereby encouraging the more widespread use of condoms, particularly as a contraceptive method and as a measure to prevent the spread of sexually transmitted diseases.

One male embodiment of the invention is particularly designed to allow a male user, who cannot achieve a normal erection, to engage in sexual intercourse, while still enjoying the barrier benefit of a conventional condom, the male embodiment of the invention simulating an erect penis.

Female barrier contraceptive devices are of early origin. For example vaginal plugs of local material such as honey and crocodile dung in Egypt, wool mixed with cedar gum in ancient Rome, and beeswax in medieval Europe were made and inserted. In the United States of America, an early patent was granted for a vaginal diaphragm, Beers, U.S. Pat. No. 4,729, and patents for vaginal barrier pessaries, "block" pessaries, intrauterine stem pessaries, and dissolving chemical pessaries followed. (The above historical material is based on information obtained from *American Sex Machines: The Hidden History of Sex at the U.S. Patent Office,* pp. 6–8, 58–67, Hoag Levins, Adams Media Corporation, 1996.)

Relatively recently, there has been an increasing desire to shift the responsibility for protection against conception and disease from men to women. This shift in attitude has been reinforced by studies by world health authorities suggesting a general distrust of the male in connection with the consistent use of condoms. The facts that women are more affected by pregnancy and childbirth than men and that women are more likely to be infected by a male carrier of AIDS than men being infected by a female carrier of AIDS also give women a greater motivation to use contaceptive and prophylactic devices than men.

This invention addresses the desire for female control of contraception and disease prevention by providing a device that can be used by men or women (in at least one embodiment, by both men and women) and, when a woman is using the device, the invention can be applied well before intercourse and in the absence of any sexual stimulation, which may prove a distraction to correct application by either partner.

Recent efforts in the field of barrier contraceptive devices for women have produced many patents for female condoms or like devices, some of which are described below.

Ludwig, U.S. Pat. No. 3,536,066, discloses a pant-like device which is donned by a woman prior to intercourse. It has a hollow proboscis over the center of the device with a bellows-like longitudinal structure. During intercourse, the male inserts his penis into the proboscis which is designed to invert and extend into the vagina. However, the device may be awkward to wear, and may cause irritation to the female user if worn for any length of time.

Hessel, U.S. Pat. No. 4,735,621, discloses a tubular thin walled conically shaped device closed at one end which is designed to be inserted into the vagina and open at the other end which extends from the vagina. Both ends have elastic rings attached, the elastic ring at the inner end of the vagina serving to seat the condom in the vagina and the elastic ring at the open end of the condom preventing the condom from being pushed into the vagina during intercourse and radially stetching the open end to cover the base of the penis and vulva during intercourse, thus preventing to exchange of body fluids during intercourse. The use of only two retaining rings, however, seems to be insufficient to hold the condom in place during intercourse, and the conical geometry of the condom may not provide a very effective form fitting barrier between the penis and the vulva.

Lee, U.S. Pat. No. 4,840,624, discloses a tubular sheath analogous to a male condom to be inserted within the vagina by an insertion tool. The condom is held in place by a system including a cover pad from which the condom extends and a set of tapes to extending about the legs and optionally the waist of the wearer. Again, the cover pad and set of tapes may be unwieldy, inconvenient, and liable to be broken or otherwise damaged during intercourse, possibly adversely affecting the effectiveness of the device.

Lash, U.S. Pat. No. 4,867,176, discloses various female condoms of generally tubular shape for the majority of their length and a generally conically shaped opening. A telescoping applicator for inserting the condom into the vagina is also disclosed. Various means for holding the condom in the vagina, namely, elastic retaining rings on the open end of the condom and expanding fingers on the outside of the closed end of the condom are disclosed. The means of holding the condom in the vagina, however, shares the possible infirmity already discussed in regard to Hessel, and the conical opening may not be very effective prophylactically, as also discussed in connection with Hessel.

Reddy, U.S. Pat. Nos. 4,993,431 and 4,993,433, generally disclose female condoms comprising a tubular sheath inserted in the vagina and various shields or panties to protect the perineum of the female user from transmission of disease. The presence of these shields or panties, however, may make the device inconvenient and awkward to use.

Reddy, U.S. Pat. No. 5,325,871, assumes the use of the same shields or panties as the previously mentioned Reddy patents, but adds a member for inserting and holding the tubular sheath in the vagina during intercourse. The member also is filled with a lubricant to lubricate the interior of the sheath.

Artsi, U.S. Pat. No. 5,515,862, discloses a flexible tube for insertion into the vagina having an open end and a closed end, and a shield attached to the tube for covering the perineal region, pubic region, lower abdomen, groin region, and part of the thighs of a female user. Adhesive is applied to the shield for attachment to the user. Semi-rigid rings along the length of the tube serve to secure it in the vagina. The possible inconvenience of the shield must again be endured by the user.

Abadi, U.S. Pat. No. 5,596,997, discloses a panty with a slit opening approximately over the vagina of the female wearer. In a preferred embodiment, a pouch is affixed to the panty also having a slit in its front and rear sides aligned with the slit in the panty. A sheath is postioned within the pouch behind the slit in the front side of the pouch such that when a male's erect penis enters the slit in the panty and the slit in front of the pouch, the penis extends the sheath through the slit in the back side of the pouch and into the vagina of the wearer. Although a panty with no discernible external difference from an ordinary panty seems more convenient to wear than the other female condoms previously discussed, such an apparatus may be too easily defeated by the removal of the panty by either the female wearer or a male.

Thus, there exists a need for a female contraceptive and prophylactic device which is effective, does not entail inconvenience in its application, and yet is not easily defeated by removal or otherwise prior to sexual intercourse since it is designed to remain in the vagina prior to intercourse once applied. The invention disclosed embodies a substantial advance in meeting these objectives.

SUMMARY OF THE INVENTION

The invention in all of its embodiments disclosed herein, except for one, comprises male, hermaphroditic, and female condoms, each condom possessing an added means for exerting lateral pressure on the shaft of the penis and the wall of the vagina. In one embodiment, the invention comprises a means for exerting lateral pressure on the shaft of the penis and the wall of the vagina adapted to be removably attached to any of the aforementioned condoms. (The term lateral pressure, whenever used in this application, indicates that the forces producing the nonischemic pressure act in directions such that at least a component of the forces act substantially normal to the surface or region acted upon at each point of action of the forces.)

In the case of a male user applying the condom, the lateral pressure exerted will preferably be exerted around the circumference of the penis at the time of activation of the means for exerting lateral pressure, although pressure can be exerted along the length of the penis in addition to or in place of circumferential pressure. A male user applying the condom will typically activate the pressure exerting means at the time of application, by the injection of air into the pressure means or by alternative mechanical means, thereby assuring the continuation of his erection. Moreover, the pressure exerting means will tend to increase the duration of the erection and the hardness and size of the male user's erect penis, thereby compensating or tending to compensate for any loss of sensitivity or pleasure due to the wearing of the condom during intercourse. Even if the male user initially applies the condom, the pressure exerting means will also exert pressure on the vagina of a female during sexual intercourse, thus possibly tending to increase the sexual pleasure of the female partner. In the embodiment designed to be worn by males incapable of achieving an erection, the condom still exerts lateral pressure on the flaccid or partially erect penis of the user, but also expands and exerts lateral pressure on the enclosed air space extending beyond the penis of the user, thereby forming a simulated erect penis.

In the case of a female user applying the condom, the lateral pressure exerted will be applied around the circumference of the wall of the vagina at the time of activation of the means for exerting lateral pressure, and additional pressure along the length of the wall of the vagina will be exerted as well. The female user applying the condom will employ an application means to insert the condom into her vagina at some period before intercourse and, preferably, before any foreplay commences. At some later time, but preferably still prior to initial insertion of the penis into the vagina, the pressure exerting means will be activated by the female user through the injection of air or other expansive substance, the air or other expansive substance being or not being contained within the condom. The pressure exerting means, by exerting lateral pressure on the wall of the vagina, tends to insure that the condom remains firmly seated in the vagina during intercourse. The pressure exerting means will also exert lateral pressure on the erect penis while it is in the vagina, thus tending to increase the duration of the erection and the hardness and size of the male's erect penis, thereby tending to compensate for any loss of sensitivity or pleasure due to the wearing of the condom during intercourse.

Whether a female or male applies the condom initially, the pressure exerting means shall be so designed as to attempt to maximize the probability that the male's penis, upon withdrawing from the vagina after intercourse, will either leave the condom firmly seated in the vagina or the condom will enclose the penis upon and after withdrawal from the vagina.

Additionally, the invention comprises a removably attachable means for exerting lateral pressure on both the penis and the vagina during sexual intercourse, the removably attachable means being removably attached to a tubular membrane and being possibly reusable.

An object of this invention is to supply a condom which prevents the loss of erection during application of the condom by a male user.

A further object of the invention, is to supply a condom which exerts lateral pressure on the penis.

A further object of the invention is to supply a condom which exerts such lateral pressure on the penis by readily available means.

A still further object of the invention is to supply a condom which exerts such lateral pressure at locations designed to increase the size and hardness of the user's penis during erection and the duration of the erection.

A still further object of the invention is to supply a condom which compensates or tends to compensate for any loss of pleasure during sexual intercourse with the condom applied by increasing or tending to increase the size and hardness of the male's penis during erection, increasing the duration of the male's erection, and increasing the frictional forces on the male's penis during intercourse.

A yet further object of the invention is to supply a condom which will, upon application to the flaccid or partially erect penis of a user, simulate an erect penis.

A further object of the invention is to supply a condom which is easily inserted into the vagina of a female user.

A further object of the invention is to supply a condom which exerts lateral pressure on the wall of the vagina during intercourse and increases the forces on the wall of the vagina during intercourse.

A yet further object of the invention is to supply a condom which remains firmly seated in the vagina of a female user during intercourse.

A still further object of the invention is to supply a condom which tightly and wholly encloses the penis of a male user during intercourse.

A yet further object of the invention is to supply a condom which remains stationary in the vagina while the penis is withdrawn after intercourse or is withdrawn along with the penis while tightly and wholly enclosing the penis.

A still further object of the invention is to supply a means for exerting lateral pressure on the penis and the vagina during sexual intercourse, the means being removably attached to a tubular membrane.

A yet further object of the invention is to achieve all of the previously mentioned objects consistent with the safety of the male and female coming into contact with the condom supplied and consistent with the comfort of the male and female.

These and other objects and advantages of the present invention will become more apparent to those of ordinary skill in the art upon consideration of the attached drawings and the following description of the preferred embodiments which are meant by way of illustration and example only, but are not to be construed as in any way limiting the invention disclosed and claimed herein.

BRIEF DESCRIPTION OF THE DRAWINGS

FIG. 4 is a perspective view of a fourth embodiment of the invention.

FIG. 5 is a perspective view of a fifth embodiment of the invention.

FIG. 11 is a perspective view of an eleventh embodiment of the invention.

FIG. 11a is a side view of the eleventh embodiment of the invention being applied to the penis of a user.

FIG. 11b is a side view of a conventional condom being applied to the penis of a user.

FIG. 11c is a plan view of the eleventh embodiment of the invention showing an upper lip and an optional membrane extension to the upper lip in a rolled up state.

FIG. 12 is a perspective view of a twelfth embodiment of the invention.

FIG. 12a is a schematic view showing the operation of the flexible ring located around the open end of the twelfth embodiment of the invention.

FIG. 12b is a sectional view of FIG. 12 taken along section lines 12b—12b in FIG. 12 showing an optional constriction of the internal diameter of the twelfth embodiment of the invention.

FIG. 13 is a perspective view of a first embodiment of an applicator for applying the twelfth embodiment of the invention.

FIG. 13a is an enlarged partial cross-sectional view of the first embodiment of the applicator.

FIG. 13b is an enlarged view of a portion of FIG. 13a.

DESCRIPTION OF THE PREFERRED EMBODIMENTS

For a more detailed description of the invention in its several embodiments, given only by way of example and not to be construed as limiting the invention in any fashion, we refer to the drawings.

Figure 1A:
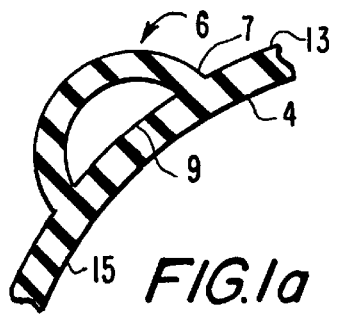
FIG. 1a is a cross-sectional enlarged detail of a microtubule shown in FIG. 1.
Figure 1B:
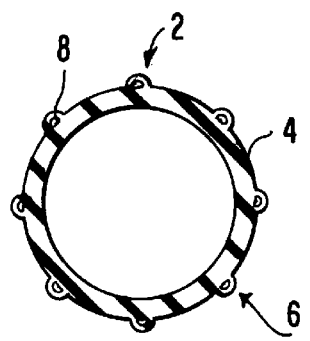
FIG. 1b is a sectional view of FIG. 1 taken along section lines 1b—1b in FIG. 1.
Figure 1C:
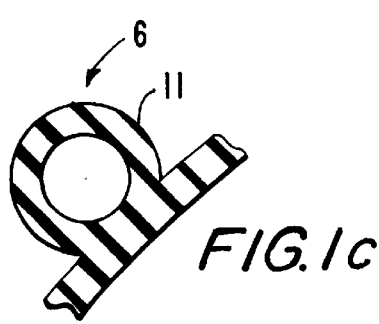
FIG. 1c is a cross-sectional enlarged alternative detail of a microtubule shown in FIG. 1.
Figure 1:
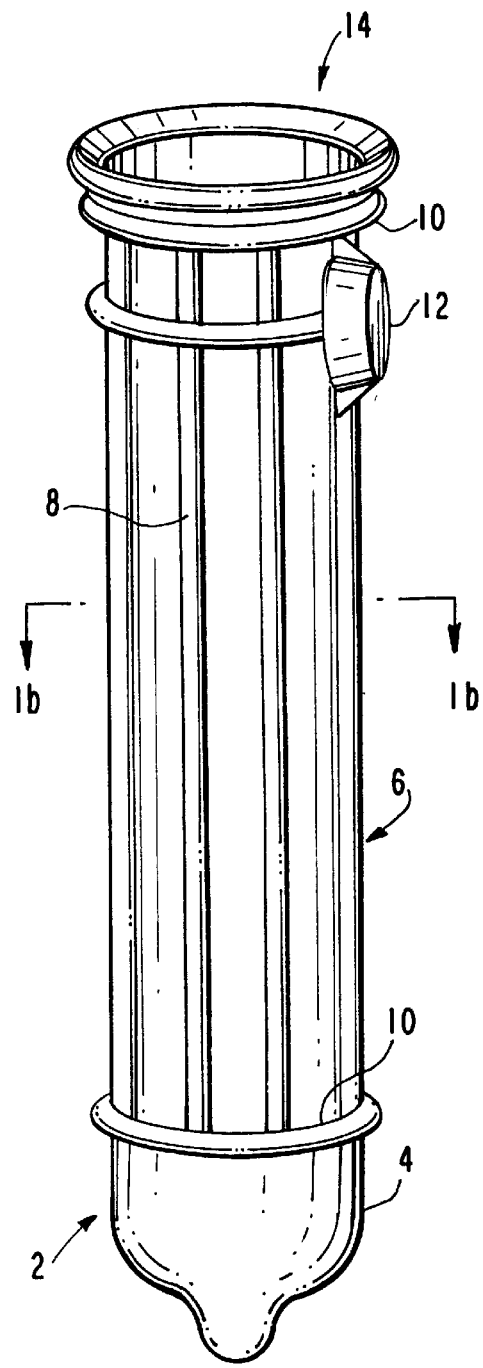
FIG. 1 is a perspective view of a first embodiment of the invention.

FIG. 1 represents the first embodiment of the invention. In this embodiment, a condom 2 comprises a membrane 4, which may be thicker than the membrane of a conventional condom, contacting the penis of the user, on which membrane is formed or applied microtubules 6.

These microtubules 6 may be of a circular cross-section or may be of any other closed cross-section. It should be particularly noted that certain cross-sections may be formed which will produce different forces in different regions along the cross-section, thus permitting higher or lower forces to be exerted in certain directions. For example, FIG. 1a shows a cross-sectional enlarged detail of the microtubules 6 attached to the membrane 4, the microtubules 6 having a generally semicircular cross-section 7 on one side protruding above the rest of the membrane 4 and a cross-section with a much larger radius of curvature on the other side being part of the membrane 4. The larger radius of curvature corresponds to the radius of the condom 2. The force exerted on the semicircular side when air or another expansive substance is introduced into the microtubules 6 will be greater simply because of the greater length of the semicircle compared to the length of the curve 9 of much larger radius of curvature. FIG. 1c shows a detail of a cross-section of a microtubule 6 where the microtubule 6 forms a circular cross-section 11. In this case, of course, the microtubule, when inflated, exerts equal force in all directions because of the geometry of a circle. Finally, the thickness of the microtubules 6 may be varied around their perimeter with the result that thinner regions of the microtubules will expand under inflation more than relatively thicker regions of the microtubules.

The membrane 4 has a circular cross-section (see FIG. 1b) and is cylindrical in shape when extended, the same as other conventional condoms. Such microtubules 6 comprise longitudinal microtubules 8, which extend along a portion of the length of the condom 2 and circumferential microtubules 10 which extend around the circumference of the condom 2. It should be noted that, preferably, neither the longitudinal microtubules 8 nor the circumferential microtubules 10 should be placed in the region of the condom 2 contacting the glans penis since any pressure exerted by microtubules 6 on the glans penis may tend to decrease the sensation and pleasure of the male user during intercourse.

The condom 2 also comprises an inflation compartment 12. The condom 2 is preferably made from a polyurethane polymer or other equivalent material allowing the formation of the microtubules 6 when the condom 2 is heat treated, heat sealed using radio frequency welding, heat sealed using ultrasonic welding, or dipped, depending upon the process of manufacture utilized. These equivalent materials may include other polymers and elastomers. Some of these materials may include, for example, the polyolefins, including polyethylene and polypropylene, block copolymers, such as a polyether copolymer and styrene-ethylene-butylenestyrene, and vinyl, from which condoms have been proposed to be made, see Abadi, U.S. Pat. No. 5,596,997, McGlothlin et al., U.S. Pat. No. 4,855,169, Sorkin, U.S. Pat. No. 4,808,174, and Buddenhagen et al., U.S. Pat. Nos. 5,112,900 and 5,407,715. However, a polymer used for the condom 2 possibly may not be an elastomer since the required elasticity of the condom 2 to conform to the differing sizes of the erect penises of users may be supplied by the inflation of the microtubules 6.

The heat treatment, heat sealing, or dipping causes the fibers of the polyurethane or other equivalent material to align and form the microtubules 6. Polyurethane also has the advantage of being less permeable to viruses than latex, for example, a conventional condom material. Although latex condoms may offer the best protection against infection with the virus causing AIDS, persons with an allergy to latex cannot use latex condoms. This allergy affects roughly 3 percent of the population, with fatal results sometimes occurring, see *The New York Times,* Mar. 7, 1999, pp. 1, 43.

FIG. 1 shows the condom 2 after inflation. Such inflation will be accomplished through the use of air injected through the inflation compartment 12. Such air can be injected through the crushing of a compressed air pellet (not shown) placed in the inflation compartment 12, through an external tube (not shown) leading into the inflation compartment 12 from an air pump or air syringe (not shown), or through an external tube (not shown) supplied with air by aspiration of the user or another person. The air, if supplied by the crushing of a compressed air pellet or from an air pump, may or may not be sterilized. The air injected into the inflation compartment 12 will pass from there through the microtubules 6 which, for example, have internal apertures connecting all the microtubules 6 and the inflation compartment 12 together. Alternatively, the microtubules 6 may be connected to the inflation compartment 12 by any method known to one with ordinary skill in the art. A one-way valve or valves, seal or seals, or other equivalent device(s) (not shown) are placed in appropriate location(s) in the microtubules 6, inflation compartment 12, or in both to insure that the microtubules 6 retain any air injected into them. The central axis of the cross-section of the microtubules 6 has been located such that the walls of the microtubules 6 cause a protrusion beyond the otherwise existing exterior surface 13 of the wall of the membrane 4, without causing any protrusion beyond the otherwise existing interior surface 15 of the wall of the membrane 4, (see FIG. 1a).

The air in the microtubules 6 will exert lateral pressure on the user's penis around the circumference of the penis due to the circumferential microtubules 10 and along the length of the user's penis due to the longitudinal microtubules 8. This lateral pressure on the user's penis acts in a manner akin to a tourniquet placed on another part of the user's body. A tourniquet traps blood in those portions of the body to one side of the tourniquet which are further distant from the center of mass of the body and, thus, is effective in stopping bleeding. In the same way, the lateral pressure exerted on the user's penis by the microtubules 6 will trap blood in the user's penis. Since an erection is ordinarily caused by an increase in the supply of arterial blood to blood interspaces in the three cylindrical masses of cavernous tissue of which the penis is comprised, two of those masses being known as the corpora cavernosa penis, and the third denoted as the corpus spongiosum penis, see *Anatomy of the Human Body,* pp. 1310, 1314, by Henry Gray, Charles Mayo Goss, editor, 29th American Edition, Lea & Febiger, 1973, the trapping of such blood will increase the size, hardness, and duration of a user's erection, thereby increasing the stimulation and pleasure of the user.

In particular, it is highly preferable that at least one of the circumferential microtubules 10 be located at the open base 14 of the condom 2 located at the base of the user's penis when the condom is applied thereto. Such a location of at least one of the circumferential microtubules 10 will apply circumferential pressure to the base of the user's penis acting in a way most analogous to the tourniquet previously mentioned and trapping as much blood as possible in the user's penis.

The longitudinal microtubules 8 primarily will aid the user in maintaining his erection through the stiffening effect achieved by the pressure which they exert laterally to the user's penis and longitudinally along the length of the user's penis. Such longitudinal microtubules 8 will additionally act to further secure the condom onto the erect penis of the user as well as onto the partially flaccid penis of the user after ejaculation. This characteristic will help solve the problem of the condom slipping off the penis after ejaculation and before or during withdrawal of the penis from the vagina. In addition, the mircrotubules 6 will exert lateral pressure on the wall of the vagina during coitus and thus increase the probability that the condom will be retained within the vagina, thereby being designed to preferably prevent any exchange of body fluids, in the event that the condom does slip off the penis after ejaculation and detumescence and before or during withdrawal of the penis from the vagina.

The microtubules 6 will also increase stimulation during sexual intercourse because the microtubules 6 increase the surface area of the condom 2 over that of a conventional condom, thereby increasing the potential contact area between the condom 2 and the vaginal walls over the contact area obtained with or without a conventional condom. This increased contact area and the increased frictional forces generated will provide increased stimulation and pleasure for the male and female participant. The microtubules 6 will also increase frictional forces generated by the penis moving within the vagina and thus increase stimulation and pleasure for the participants in sexual intercourse due to the lateral pressure exerted by the microtubules 6 on the wall of the vagina. Moreover, the circumferential microtubules 10 will exert circumferential pressure on the shaft of the penis, resulting in a bulging of the side of the shaft of the penis which is more distant from the center of mass of the body relative to the circumferential microtubules 10. Such bulging, when in close proximity to the vaginal wall during intercourse, will create increased frictional forces over those present in the absence of such bulging, resulting in increased stimulation and pleasure for the male and female participant.

It should be understood that the microtubules will be designed to accomodate an air pressure that is the maximum safe value for the user. The pressure should be such a maximum to achieve the maximum blood trapping and stiffening effect on the penis of the user, but cannot exceed the maximum, lest injury result to the user.

Thus, the walls of the microtubules 6 may be designed so that they rupture if the user attempts to introduce an air pressure beyond the maximum safe value into them. Alternatively, the microtubules 6 may be designed to balloon in such a way as to make the condom unusable if the user attempts to introduce an unsafe air pressure into them. It should be noted that any inflation must be completed before intercourse to prevent any injury to the female participant if a condom falls due to overinflation in one of the ways previously described. Furthermore, a relief valve (not shown) may optionally be provided as a further safety feature allowing for a decrease in air pressure in the microtubules 6 in the event of excessive air pressure in any portion of the microtubules 6. Of course, the user through the use of an air pump or selected air pellets may select any air pressure less than the maximum safe value in accordance with the comfort of the user.

The condom 2 will be applied initially as a conventional condom is applied, either manually or by means of any condom applicator or similar contrivance. At the time of the application, the user will be required to have an erection as is required for the application of a conventional condom. After application and before sexual intercourse, air will be injected into the condom 2 through the inflation compartment 12 until the air pressure in the microtubules 6 reaches the comfort level of the user or the maximum safe value, whichever is less.

Prototypes of the inventive condom have been produced. The unstretched dimensions of the prototypes follows. The prototypes measure in the approximate ranges of 180–190 mm and 200–210 mm long by the approximate ranges of 57–59 mm and 64–65 mm in width. The length of the tubular network on the condoms is approximately 87–89 mm. The wall thickness of the condom membrane alone is approximately 0.030–0.038 mm. The thickness of the microtubules alone is approximately 0.070–0.100 mm. The approximate distance from the closed tip of the condoms to the circumferential microtubule furthest from the tip is in the ranges of approximately 57–59 mm and 82–83 mm. The prototypes tested by inflation of the microtubules require approximately 2.5 pounds per square inch (psi) of air pressure on the inside of the microtubules to inflate them and the microtubules fail at approximately 8–8.5 psi internal air pressure. Of course, it should be noted that all of the data disclosed for these prototypes are illustrative and exemplary only, and are not to be construed as limiting or otherwise definitive regarding any preferred embodiments or manufactured specimens of the invention.

Figure 2:
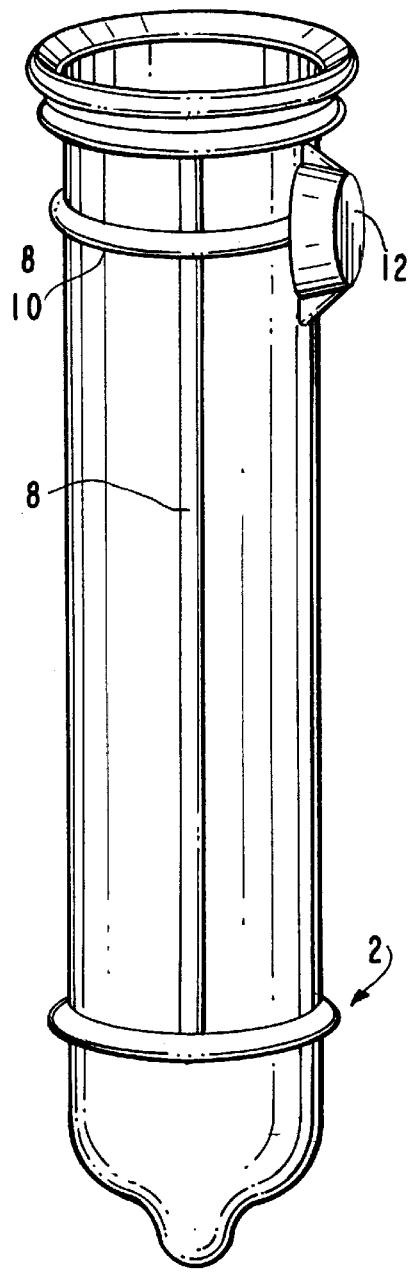
FIG. 2 is a perspective view of a second embodiment of the invention.

A second embodiment of the invention is shown in FIG. 2. The sole difference from the first embodiment is that, instead of a plurality of longitudinal microtubules 10 as shown in FIG. 1, only one longitudinal microtubule 8 is shown in FIG. 2. Such an arrangement of only one longitudinal microtubule 8 would be directed more toward stiffening the condom rather than exerting significant lateral and longitudinal pressure along the length of the user's penis.

Figure 3:
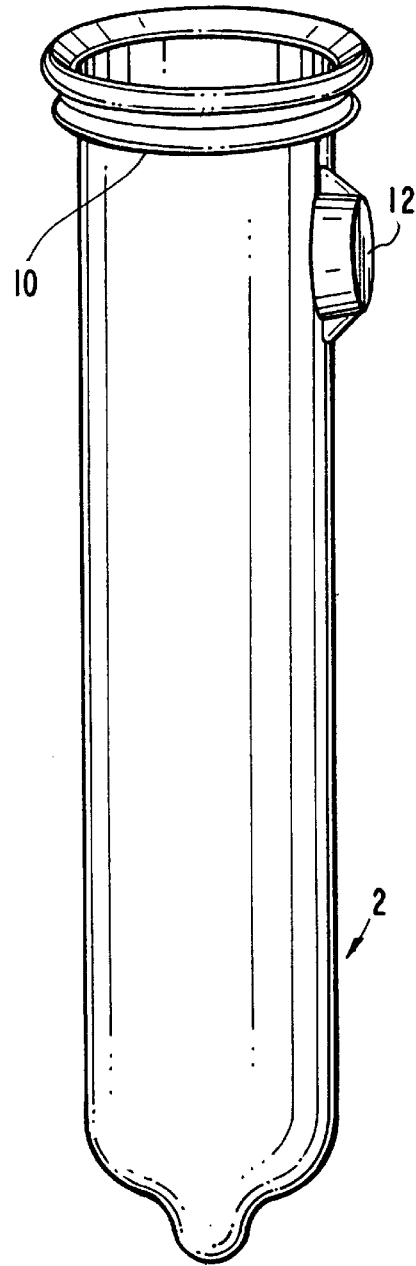
FIG. 3 is a perspective view of a third embodiment of the invention.

FIG. 3 shows a third embodiment of the invention. The third embodiment differs from the first two embodiments in that only one circumferential microtubule 10 is present and no longitudinal microtubules 8 are present in contrast to the first two embodiments in which at least one longitudinal microtubule 8 is present and a plurality of circumferential microtubules 10 are present. The one circumferential microtubule 10 present is placed at the base of the condom so as to attain maximum safe tourniquet effect for only one microtubule since that microtubule will apply a tourniquet force to the base of the penis. However, additional tourniquet, stiffening, and lateral forces provided by additional circumferential microtubules 10 and longitudinal microtubules 8 are absent.

FIG. 4 shows the fourth embodiment of the invention. In contrast to the first three embodiments of the invention, the condom 5 is made from a conventional condom material, latex, and it contains no microtubules 6. An inflation compartment 12 is also present as in the previous three embodiments with an analogous purpose to inject air into the condom 4 by any of the means previously disclosed. However, instead of injecting air into microtubules 6, the air is injected into a toroidal chamber 16 within a hollow lip 18 at the open end of the condom 5. Upon air being injected into the toroidal chamber 16, the chamber exerts circumferential and lateral pressure like a tourniquet on the base of the user's penis in a manner fully analagous to that of the circumferential microtubules 10 located at the base 14 of the condom 2 in the first three embodiments of the invention. Similarly to the first three embodiments of the invention, at least a single one-way valve, seal, or other equivalent means are located in appropriate location(s) in the inflation compartment 12, toroidal chamber 16, or in both to insure that the toroidal chamber 16 retains any air injected into it. This embodiment has the advantages of using a conventional condom material such as latex, instead of polyurethane, and the elimination of the difficulty involved in manufacturing a condom with microtubules, replacing them with a single toroidal chamber 16.

The fifth embodiment of the invention is shown in FIG. 5. It differs from the fourth embodiment of the invention in that a tube 20 leading directly to an air pump (not shown) or to the mouth of a user or other person is used to feed air directly into the toroidal chamber 16, instead of through an inflation compartment. This has the advantage of simplicity of construction since it eliminates the need for an inflation compartment 12, but this embodiment limits the mode of inflation to one which is based on a tube 20, whereas an inflation compartment, as in the fourth embodiment of the invention, can accommodate an air pellet as well.

Figure 6:
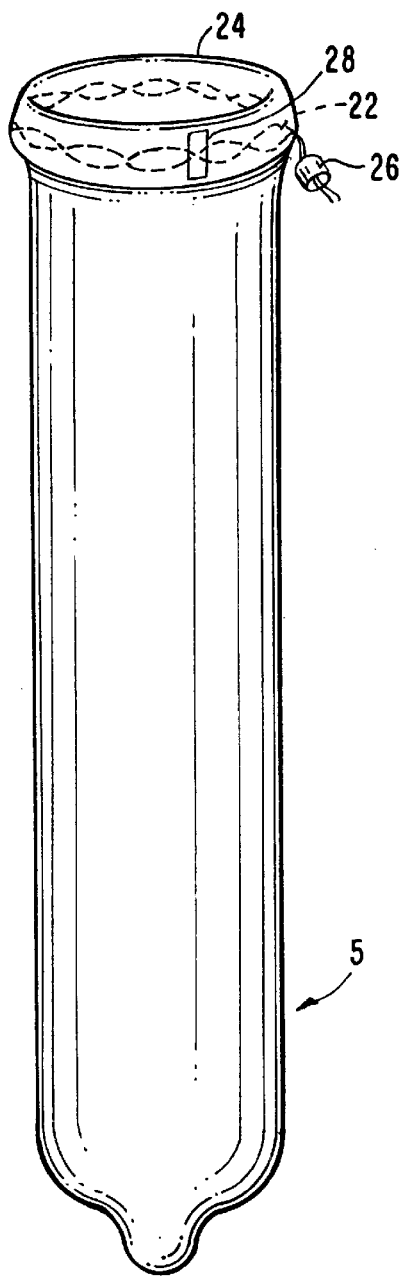
FIG. 6 is a perspective view of a sixth embodiment of the invention.

The sixth embodiment of the invention is shown in FIG. 6. Like the fourth and fifth embodiments, it too is constructed from latex. It differs in that no air or other gaseous means are provided to exert the lateral pressure needed. Instead a linear tightening device 22 is located in a hollow lip 24 at the open end of the condom 5. A bead or other adjustment device 26 is located on the linear tightening device 22 on the outside of the lip 24 to allow the user to tighten the linear tightening device 22 around the base of his penis after the application of the condom 5 to achieve the desired lateral pressure and tourniquet effect. The bead or other adjustment device 26 preferably comprises a locking mechanism (not shown), such as interlocking teeth, for example, and a means (not shown) for assuring instant manual release of the bead or adjustment device 26, such as by squeezing apart the locking mechanism, for example. The locking mechanism serves a function analagous to that of the one-way valve(s), seal(s), or equivalent device(s) in the first five embodiments of the invention, namely, assuring a constant lateral pressure on the user's penis. The instant manual release allows an added function, not present in the first five embodiments. It will allow the release of the lateral pressure entirely at any time. In contrast, the one-way pressure devices on the first five embodiments only allow for the maintenance or increase of lateral pressure, not the decrease of lateral pressure. Furthermore, the first five embodiments only contemplate the increase of lateral pressure prior to intercourse because of the danger to the female partner from condom failure due to overinflation during intercourse. This embodiment of the invention, however, allows increase of lateral pressure during intercourse with no danger to the female participant since no overinflation risk is present.

Some means, however, must be available to prevent the user from endangering himself by tightening the linear tightening device 22 excessively. Such means can, for example, take the form of a stop 28 located on the linear tightening device 22, preventing the reduction of the circumference of the linear tightening device 22 beyond a certain amount. The sixth embodiment of the invention has the advantage of simplicity of construction and use over the other embodiments since it relies on simple mechanical means to achieve the desired lateral pressure.

It should be understood that, although the word circumference has been used repeatedly in connection with the invention and the term normally refers to the perimeter of a circle, in this application the term should be interpreted broadly to also include the perimeter of any closed shape, In particular, in this connection, it should be noted that although conventional condoms are circular in cross-section and, therefore, cylindrical when extended, as were the first six embodiments of the invention disclosed herein, it may be preferable for the condoms disclosed and claimed herein to be substantially triangular in cross section to achieve the maximum lateral pressure on the penis of a user, given a certain air pressure or amount of other constricting force. This is because an erect penis "assumes the form of a triangular prism with rounded angles", see *Anatomy of the Human Body,* p. 1310, by Henry Gray, Charles Mayo Goss, editor, 29th American Edition, Lea & Febiger, 1973. Thus, a condom with a substantially triangular cross section, in particular, a cross section in the shape of a triangle with rounded corners, and assuming the shape of a triangular prism when extended achieves a tighter fit on the erect penis of a user than a conventionally shaped condom and exerts more lateral pressure on the penis for a given air pressure or amount of other constricting force.

Figures 7, 7A:
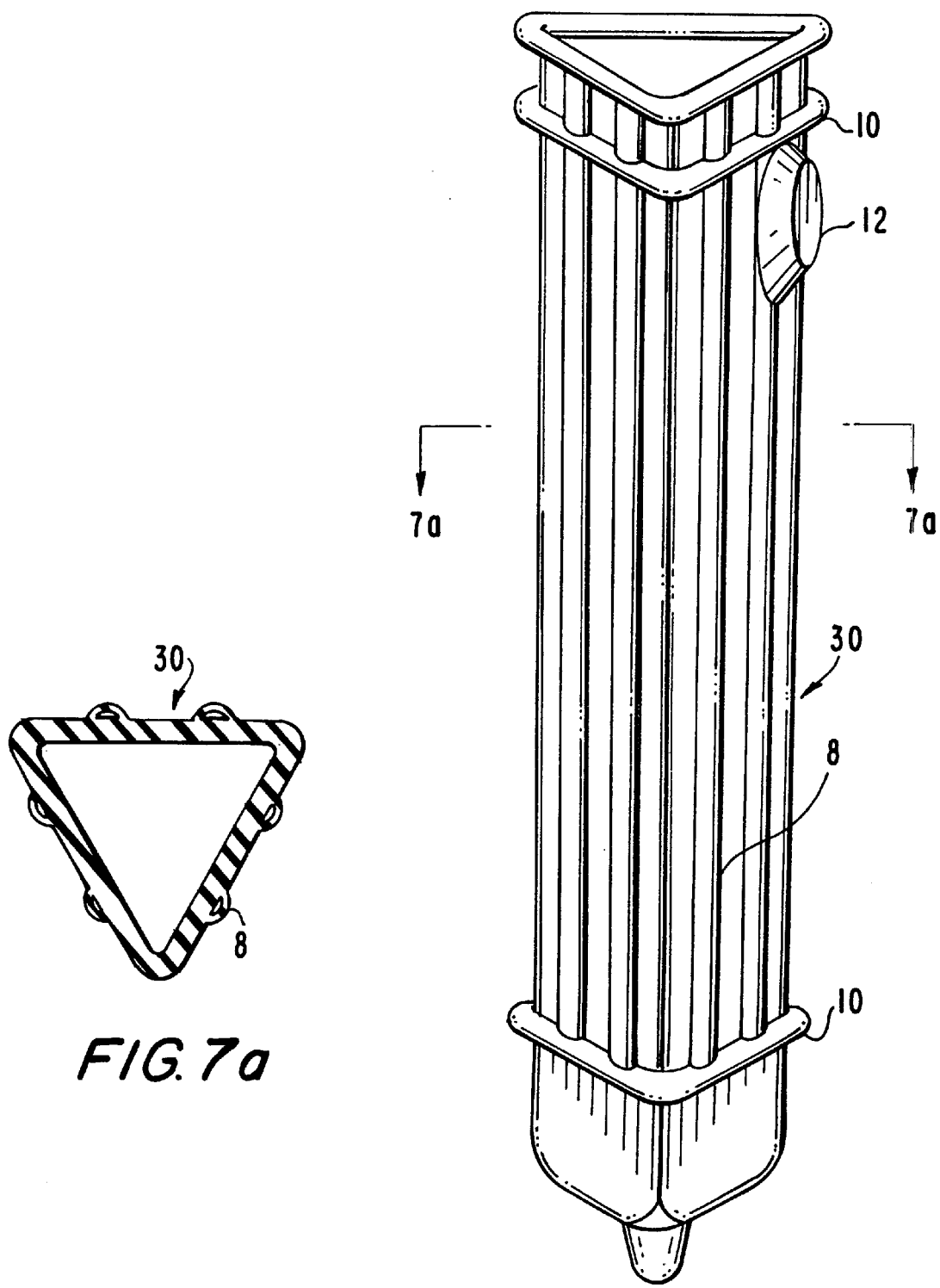
FIG. 7 is a perspective view of a seventh embodiment of the invention.
FIG. 7a is a sectional view of FIG. 7 taken along section lines 7a—7a in FIG. 7.

FIG. 7 shows the seventh embodiment of the invention which is such a condom 30 with a substantially triangular cross-section (see FIG. 7a). The condom 30 has circumferential microtubules 10, longitudinal microtubules 8, and an inflation compartment 12 just as the first embodiment of the invention does, and it is applied and inflated by methods completely the same as the first embodiment of the invention. Although a maximum lateral pressure on the penis of a user for a given air pressure or other amount of constricting force will be achieved by this embodiment, some users may prefer the looser fit of a conventional cylindrical condom and the consequent lower lateral pressure offered by the first six embodiments of the invention, based it upon the personal comfort of the user.

Figures 8, 8A:
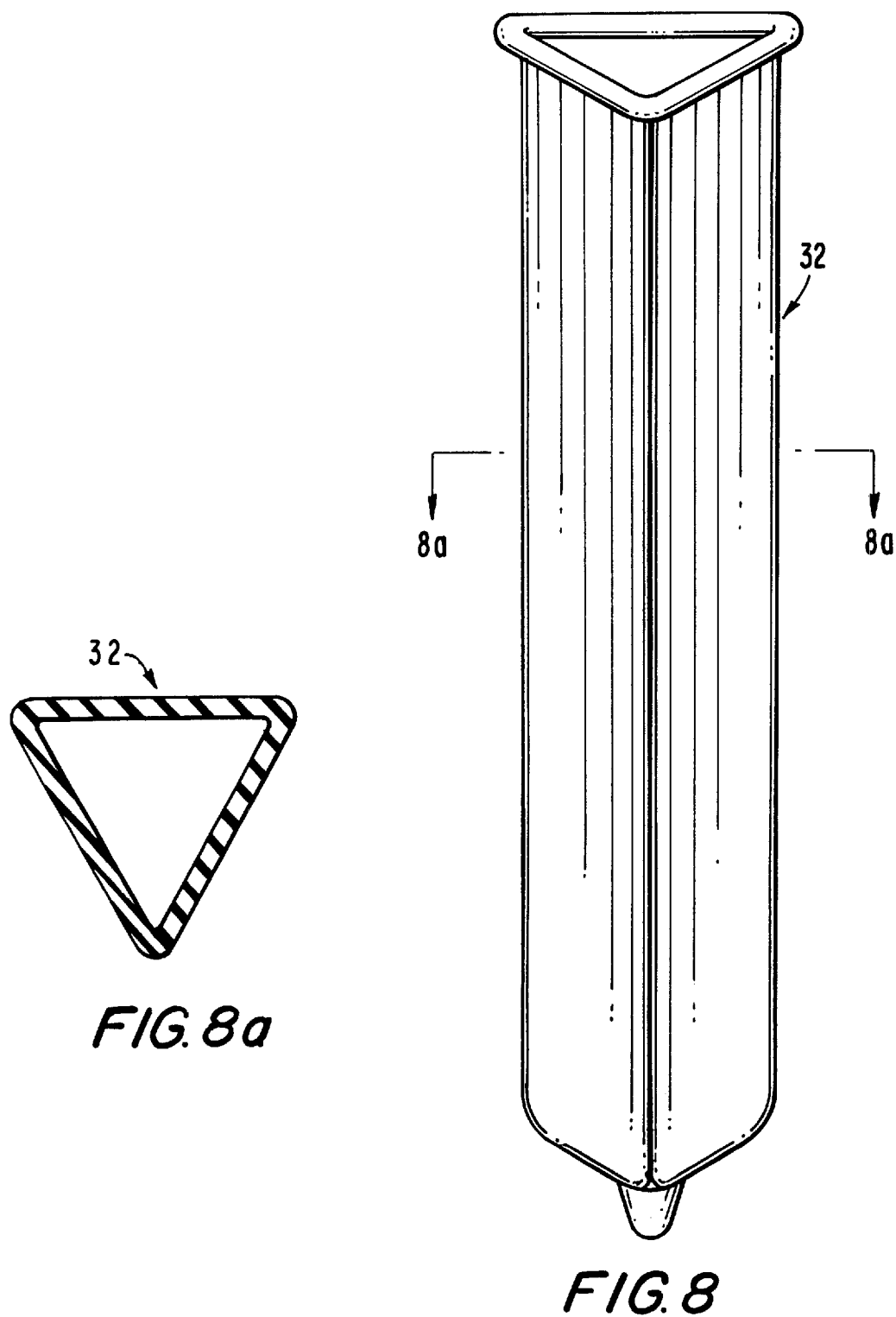
FIG. 8 is a perspective view of an eighth embodiment of the invention.
FIG. 8a is a sectional view of FIG. 8 taken along section lines 8a—8a in FIG. 8.

FIG. 8 shows the eighth embodiment of the invention which is a conventional condom except that the condom 32 shown has a substantially triangular cross-section (see FIG. 8a). This condom 32 exerts greater lateral pressure on the erect penis of a user than does a conventional condom, due to a tighter fit as previously explained.

Figure 9A:
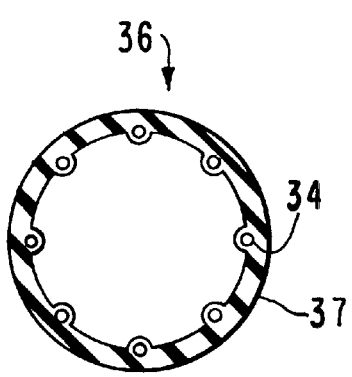
FIG. 9a is a sectional view of FIG. 9 taken along lines 9a—9a in FIG. 9.
Figure 9:
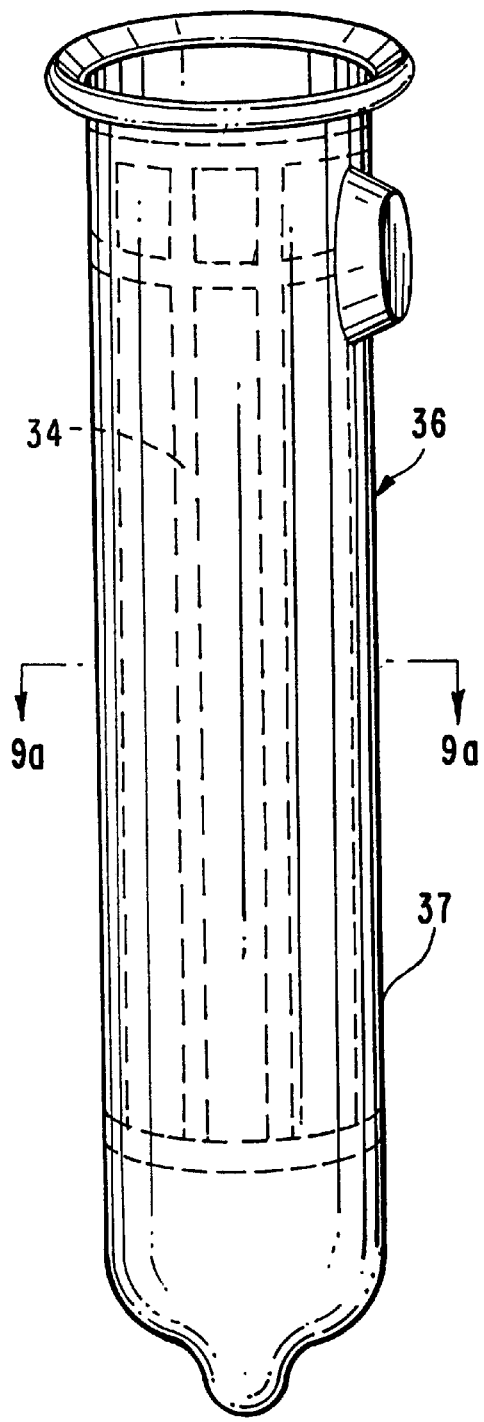
FIG. 9 is a perspective view of a ninth embodiment of the invention.

FIG. 9 shows the ninth embodiment of the invention. The sole difference form the first embodiment is that, instead of the walls of the microtubules causing a protrusion on the exterior of the membrane 4 when the condom 2 is applied to the penis as shown in FIGS. 1 and 1a, the central axis of the microtubules 34 is located such that the walls of the microtubules 34 cause a protrusion on the interior of the membrane 37 contacting the penis when the condom 36 is applied to the penis, but such walls of the microtubules 34 cause no protrusion on the exterior of the membrane 37.

The first embodiment of the invention distributes, the lateral pressure it applies to the penis in a relatively uniform and unconcentrated fashion since the microtubules 6 are on the opposite side of the membrane 4 from the side of the membrane 4 contacting the penis when the condom 2 is applied. In contrast, the first embodiment applies more concentrated pressure to the wall of the vagina than to the penis when the condom 2 is applied to the penis and is within the vagina. The pressure is exerted along the linear network which the walls of the microtubules 6 form on the exterior of the membrane 4.

The ninth embodiment of the invention reverses the nature of the pressure applied to the penis and the vagina when compared to the first embodiment of the invention. The ninth embodiment of the invention distributes the lateral pressure it applies to the wall of the vagina in a relatively uniform and unconcentrated fashion when the condom is within the vagina since the microtubules 34 are on the opposite side of the membrane 37 from the side of the membrane 37 contacting the vagina when the condom 36 is applied to the penis and is within the vagina. In contrast, the ninth embodiment applies more concentrated pressure to the penis than to the wall of the vagina when the condom 36. is applied to the penis and is within the vagina. The pressure is exerted along the linear network which the walls of the microtubules 34 form on the interior of the membrane 37.

Although not shown explicitly in the drawings, it may easily be conceived that the embodiments depicted in FIGS. 2, 3, and 7 may be varied in a manner analogous to the difference between the first and ninth embodiments of the invention. In other words, the microtubules shown in FIGS. 2, 3, and 7 may easily be transferred from their position causing protrusions on the exterior of the condom when it is applied to the penis to a position causing protrusions on the interior of the condom with similar changes in the resulting respective lateral pressure distributions on the penis and the vagina to those outlined above in the comparison of the ninth and first embodiment of the invention.

Figure 10A:
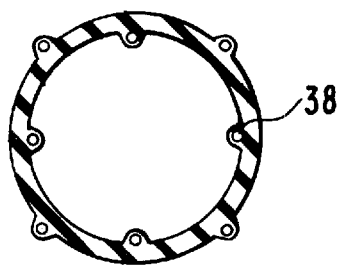
FIG. 10a is a sectional view of FIG. 10 taken along lines 10a—10a in FIG. 10.
Figure 10B:
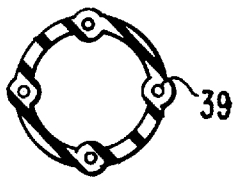
FIG. 10b is a sectional view showing a first alternate arrangement of the microtubules in the tenth embodiment of the invention.
Figure 10C:
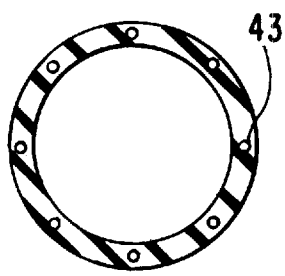
FIG. 10c is a sectional view showing a second alternate arrangement of the microtubules in the tenth embodiment of the invention.
Figure 10:
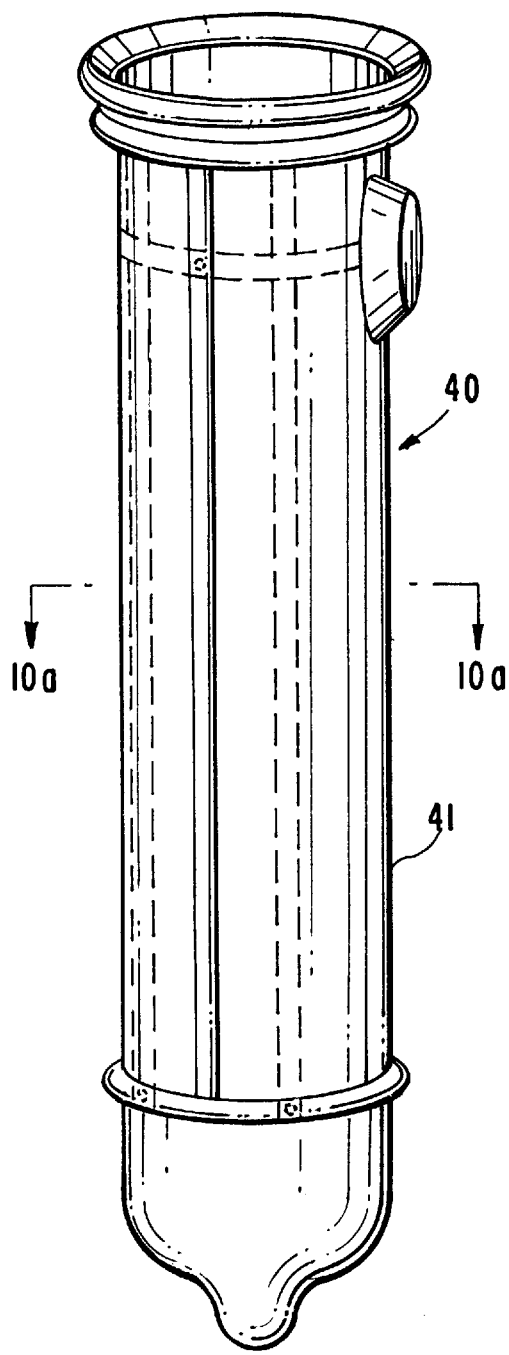
FIG. 10 is a perspective view of a tenth embodiment of the invention.

FIG. 10 shows the tenth embodiment of the invention. The sole difference from the ninth embodiment of the invention is that, instead of the microtubules causing protrusions solely on the interior of the membrane 37 as shown in FIGS. 9 and 9a, the microtubules 38 cause protrusions on both the interior and the exterior walls of the membrane 41 of the condom 40. This arrangement of microtubules 38, staggered between those microtubules 38 causing protrusions solely on the interior wall of the membrane 41 of the condom 40 and those microtubules causing protrusions solely on the exterior wall of the membrane 41 of the condom 40, has the effect of producing both regions of concentrated pressure and regions of relatively uniform and unconcentrated pressure on both the penis when the condom is applied to the erect penis and on the vagina when the penis with the condom applied is inserted into the vagina. Although FIGS. 10 and 10a show a single layer condom 40 having microtubules 38 integrally formed on both the interior and exterior walls of the membrane 41, it may become necessary or desirable from a manufacturing or production standpoint to produce a two or more layered condom membrane for ease of fabricating the microtubules 38 so that they are positioned on the interior and the exterior of the membrane 41.

FIG. 10b shows a cross-section of a microtubule 39 arrangement which also causes protrusions on both the interior and exterior walls of the membrane of the condom. It differs from the microtubule 38 arrangement in FIGS. 10 and 10a since all microtubules 39 cause protrusions on both the interior and exterior walls of the membrane of the condom, whereas, in FIGS. 10 and 10a some of the microtubules 38 cause protrusions solely on the interior wall of the membrane of the condom, and the remaining microtubules 38 cause protrusions solely on the exterior wall of the condom. The lateral pressure distributions on the penis and the vagina produced by the arrangement shown in FIG. 10b, in contrast to those produced by the arrangement shown in FIGS. 10 and 10a, are characterized by regions of concentrated pressure on both the penis and the vagina due to the protrusions on the interior and the exterior of the wall of the membrane of the condom contacting both the penis and the vagina.

FIG. 10c shows a cross-section of a microtubule 43 arrangement which differs from the microtubule 38, 39 arrangements in FIGS. 10, 10a, and 10b since none of the microtubules 43 cause protrusions on either the interior or exterior walls of the membrane of the condom, whereas, in FIGS. 10, 10a, and 10b, each of the microtubules 38, 39 cause protrusions on the interior wall of the membrane of the condom, on the exterior wall of the membrane of the condom, or on both the interior and exterior walls of the membrane of the condom. The lateral pressure distributions on the penis and the vagina produced by the arrangement shown in FIG. 10c are characterized by regions of relatively uniform and unconcentrated pressure on both the penis when the condom is applied to the erect penis and on the vagina when the penis with the condom applied is inserted into the vagina, when compared to the pressure concentrations caused on the penis, on the vagina, or on both the penis and the vagina by the presence of protrusions on the walls of the membrane of the condom as shown in the arrangements of FIGS. 10, 10a, and 10b.

Although not explicitly shown in the drawings, it may easily be conceived that the embodiments depicted in FIGS. 2, 3, and 7 may be varied in a manner analogous to the difference between the first and the tenth embodiments of the invention. Thus, a portion of the microtubules may be transferred from their position causing protrusions on the exterior wall of the membrane of the condom when it is applied to the penis to a position causing protrusions on the interior wall of the membrane of the condom. Alternatively, the microtubules may be transferred from their position causing protrusions on the exterior wall of the membrane of the condom to a position causing protrusions on the exterior and interior walls of the membrane of the condom. As yet another alternative, the microtubules may be transferred from their position causing protrusions on the exterior wall of the membrane of the condom to a position causing no protrusions on either of the exterior or interior walls of the membrane of the condom. Each of these alternative variations in the embodiments depicted in FIGS. 2, 3, and 7 will cause changes in the resulting respective lateral pressure distributions on the penis and the vagina conforming to those outlined above in the description of the tenth embodiment of the invention.

Figure 11D:
FIG. 11d is a sectional view of FIG. 11 taken along lines 11d—11d in FIG. 11.
Figure 11E:
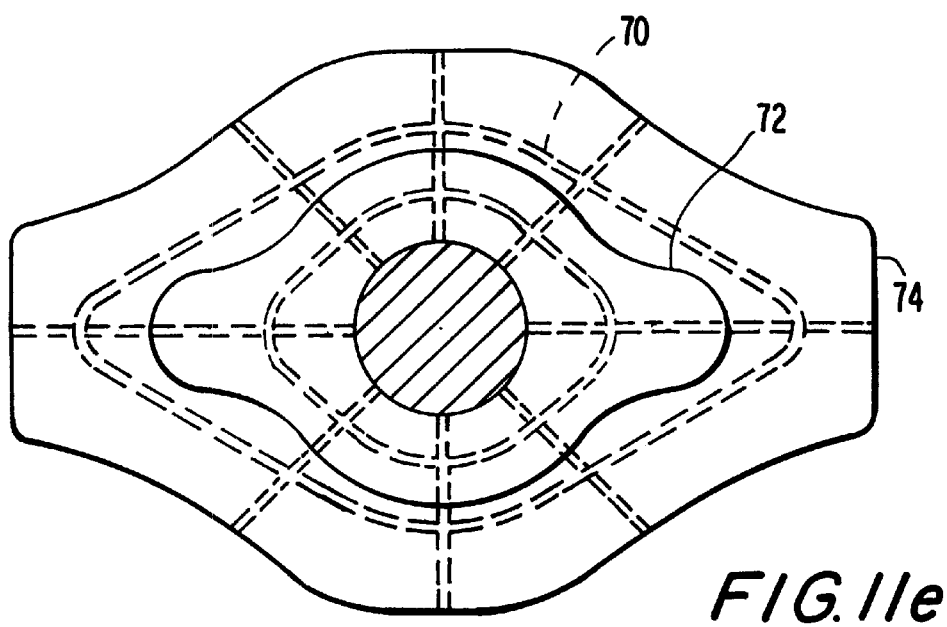
FIG. 11e is a plan view of the eleventh embodiment of the invention showing an upper lip, an optional membrane extension to the upper lip in an unrolled condition, and an optional network of microtubules in the membrane extension.
Figure 11F:
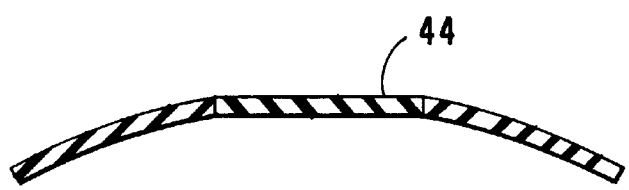
FIG. 11f is a sectional view of FIG. 11 taken along lines 11f—11f in FIG. 11.

FIG. 11 shows an eleventh embodiment of the invention which differs from the first embodiment in two respects. First, the eleventh embodiment shows a condom 42 which has an enlarged semi-rigid lip 44 curved in a convex manner with respect to the central axis 47 of the tubular membrane 49 of the condom 42 (see FIG. 11f), preferably of greater thickness than the walls of the remainder of the condom 42 with rounded protrusions 46 at each end so that the overall shape of the border 68 of the lip 44 approximates the shape of the labia majora of a woman, while the convex curvature approximates the convex curvature of the labia majora, also known as the labia majora pudendi, which can be seen when a cross-section is taken of the female pelvis, see *Anatomy of the Human Body*, ibid., p. 1322, FIG. 17–59.

Second, the eleventh embodiment is not applied to an erect penis as a conventional male condom is. FIG. 11a shows the process of application. The lip 44 is grasped by the user and pulled in the direction shown by the arrows 48 over his erect penis 50 so that his penis 50 contacts and extends the planar portion 52 of the rolled up condom corresponding to the closed end 53 of the extended condom 42, thereby causing the portion of the condom which forms two rolls 54 to unroll in a counterclockwise direction as indicated by the arrows 56. An example of the process by which this condom can be rolled up is shown in Reddy, U.S. Pat. No. 4,993,431, see FIGS. 9 and 10, and column 5, line 61–column 6, line 2.

In contrast, a conventional male condom and indeed all ten embodiments of the invention previously described are applied to an erect penis 58 as shown in FIG. 11b. The flat surface 60 of the rolled up condom is placed on the tip 62 of the penis 58 and the condom is applied by unrolling the rolls 64 of the condom in a clockwise direction as indicated by the arrows 66, thereby causing the condom to unroll over the penis from the 58 from the tip to the base.

The presence of the lip 44 will provide an additional contraceptive and prophylactic effect over the previous embodiments. The lip 46 will fit substantially over the labia majora of the female upon full insertion of the penis into the vagina which should substantially improve the barrier between the base of the penis and the female genital area over that provided by a conventional condom, thus reducing the chance for any exchange of body fluids.

Optionally, this enhanced prophylactic and contraceptive effect may be improved still further by extending the lip 44 with a membrane 66 rolled up at the edge of the lip 44 upon initial application of the condom, (see FIGS. 11c and 11d), but designed to be unrolled to cover further areas outside the labia majora of a woman. Depending on the degree of protection desired, the membrane 66 may be dimensioned to cover any combination of the pubic region and part of the lower abdomen, the right groin, the left groin, the right inner thigh, the left inner thigh, and the perineum and the anus of a woman. In general, varying radial dimension of the membrane 66 when unrolled from the border 68 of the lip 44 will be necessary to provide the degree of protection desired.

As yet a further optional enhancement of the prophylactic and contraceptive effect of the lip 44 and membrane 66, the microtubule network present in the condom may be extended into the lip 44 and the membrane 66. FIG. 11e shows such a microtubule network 70 present on a lip 72 and an unrolled membrane 74. The microtubule network 70 is placed on the surface of the lip 72 and the membrane 74 which is opposite the surface contacting a woman when the lip is seated on the labia majora of the woman. Thus when air or another expansive substance is introduced into the network, the lip 72 and the membrane 74 are pressed against the woman's skin, tending to provide a seal between the lip 72 and the skin and the membrane 74 and the skin. This tendency to form a seal furnishes extra protection against seepage of body fluids between a man and a woman.

The presence of the lip 44 which will normally be seated against the labia majora during intercourse increases the probability that the condom 42 will remain in the vagina after withdrawal of the penis from the vagina since it may tend to act in a way analogous to an anchor causing the condom 42 to remain in the vagina when the normally flaccid penis is withdrawn.

Although not explicitly shown in the drawings, the lip 44 shown in the eleventh embodiment along with the optional enhancements of the membrane 66 and the microtubule network 70 may easily be conceived as a possible addition to the embodiments shown in FIGS. 2, 3, 7, 9, and 10. It should also be noted that the eleventh embodiment of the invention, although not ideally suited in its design for the female anatomy (see the description of the twelfth embodiment of the invention below), can be inserted by a woman in her vagina prior to intercourse by the methods to be described below in connection with the twelfth embodiment of the invention, instead of a man applying it on his erect penis as previously described.

FIG. 12 shows a twelfth embodiment of the invention. The embodiment is a condom 76 which is designed to be initially inserted by a woman in her vagina prior to intercourse. FIG. 12 shows the condom as it would appear in a woman's vagina immediately prior to intercourse with its microtubules filled with air or another expansive substance. It differs from the prior ten embodiments, which comprised condoms designed to be applied by a man prior to intercourse and from the eleventh embodiment which comprised a condom primarily designed to be applied by a man prior to intercourse, in several respects.

First, the membrane 78 of the condom 76 slopes outward in the region 80 near the open end 82 of the condom 76, thus producing a tube of increasing diameter as one progresses from the end of the region 80 nearest the closed end 83 of the condom 76 to the open end 82. The outward sloping membrane 78 is designed to more closely conform the condom 76 to the vestibule of the vagina and the pudendal cleft outside of the vaginal orifice after the microtubules in the condom 76 are inflated than would be possible with a conventional condom of constant diametrical dimension. In the vestibule of the vagina and in the pudendal cleft outside of the vaginal orifice, the vaginal orifice also being known anatomically as the orificium vaginae, the interior surfaces of the walls bounding those regions when viewed in cross-section generally form curvilinear surfaces opening outward from each other, see *Anatomy of the Human Body,* ibid., pp. 1322, 1331, FIGS. 17–59, 17–64. In contrast, the tubular membrane in the first eleven embodiments of the invention was of constant diameter, reflecting the essentially constant diametrical dimension of an erect penis. It should be noted that, although not explicitly shown in the drawings, a more truly hermaphroditic condom may be conceived where the internal diameter of a tube may be held constant throughout conforming to an erect penis, while the exterior diameter of the tube may be varied to be similar to the outward sloping quality of the tubular membrane 78 in the region 80 conforming to the outward sloping of the walls of the the regions outside of the vaginal orifice. However, this would require fabrication of a tube of nonuniform thickness which would probably be semi-rigid, and this may be undesirable or otherwise not feasible from the standpoint of manufacturing difficulty or expense.

Second, the open end 82 of the condom 76 has, surrounding the perimeter of the opening and attached to the tubular membrane 78 of the condom 76, a ring 84 of spring plastic or metal having indentations 86 or other means for lockably holding the ring 84 at various positions, the indentations 86 being located across the thickness of the ring 84 at opposite sides of the ring 84 or the other means for lockably holding the ring 84 also being located at opposite sides of the ring 84. The indentations 86 or other means for lockably holding the ring 84 allow the open end 82 of the condom 76 to be opened or closed by a female wearer at will. The condom 76, upon initial removal from its packaging, will be disposed so that ring 84 forms a circular or generally elliptical member. However, after the condom 76 is inserted into the vagina, the female user exerts pressure 88 on the indentations 86, (see FIG. 12a), or otherwise releases the other means for lockably holding the ring 84 so that the ring 84 forms a closed linear member, (shown in dotted lines in FIG. 12a). This operation will close the normally open end 82 of the condom 76 and afford protection against unwanted intercourse or undesired and possibly harmful foreign substances entering the condom 76. Immediately before desired intercourse, the woman exerts inward pressure 92 on the indentations 86 or otherwise engages the other means to lockably hold the ring 84 to reestablish the curved open profile of the ring 84 and thus reopen the normally open end 82 of the condom 76.

Third, an air source or source of another expansive substance 94 to fill the microtubules is located on an outer semi-rigid lip 96 which is similar to the lip 44 in the eleventh embodiment, the lip 96 also preferably approximating the shape and curvature of the labia majora of a woman. The expansive substance source 94 is located on one of the protrusions 98. This location makes it convenient for the female user to activate the expansive substance source 94 immediately before intercourse. A location of the expansive substance source 94 on the tubular membrane 78 may be inconvenient for activation once the condom 76 is inserted into the vagina. For instance, if the expansive substance source 94 were located adjacent to the closed end 83 of the condom 76, the activation of the expansive substance source 94 would require the withdrawal of the condom 76 from the vagina if the condom 76 was already inserted in the vagina.

In contrast, the expansive substance source for the previous eleven embodiments has no particular preferable location as any location on the condom is easily accessible to a man once the condom is applied to his penis. This, of course, assumes that the expansive substance source is not located toward the closed end of the condom, and the man does not wish to activate it once his penis is inserted into the vagina of a woman. If it is anticipated that activation of the expansive substance source on a male condom is likely to be desired after insertion of the penis into the vagina, then, indeed, the expansive substance source should preferably be located close enough to the open end of the condom such that even upon full insertion of the penis into the vagina, the expansive substance source will be located outside of the female genital area.

The expansive substance source 94 will be designed to only allow inflation of the condom 76 to a degree that does not place a woman wearer in risk of injury or discomfort either from rupture of the microtubules or excessive pressure on the vaginal wall due to overinflation of the condom 76.

Fourth, the condom 76 has a relief valve 100 located on the other protrusion 98 not occupied by the expansive substance source 94. The relief valve 100 is designed to allow the condom 76 to be deflated after intercourse, assuming that it remains in the vagina, so that it can easily be removed from the vagina. The location again is convenient for a woman to simply press the relief valve 100 after intercourse to deflate the condom 76. The relief valve 100 should preferably also be designed so that partial deflation of the condom 76 is possible in the event that a woman wearer suffers discomfort upon fulll inflation of the condom 76.

Fifth, the condom 76 may be produced having an arrangement of microtubules incorporated into it designed to increase the probability that the penis will withdraw the condom 76 from the vagina after intercourse even though the penis is partially or wholly flaccid, thus obviating the need for a woman to remove the condom from her vagina after intercourse using the relief valve 100, as previously described. Specifically, there may be numerous longitudinal microtubules 102 placed on the interior surface of the tubular membrane 78 and at least one circumferential microtubule 104 on the interior surface of tubular membrane 78 in the middle region of the tubular membrane 78. These internal microtubules when inflated will tend to press against an erect penis during intercourse establishing a bond between the erect penis and the condom through the mutual pressure exerted against each other by the erect penis and the microtubules. Although the penis on withdrawal may be partially or wholly flaccid and, thus, not capable of generating the frictional resistance against relative movement of the condom 76 that an erect penis would produce, it may be anticipated that the residual frictional resistance to and the inertia resisting relative movement of the condom with respect to the wholly or partially flaccid penis may be sufficient to allow the condom to be wholly withdrawn with the penis after intercourse, thus overcoming the frictional resistance which may be developed between the condom and the vagina during the withdrawal of the penis which would tend to keep the condom in the vagina.

To further this end, the mechanism for retaining the condom in the vagina during sexual intercourse should be the minimum necessary to retain the condom in the vagina during intercourse, while not frustrating the aim of withdrawal of the condom by the penis after intercourse. One mechanism of retaining the condom in the vagina during intercourse is the provision of circumferential microtubules 106 on the exterior of the tubular membrane 78. The number of these circumferential microtubules 106 should be a low proportion of the number of internal longitudinal and circumferential microtubules so as to maximize the probability that the condom will be withdrawn from the vagina by the penis, even if partially or wholly flaccid, after intercourse, while still retaining the condom in the vagina during intercourse.

The provision of the internal microtubules has the additional consequence of improving the male erection by the same method described in connection with the first eleven embodiments. The external microtubules, when inflated, will press against the vaginal wall and thereby increase the frictional resistance generated by the vaginal wall when the condom attempts to move during intercourse over that present if such microtubules were not inflated. This increased frictional resistance will tend to keep the condom in place in the vagina during intercourse. Moreover, the external microtubules, by increasing frictional forces generated between the condom and the vagina during intercourse when the condom attempts to move will produce the additional consequence of increasing stimulation and pleasure to the woman during intercourse.

Figure 12C:
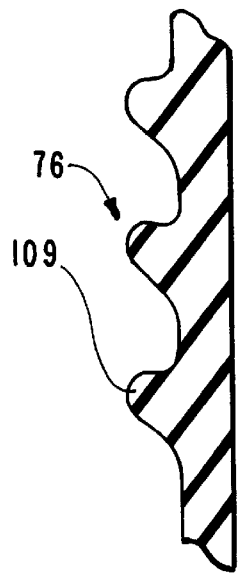
FIG. 12c is a partial cross-sectional enlarged detail of the length of the condom membrane showing optional external circumferential knobbed ridges on that membrane.
Figure 12D:
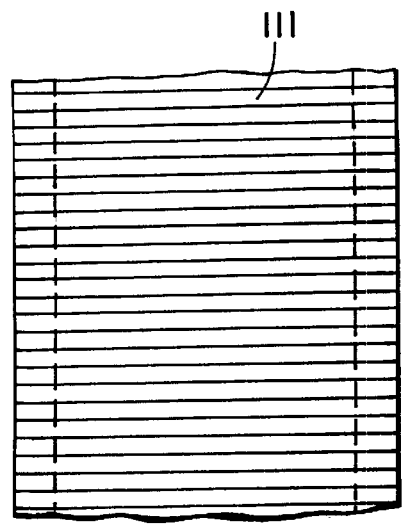
FIG. 12d is a partial enlarged detail of the length of the condom membrane showing an example of optional external texturing of that membrane.

In order to increase the probability that the condom 76 will be withdrawn by the penis from the vagina after intercourse, a circumferential protuberance 108 producing a constriction of the interior diameter of the tubular membrane 78 can be optionally introduced, (see FIG. 12b). Of course, the presence, of the internal circumferential microtubules 104 will naturally decrease the diameter of the condom 76 by the portion of the microtubule extending within the interior wall of the tubular membrane 78, but a constriction of the diameter of the interior wall beyond that produced by the internal circumferential microtubules 104 will be even more effective in grasping the penis.. For maximum effectiveness, the protuberance 108 should be placed outside the region 80 where the tubular membrane 78 slopes outwards as outside this region 80, the tubular membrane 78 will have a minimum internal diameter even before the protuberance 108 is introduced. The protuberance 108 should preferably be made of elastic material which is the same as that of the tubular membrane 78, but preferably thicker than it so that it bends to permit the insertion of the penis but presses on the inserted penis to retain it once inserted. As yet another optional feature to increase the probability that the condom will be withdrawn by the penis from the vagina after intercourse, circumferential knobbed ridges or texturing could be introduced along the length of the internal wall of the condom similar to the ridges or texturing described below on pages 51–52 of this application, (see also FIGS. 12c, 12d).

The condom 76 can be one layer or multilayered made from one of the materials and by one of the processes previously described. As was true with the eleventh embodiment of the invention where a membrane 66 and microtubule network 70 enhanced the contraceptive and prophylactic effect of the lip 44, the lip 96 may optionally be extended with a similar membrane and a similar microtubule network may be placed in the membrane.

Figures 13, 13A, 13B:
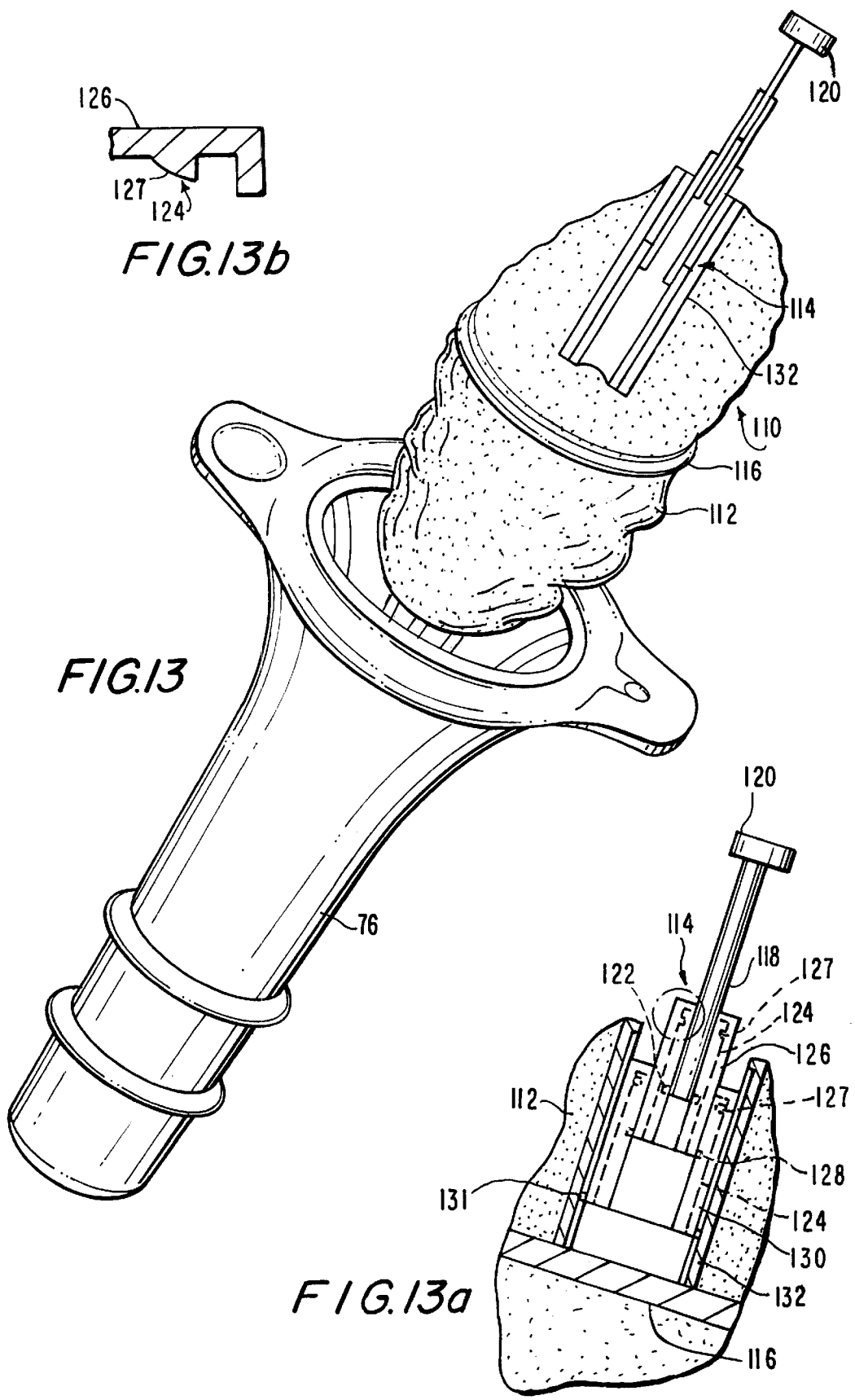

FIG. 13 shows an exemplary method of inserting the condom 76 into the vagina. The condom 76. The condom 76 is shown in the fully extended position. A condom applicator 110 is used which comprises a fibrous element 112 with an ellipsoid shape made of a natural or synthetic substance capable of retaining moisture such as cotton. The fibrous element 112 may be impregnated with spermicide or another prophylactic or contraceptive substance to coat the condom 76 if the condom 76 is not already so coated. It may also be impregnated with a lubricant to coat the condom 76 to ease the insertion of the penis into the condom 76 during intercourse. The fibrous element 112 is carried on a telescoping handle 114 which is attached to a disk 116 to which the fibrous element 112 is in turn attached.

The telescoping handle 114 is detailed in cross-section in FIG. 13a in a partially retracted state. The telescoping handle 114 comprises a central rod 118 to which a grip 120 is attached. The central rod 118 has two projections 122 at an end which move in tracks 124 within a cylindrical outward telescoping section 126. The tracks 124 have flexible locking stops 127 adjacent to their end to enable the projections 122 to travel past the stops 127 while the central rod 118 is extending, but the stops 127 offer resistance to travel of the projections 122 in the opposite direction once the projections 122 travel past the stops 127. The tracks 124 end immediately beyond the locking stops 127, thereby preventing further extension of the central rod 118. The combination of the stops 127 and the end of the tracks 124 cause the projections 122 and, thus, the central rod 118 to be locked against any retraction or extension, (a FIG. 13b). The telescoping section 126 has two projections 128 moving within tracks 124 within a second cylindrical outward telescoping section 130 and the tracks 124 also have flexible locking stops 127, with the tracks 124 ending immediately beyond the locking stops 127. The movement of the telescoping section 126 and its locking by the combination of the stops 127 and the end of the tracks 124 is analogous to the movement and locking of the central rod 118 described above.

For the sake of simplicity, FIG. 13a shows only two outward telescoping sections 126, 130. However, it should be understood that a sufficient number of telescoping sections will be provided between the two telescoping sections shown 126, 130, of similar construction to the two telescoping sections shown 126, 130, to allow the extension of the fibrous element 112 for a sufficient length so that the longest dimension of the vaginal wall maybe traversed by the fibrous element, see ibid., p. 1329. The outermost telescoping section 130 is contained within a cylindrical guide 132 which is attached to the disk 116 to which the fibrous element 112 is also attached. The cylindrical guide 132 has similar tracks and flexible locking stops to those found in telescoping sections 126, 130, and telescoping section 130 has two projections 131 similar to those found in central rod 118 and telescoping section 126. The projections 131 are controlled in their movement by the tracks and flexible locking stops in the cylindrical guide 132 in a manner similar to the control of the movement of the projections 122, 128 by the tracks and flexible locking stops in the telescoping sections 126, 130 described above.

The resistance to travel of the projections in the retracting direction offered by each set of the flexible locking stops must be sufficient to allow the telescoping handle 114 to remain in a locked position while the telescoping handle 114 is being used to insert the condom 76 into the vagina. However, the resistance of the telescoping handle to retraction when at least one telescoping section is fully extended and locked must not be so great that the user cannot collapse it outside of the vagina upon exertion of a reasonable effort.

As the sections of the telescoping handle 110 are extended, the telescoping handle 110 forms an approximately conical profile with the base of the cone furthest from the grip 120. This profile affords increasing bending strength of the handle with increasing distance from the grip 120. This should help to prevent the handle from possibly breaking at a section deep within the vagina if a force normal to the axis of the handle is exerted on the handle while the handle is fully extended in the vagina.

In practice in order to insert the condom 76 into her vagina, a woman user of the condom 76 will first fully or partially extend the telescoping handle 114 into a locked position, depending on the distance into her vagina that the condom 76 is desired to be inserted. Then the woman user will position the unextended condom 76, which will appear in cross-section similar to the condom 42 shown in FIG. 11a, such that the central closed end 83 is generally over her vaginal orifice. The fibrous element 112 is then positioned over the central closed end 83 of the condom 76 and the telescoping handle 114 is pressed forward causing the closed end 83 of the condom 76 to be pressed between the labia majora and through the pudendal cleft, between the labia minora and through the vestibule of the vagina, and through the vaginal orifice into the vagina, and, if so desired, pressed through the vagina until the closed end 83 of the condom 76, at maximum, reaches the cervix or otherwise reaches a maximum extension, thereby fully extending the tubular membrane 78 of the condom 76. As the closed end 83 of the condom 76 is being pressed through the pudendal cleft, the outer lip 96 of the condom 76 contacts and is firmly seated against the labia majora. Alternatively, the tubular membrane 78 of the condom 76 may be only partially extended by the condom applicator 110 so that the closed end 83 of the condom 76 remains in the middle region of the vagina. Some female users may desire such an alternative because of discomfort or irritation which may be experienced if the tubular membrane 78 of the condom 76 remains fully extended in the vagina for an appreciable length of time. In any event, the extension of the tubular membrane 78 must be sufficient to prevent the condom from being dislodged from the vagina during normal movement. The seating of the outer lip 96 on the labia majora should aid in the secure insertion of the condom 76 and minimize the necessary extension of the tubular membrane 78 into the vagina in order to achieve such secure insertion, thus reducing the possibility of discomfort caused by the presence of the condom 76 in the vagina for an extended period of time. This discussion, of course, assumes that there is some extension of the tubular membrane 78 that will prevent the tubular membrane 78 from being dislodged from the vagina during normal movement. If this is not true, inflation of the microtubules on the condom 76 or other means may be necessary to prevent dislodgement of the tubular membrane 78 from the vagina during normal movement.

After the tubular membrane 78 of the condom 76 has reached the desired full or partial extension in the vagina and after the outer lip 96 is firmly seated on the labia majora, the woman wearer will preferably then exert outward pressure 88 on the indentations 86 or otherwise release the other means for lockably holding the ring 84 so that the ring 84 forms a closed linear member, as previously described. At some later time, immediately before desired intercourse, the woman exerts inward pressure 92 on the indentations 86 or otherwise engages the other means for lockably holding the ring 84 to reestablish the circular or genarally elliptical shape of the ring 84, again as previously described. In addition, as previously described, the female user will activate the expansive substance source 94 immediately before intercourse. The condom 76 will be designed to withstand, without rupture of any portion of the condom 76, the axial and shear stresses exerted by an inserted and perhaps rapidly moving erect penis, whether the condom 76 is partially or fully extended into the vagina at the time of insertion and whether or not the expansive substance source 94 is activated.

Figure 14:
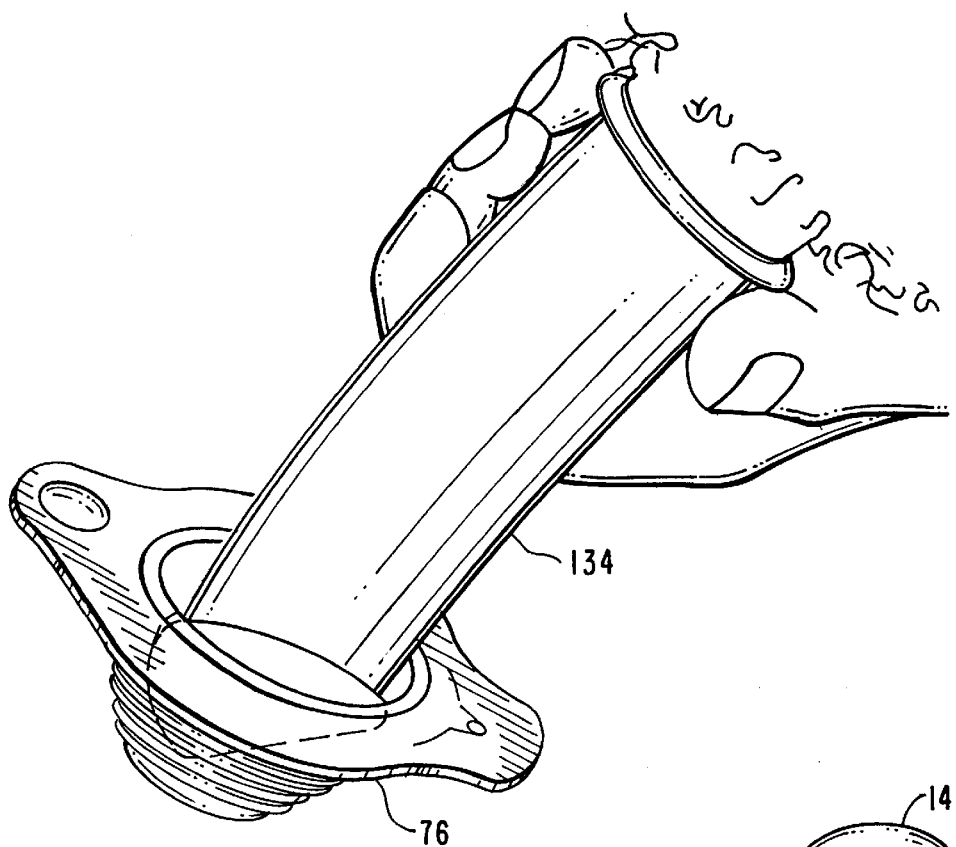
FIG. 14 is a perspective view of an erect penis being used to apply the twelfth embodiment of the invention.

FIG. 14 shows the process of completing the extension of the tubular membrane 78 by an erect penis 134 when the tubular membrane 78 is initially only partially extended into the vagina. Although FIG. 14 shows a male condom applied to the penis 134, it is to be understood that such a condom is a matter of extra protection only and need not be used. In the case when an erect penis is used to complete the insertion of the condom 76 into the vagina, the expansive substance source 94 should preferably be activated by the woman after full extension of the tubular membrane 78 into her vagina to minimize any possible risk of rupture of the microtubules.

When the penis is first withdrawn from the vagina after its insertion, the condom 76 may or may not be withdrawn with it, but the invention's microtubules are to be designed with the object of minimizing the possibility that the condom will be partially withdrawn from the vagina by the penis, but will not stay on the penis. Even in such a worst case event, the likelihood of exchange of body fluids is minimized by the position of the open end 82 of the condom 76 facing away from the female genital area. In the event that the condom stays firmly inserted in the vagina after the penis is first withdrawn, it will remain there if further sexual intercourse is desired immediately. Of course, the woman also has the option of activating the relief valve 100, which will deflate the condom, and removing the condom 76 from her vagina, as previously described. If the condom is withdrawn by the penis, the necessity of the female activating the relief valve 100 to remove the condom 76 from her vagina is obviated as previously noted.

However, this discussion assumes that the man does not remove the condom 76 from his penis after initial withdrawal of his penis from the vagina and attempt further unprotected sexual intercourse which would defeat the object of giving the woman control over contraception and prophylaxis. If such an eventuality is to be feared, the condom 76 may be redesigned to minimize the probability that the condom 76 will be withdrawn from the vagina by the penis. A possible design for achieving this end is to increase the number of external circumferential microtubules 106 and their pressure exerting capacity and adding external longitudinal microtubules to the condom so that the pressure exerted by the external microtubules greatly exceeds the pressure exerted by the internal circumferential microtubules 104. The internal longitudinal microtubules 102 would be removed. Indeed, the internal circumferential microtubules 104 could also be removed. Such a design essentially reverses that shown in FIG. 12 and the effect is thus reversed. Such a design may cause the pressure exerted on the wall of the vagina to be relatively so much greater than that exerted on the erect penis that a high probability exists that the condom will remain in the vagina after intercourse, no matter how many times the penis is inserted in and withdrawn from the vagina during intercourse. It is to be understood that the pressure on the wall of the vagina must be kept within safe limits and, therefore, it is to be expected that the lateral pressure on the penis will be reduced in comparison to the original design presented where the pressure on the penis was to be maximized and that on the vagina minimized to cause the condom to be withdrawn on the penis from the vagina.

An additional optional feature of the condom that would increase the probability of the condom remaining in the vagina of the woman despite repeated insertions and withdrawals of the penis during intercourse is shown in FIG. 12c. A series of circumferential knobbed ridges 109 along a portion of the length of the external wall of the condom would be oriented such that they would resist the pulling of the condom 76 out of the vagina during intercourse. However, such knobs must be carefully designed to, avoid any possibility of discomfort to the vaginal membrane during the slight reciprocations of the condom in the vagina that can be expected during intercourse and especially if the penis is repeatedly withdrawn and inserted into the condom. Alternatively to such circumferential knobbed ridges 109, a texturing pattern on a portion of the external wall of the condom could be introduced to increase the friction between the condom and the vaginal wall, thus resisting the movement of the condom out of the vagina. An example of such a texturing pattern is shown in FIG. 12, comprising a series of microridges 111 running generally perpendicular to the longitudinal axis of the condom. Other possible texturing patterns may easily be conceived. For example, a series of microridges extending diagonally and parallel to each other across the width of the condom may be placed on the external wall of the condom. As an additional example, two series of microridges may be placed on the external wall of the condom, each microridge in a particular series of microridges extending parallel to each other microridge in that series and extending diagonally across the width of the condom, the two series of microridges forming a cross hatching texturing pattern on the external wall of the condom.

Of course, if the condom remains in the vagina after intercourse, the woman will be required to remove the condom from her vagina, and the decreased lateral pressure that the man's penis will encounter during intercourse will provide less of an improvement in his erection, but the countervailing advantage is the maintenance of the woman's control over contraception and prophylaxis even in the case when the penis is inserted in and withdrawn from the vagina many times during sexual intercourse.

Figure 15:
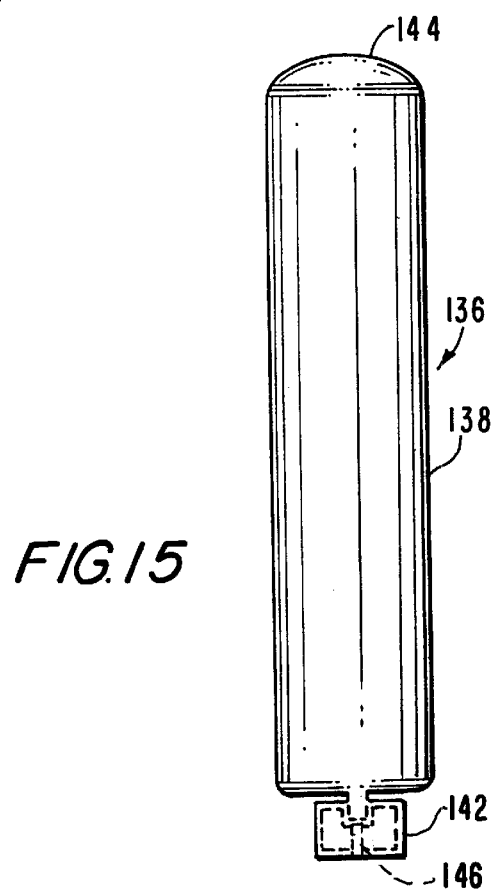
FIG. 15 is an elevation view of a second embodiment of an applicator for applying the twelfth embodiment of the invention.

An alternative condom applicator 136 is shown in FIG. 15. It comprises a cylindrical balloon 138 with a diameter of a typical condom and the same length as the telescoping handle 110 previously described. The cylindrical balloon 138 is attached at a first open end 140 to a compressed air source 142 and has a second closed end 144. FIG. 15 shows the balloon 138 fully inflated. When deflated, depending on the elasticity of the material of which it is made, which may be any flexible, elastic substance, such as rubber or other elastomers, the balloon 138 may be quite small and may be folded into a small size for packaging with the condom 76. Preferably, the woman user should be able to control the activation of the compressed air source 142 by finger release of a valve 146 in the source 142 which is normally closed, thereby inflating the balloon 138 at the rate and to the extent desired, since too rapid a rate may cause discomfort and only partial insertion of the condom 76 into the vagina may be desired. With the caveats regarding controlling the rate and extent of inflation being understood, the balloon condom applicator 136 may well be superior to the previous condom applicator 110 described from the standpoint of ease of manufacture and simplicity of use. Of course, the method of inserting the condom 76 into the vagina with the balloon applicator 136 does away with any necessity to extend and lock a telescoping handle. Instead of a fibrous element 112 pressing the condom 76 into the vagina by the advance of a telescoping handle, the balloon 138, being inflated by an air source 142 under control by a user-manipulated valve 144, presses the condom 76 into the vagina.

Figure 16:
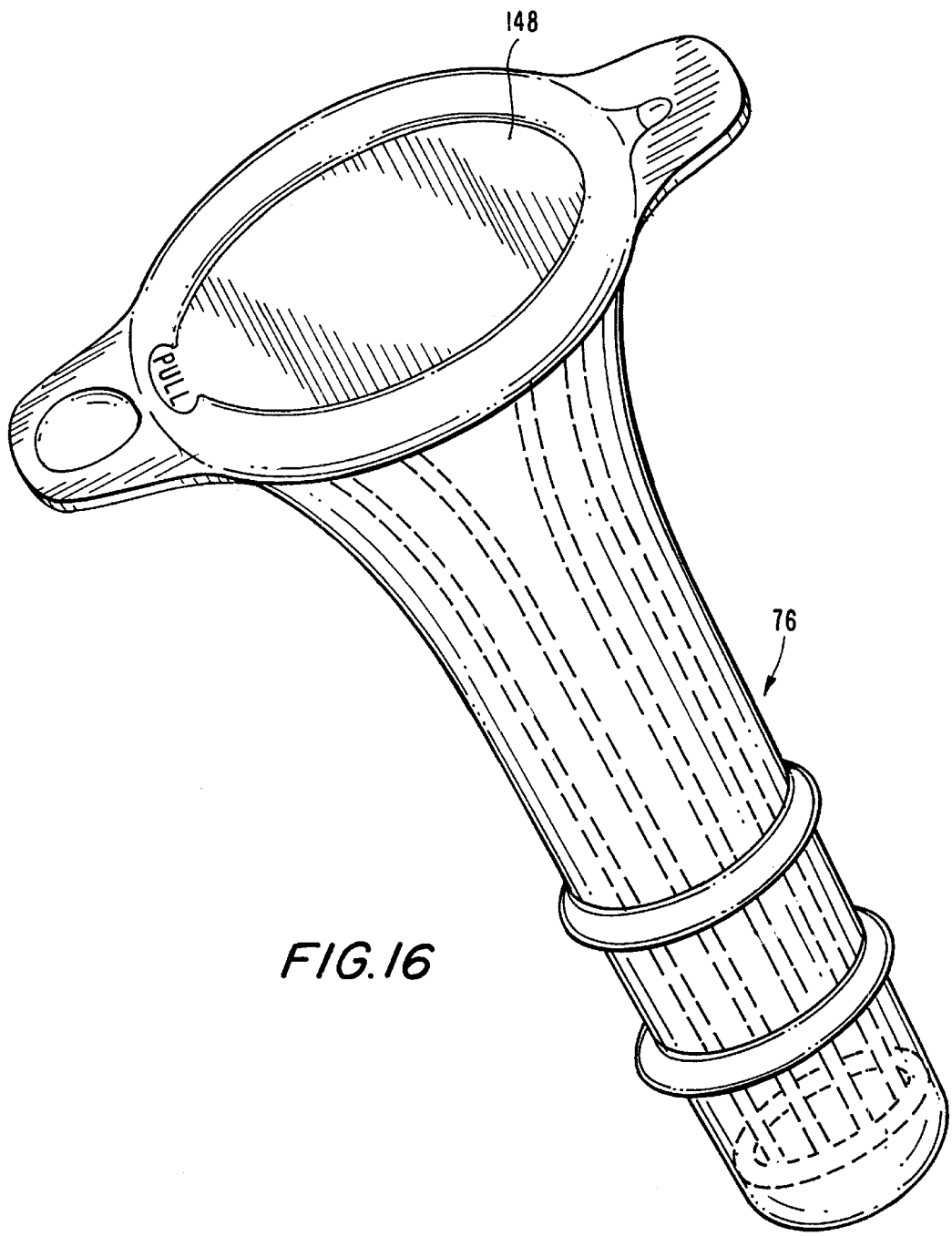
FIG. 16 is a perspective view of the twelfth embodiment of the invention with an optional seal over the normally open end.

The condom 76 may have spermicidal lubricants on the interior of the tubular membrane 78 either applied during manufacture or during insertion of the condom 76 by the fibrous element 112 or the balloon 138, as previously described. However, it is not recommended that such lubricants be applied to the outer surface of the condom 76 as such substances can increase vaginal infections, see Reddy, U.S. Pat. No. 5,325,871, column 2, lines 11–16, and article cited therein. To this end, the condom 76 may be initially sealed with a cover 148 as shown in FIG. 16 at its normally open end so that lubricant placed in the interior of the condom 76 will not be permitted to migrate to the outer surface after manufacture and prior to use. Of course, this strategem assumes that such lubricants are applied during manufacture. If, however, they are applied during insertion of the condom in the vagina, then care must be exercised to keep the fibrous element away from the outer surface of the condom and the vaginal area.

Figure 17:
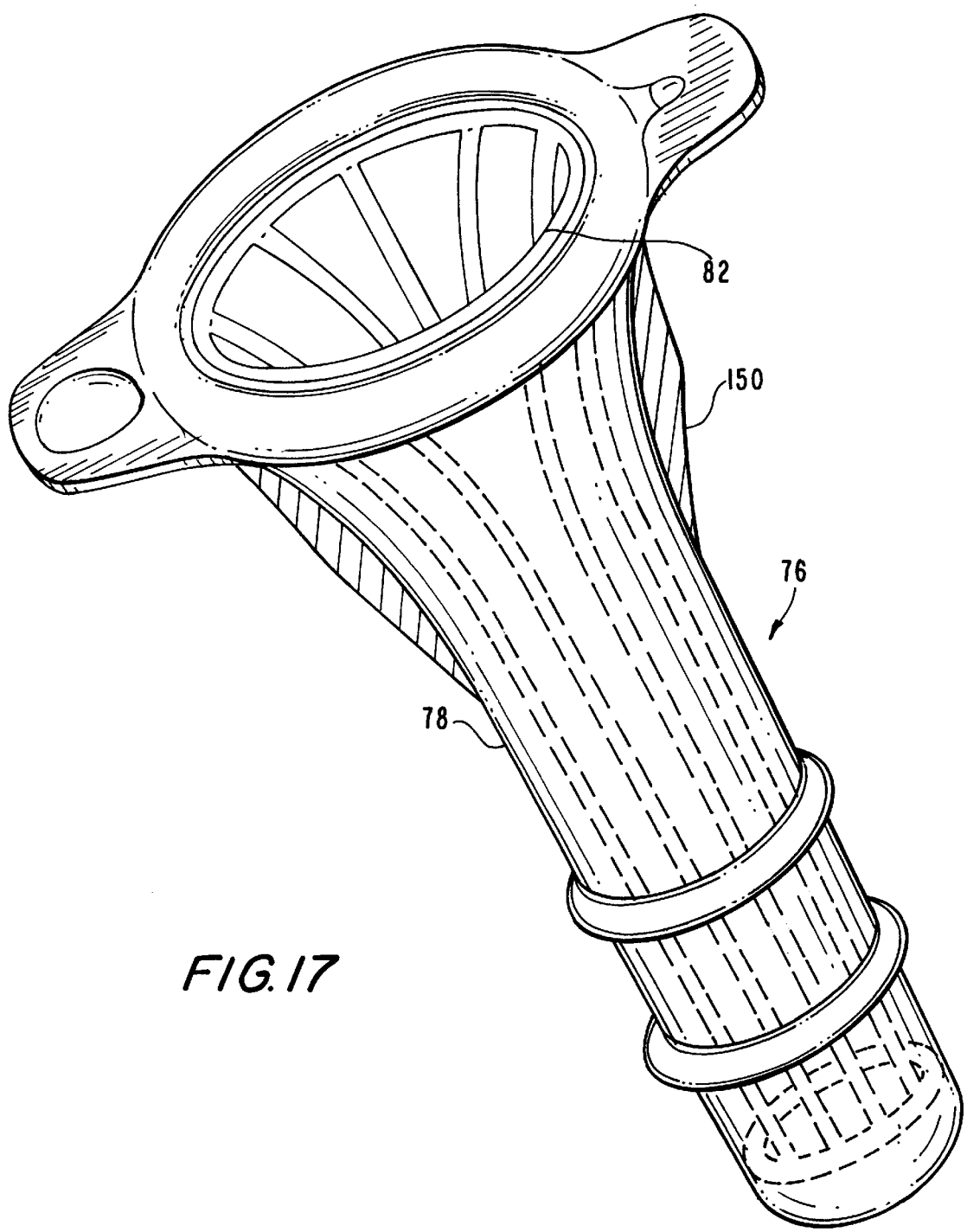
FIG. 17 is a perspective view of the twelfth embodiment of the invention with an optional thickening of the wall of the tubular membrane in the region adjacent to its open end.

FIG. 17 shows an optional variation of the condom 76. FIG. 17 shows in cross-section an increased thickness 150 of the wall of the tubular membrane 78 of the condom 76 near its open end 82. The increased thickness is designed to produce clitoral stimulation during intercourse. Although the condom 76 is designed to be substantially secure in the vagina during intercourse, slight reciprocating longitudinal movements of the condom 76 along the length of the vagina may be anticipated due to the reciprocating longitudinal movements of the penis along the length of the vagina that may normally occur during intercourse. Such slight reciprocating longitudinal movements will cause the region of increased thickness 150 to move in a like reciprocating manner against the clitoral area, producing clitoral stimulation. Alternatively, a like effect may be achieved by replacing the area of increased thickness 150 with one or more exterior circumferential microtubules 106 placed in the same area as the area of increased thickness 150, but with the tubular membrane 78 being of uniform thickness throughout.

Figure 18:
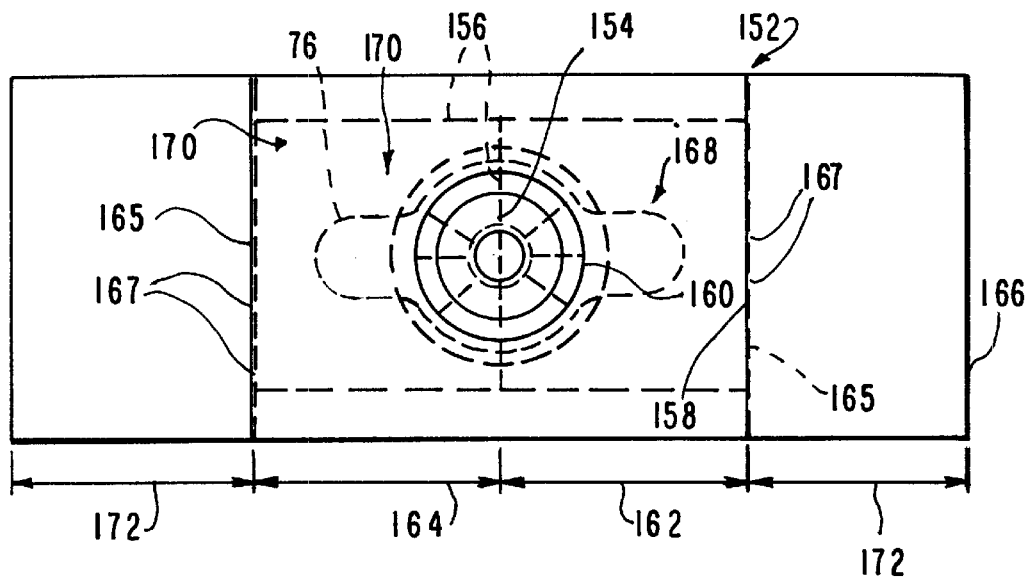
FIG. 18 is an elevation view of one embodiment of packaging for the twelfth embodiment of the invention.

An example of possible packaging for the condom 76 is shown in FIG. 18. The package shown 152, which may be comprised of an elastomeric material, a polymer, a paper material, whether impregnated with plastic or not, or a metallic foil, is only designed to hold the condom 76. The condom applicator, whether of the telescoping handle variety 110 or the balloon variety 136, will be placed in a separate package (not shown) which may or may not be enclosed within a yet larger package enclosing the condom package 152 and the condom applicator package. Two sets of perforations are shown on the condom package 152 even though they are actually on opposite sides of the package 152 and would not actually be visible in this view. (A third set of perforations, also present and actually visible in this view, will be described later.) However, this is done for the sake of clarity and as an aid in understanding the use and opening of this package 152 during insertion of the condom 76. The first set of perforations 154 is the set actually visible in the view shown. This set of perforations 154 comprises a first circular set of perforations slightly larger in radial size than the open end 82 of the condom 76 and its outer lip 96 considered without the protrusions 98. The condom 76 lies beneath this first set of perforations 154 in the package 152. The center of the first circular set of perforations substantially coincides with the center of the open end 82 of the condom 76. The first set of perforations 154 also comprise a set of perforations that emanate radially from the center of the circular set of perforations, but do not reach the radius of the circular set of perforations or the the center of the circular set of perforations. These radial perforations terminate on a second circular set of perforations also included in the first set of perforations 154. The second circular set of perforations are concentric with the first circular set of perforations, and are of lesser radius than the first circular set of perforations.

The second set of perforations 156, which are not actually visible in this view since they are on the side of the package 152 facing away from this view, comprise two parallel lines of perforations and a line of perforations between the parallel lines of perforations and substantially perpendicular to the parallel lines of perforations. The two parallel lines of perforations terminate at both ends by intersecting with folds 158 (again on the side of the package 152 facing away from this view) which are substantially perpendicular to the parallel lines of perforations and extend across the width of the package 152.

On the same side of the package 152 as the first set of perforations 154 are a set of concentric rings 160. The common center of the concentric rings 160 substantially coincides with the center of the open end 82 of the condom 76 lying beneath them. The largest diameter ring of the concentric rings 160 is of approximately the same diameter as the open end 82 of the condom 76 considered without its outer lip 96. The concentric rings 160 are formed by a photoluminescent material that is also phosphorescent. In other words, the material will become luminescent under ordinary visible light, but its luminescence will persist at least for a period of time in a darkened area. This will allow insertion of the condom 76 in the dark. Examples of such materials are zinc sulfide phosphors.

This package 152, however, acts as more than just a container for the condom 76. It facilitates a method of positioning the condom 76 while it is still in the package 152 to allow direct insertion of the condom 76 from the package 152 into the vagina in one step. It should be noted, however, the method outlined below is not as certain to achieve a successful insertion as a method entailing manually removing the condom from the package 152 by rupturing the second set of perforations 156, manually locating the vaginal orifice, and then using a condom applicator to insert the condom 76. Since the vaginal orifice is hidden beneath the labia majora and labia minora and therefore not normally externally visible, the method outlined below, which does not disturb the labia majora and the labia minora prior to insertion, will not be certain to successfully locate the vaginal orifice prior to insertion. However, its comparative ease and the reasonable probability that the condom will be successfully inserted in the vagina make it at least as desirable a method as the ordinary method involving the clumsy and possibly unsanitary manual location of the vaginal orifice.

Figure 19:
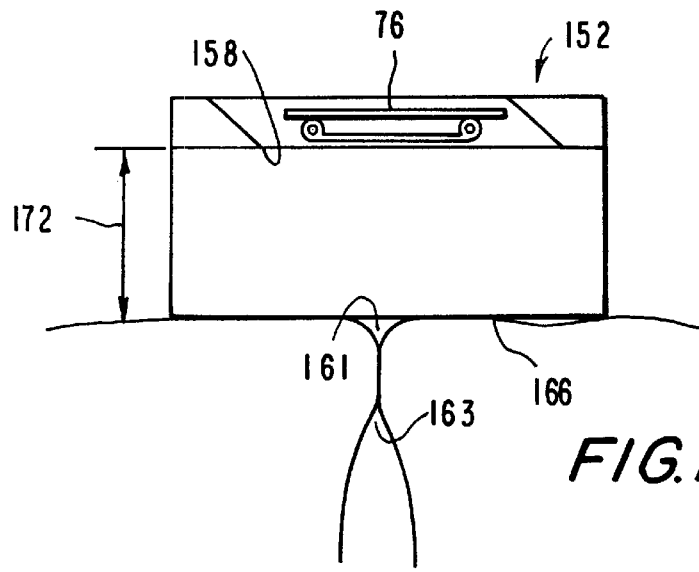
FIG. 19 is a cross-sectional view of the embodiment of packaging shown in FIG. 18 shown in a position to insert the twelfth embodiment of the invention in the vagina of a female user.

The female user first folds the package 152 at folds 158 into a channel shape, (see FIG. 19). A third set of perforations 165 directly over the folds 158 on the other side of the package 152 from the folds 158 rupture upon folding, easing the folding process. The edges 166 of the package 152 have removable strips under which are suction cups or other means removably adhering the channel to the body of the user once the correct position of the package 152 for insertion is found.

The method of insertion next involves using the concentric rings 160 as a positioning device so that the center of the innermost ring and therefore the center of the open end 82 of the condom 76 is most likely directly over the vaginal orifice. To achieve the highest probability of this occurring, the center of the innermost ring should be placed directly over the pudendal cleft 161, horizontally adjacent to the end of that cleft nearest the anus. Such a position is necessary since the vaginal orifice 163 is not symmetrically located with respect to the length of the pudendal cleft and the labia majora. Rather, the vaginal orifice is located under the portion of the pudendal cleft adjacent to the end of that cleft nearest the anus, that end of the cleft being bounded by the posterior labial commissure, see ibid, FIGS. 17–59, 17–64, pp. 1322, 1331, and p. 1330.

Since such a positioning task may be difficult for the female user, particularly in an unlighted area, the condom 76 may be positioned in the condom package 152 such that it mirrors the asymmetry of the vaginal orifice with respect to the length of the pudendal cleft and the labia majora. Furthermore, to conform to this asymmetry when the condom is inserted in the vagina and seated on the labia majora, the outer lip 96 of the condom may be designed so as to be asymmetrical with respect to the open end 82 of the condom 76. Specifically, one side of the outer lip 96 and its protrusion 98 may be substantially longer than the other side of the outer lip 96 and its protrusion 98. The condom 76 would be inserted in the vagina so that the shorter side of the outer lip 96 and its protrusion 98 would cover the portion of the labia majora nearest the anus. Such a design of the outer lip 96 would have the advantage of more closely following the actual asymmetrical arrangement of the labia majora with respect to the vaginal orifice and thus allowing firmer seating of the outer lip 96 on the labia majora after insertion.

The condom 76 would be placed asymmetrically with respect to the condom package 152 by locating the center of the open end 82 of the condom 76 and, thus, the common center of the concentric rings 160 asymmetrically with respect to the folds 158, or, in other words, the dimensions 162 and 164 may be made unequal. The female user will be able to determine the asymmetric location of the common center of the concentric rings 160 if the portions 167 of the package 152 between each perforation of the third set of perforations 165 along an imaginary line drawn through each of those perforations 165 are covered by a line of the same photoluminescent phosporescent material forming the rings 160. The photoluminescent phosphorescent material covering these portions 167 would, thus, form two broken lines visible to the female user in the dark.

The female user locates the common center of the concentric rings 160 in a position over her pudendal cleft 161, horizontally adjacent to the portion of her pudendal cleft 161 adjacent to her anus. The condom package 152 facilitates this task by its unequal dimensions 162, 164 since this task requires that the condom package 152 be so oriented that the fold 158 located by the shorter of the dimensions 162, 164 also be located adjacent to her anus. Since the vaginal orifice is located horizontally adjacent to the end of the pudendal cleft nearest the anus, there is a reasonable probability that successful insertion of the condom in the vagina will occur if the common center of the concentric rings 160 is positioned as specified above. (This reasonable probability of success, however, depends on the possibility of determining the shorter of the dimensions 162, 164 such that it reasonably approximates, for a majority of women, the distance between the anus and the vaginal orifice.)

The condom 76 will preferably be so arranged in the condom package 152 such that the shorter side of the outer lip 96 and its protrusion 98 will lie parallel to the shorter of the dimensions 162, 164 and will lie within the region bounded by the shorter of the dimensions 162, 164. If successful insertion of the condom 76 into the vagina occurs, this arrangement of the condom 76 in the condom package 152 will cause the shorter side of the outer lip 96 and its protrusion 98 to seat on the portion of the labia majora bounded by the vaginal orifice and by the end of the pudendal cleft adjacent to the anus, that portion of the labia majora being shorter than the portion of the labia majora bounded by the vaginal orifice and by the end of the pudendal cleft furthest from the anus. Such a seating of the condom 76 and its asymmetrical outer lip 96 and protrusions 98 will, thus, more closely conform to and cover the labia majora than if the condom 76 were seated such that its longer outer lip 96 and protrusion 98 were located in the position of the shorter outer lip 96 and protrusion 98 in the above described seating or if a condom 76 with a symmetrical outer lip 96 and protrusions 98 were used.

In any event, once the female user is reasonably certain that the center of the rings 160 is postioned over her vaginal orifice, the strips on the edges 166 of the package 152 are removed and the package 152 in its folded channel shape is attached to the body of the user in that position. The fibrous element 112 of the applicator 110 or the expansive substance source 146 may then be positioned so that the center of either, depending on which device is used, is centrally located over the innermost concentric ring. The fibrous element 112 is then extended or the balloon 138 is inflated so that the fibrous element 112 or the balloon 138 presses against the surface of the package 152 facing outward in FIG. 18, ruptures the first set of perforations 154, and pushes the condom 76 against the other surface of the package 152, rupturing the second set of perforations 156. The second set of perforations when ruptured, however, form two "trap doors" 168, 170 which rotate about the folds 158 acting as hinges. The trap doors 168, 170 thus rotate out of the path of the condom 76 being pushed toward the female genital area. As the outer lip 96 and protrusions 98 of the condom 76 reach the labia majora, they seat themselves on it and stop.

The separated circular piece of the package 152, formed by the rupture of the first set of perforations 154, has been carried thus far between the applicator and the condom 76. However, since the radius of the circular piece of package 152 is greater than the radius of the outer lip 96 of the condom 76 considered without the protrusions 98 as previously stated, the circular piece should seat itself on the outer lip 96. However, the ruptured radial perforations in the first set of perforations 154 will open forming a plurality of trapeziodal shaped pieces which will be pushed aside, allowing the condom applicator to pass through the open end 82 of the condom 76, contact the closed end 83 of the condom 76, and insert it into the vagina as far as desired, as previously described. The trapeziodal shape of the pieces formed by the ruptured radial perforations should reduce the risk of them tearing the condom as they are pushed aside, when contrasted to triangular shapes which would be formed if the radial perforations had reached the center of the first circular set of perforations instead of terminating on the second set of circular perforations. The closed end 83 should preferably be made thicker than the remaining walls of the condom 76 to further reduce any risk of tearing upon insertion. Furthermore, the radial perforations do not reach the radius of the, first circular set of perforations, causing the trapeziodal pieces formed upon rupture of the radial perforations to remain attached to the separated circular piece of package 152 and not be carried into the condom 76 upon insertion. In order to prevent the small circular piece of package 152 formed by the rupture of the second circular set of perforations from being carried into the condom 76 upon insertion, the woman will be required to pause momentarily in the insertion process to remove it after the trapezoidal shaped pieces have formed.

The package 152 should preferably be designed such that the dimensions 172 from the folds 158 to the edges 166 are at least equal to the greater of dimensions 162, 164. This design will allow trap doors 168, 170 to swing freely out of the way of the condom 76 being inserted without striking the body of the female user and possibly causing injury, as can readily be conceived by consulting FIG. 19 showing the package 152 attached to the body of the female user prior to insertion of the condom 76. Of course, if due to incorrect placement of the package 152, the condom 76 is not successfully inserted, manual location of the vaginal orifice and subsequent insertion can always be undertaken. It should be noted that since the method of insertion of the condom 76 directly from the package 152 must always involve some uncertainty as to the location of the vaginal orifice and a possibility of pressing the condom against some other portion of the body with the risk of possible discomfort, gentle and slow application of pressure to any condom applicator should always be used in any attempted insertion by this method to minimize the risk of any mishap.

Figure 20:
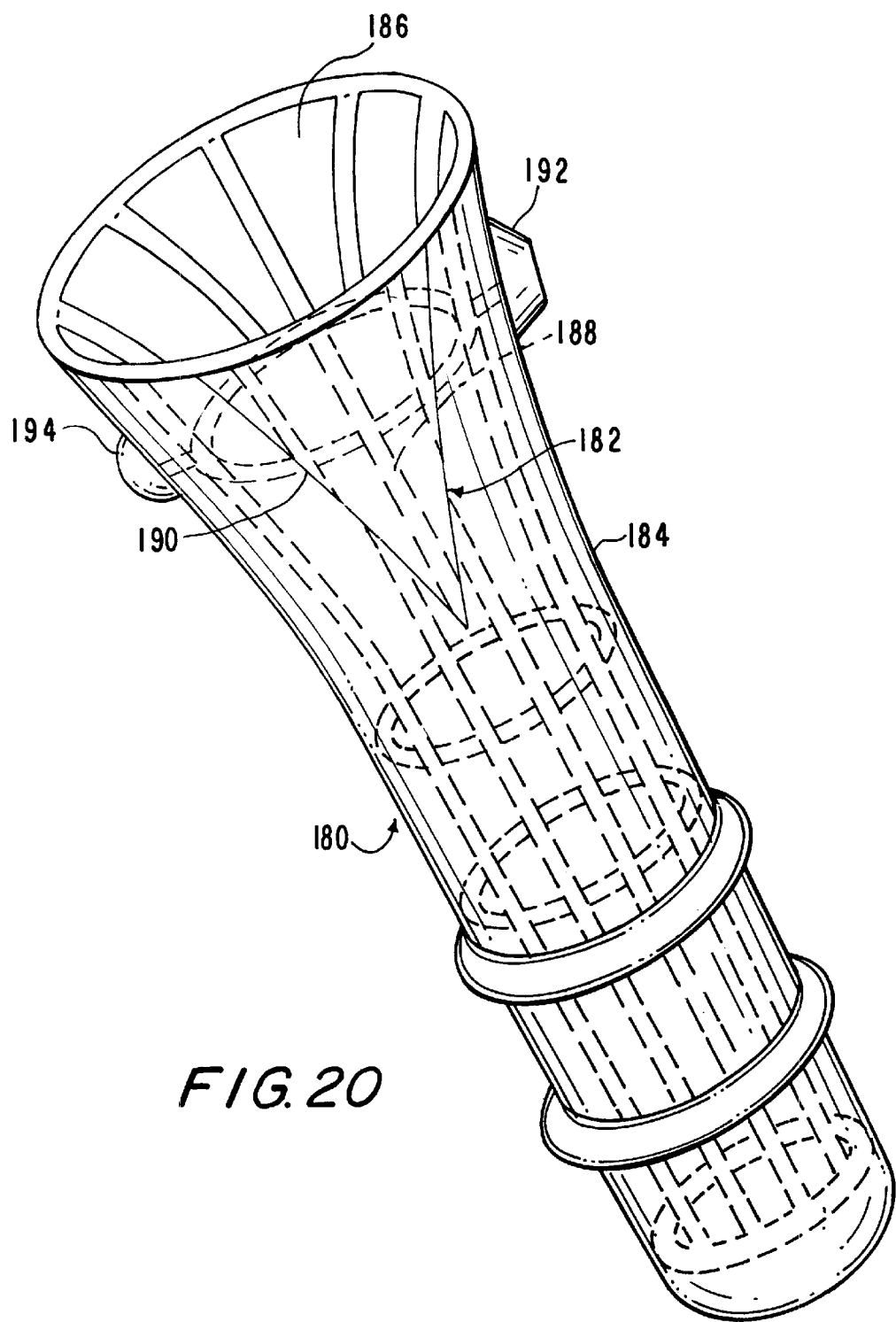
FIG. 20 is a perspective view of a thirteenth embodiment of the invention.

FIG. 20 shows a thirteenth embodiment of the invention. It differs from the twelfth embodiment of the invention in several respects.

First, the condom 180 has at least one pleat 182 running along at least some length of the tubular membrane 184 of the condom 180. The pleat 182 begins at the open end 186 of the condom 180, and continues for a depth along the length of the condom 180 to be selected by the condom manufacturer. The pleat 182 functions to allow a variation in the cross-sectional perimeter of the condom 180 in the region closest to its open end 186. This permitted variation in the cross-sectional perimeter is meant to further allow the condom 180 to conform to the variations in the interior surfaces of the female anatomy in the region of the pudendal cleft and the vestibule of the vagina than would be possible in the twelfth embodiment of the invention where no such pleat is present. The pleat 182 is shown to be triangular, narrowing as it progresses down the length of the condom 180 to take account of the assumption that the need to accomodate the variable surfaces of the vestibule and the pudendal cleft will be lessened and become unnecessary once the comparatively uniform tubular region of the vagina is reached. However, the depth of the pleat 182 may be expanded up to the full length of the condom 180 should the result of use by women indicate the necessity for such a design.

Second, the condom 180, unlike the twelfth embodiment of the invention, has no outer semi-rigid lip as does the twelfth embodiment of the invention since such a lip could not easily be pleated, if it could be pleated, at all. The absence of this lip will, of course, remove the securing effect gained by the lip seating on the labia majora of the female user. However, the loss of this particular securing effect should be compensated for by the closer circumferential fit that should be achieved between the membrane 184 of the condom 180 and the female genital area when compared to the fit available for the twelfth embodiment of the invention. This closer circumferential fit will be due to the adjustment of the circumference of the condom occurring as a result of the presence of the at least one pleat 182 in the membrane 184. The pleat 182 will expand the circumference of the condom 180 as the microtubules 188 within the region of the membrane 184 bordered by the folds 190 of the pleat 182 are inflated until the pleat folds 190 completely flatten out or the outer pleat surface contacts the wall of the vagina or of the region it outside of the vagina. This "self-adjusting" effect should secure the condom in the vagina, despite the complex and variable geometry of the region exterior to the vagina.

If despite this "self-adjusting" effect, the secure seating of the condom in the vagina proves to be a problem, an alternative to an outer semi-rigid lip that could be pleated, yet would seat on the labia majora, could be provided. For instance, the tubular membrane itself could be formed on its open end as a flap of the approximate shape and size of the outer semi-rigid lip with a fold forming the border between the flap and the main body of the tubular membrane. Since the flap would be of the same nonrigid material as the tubular membrane in order for pleats to be formed, removable attachment means, such as suction cups, could be provided to attach the flap to the labia majora.

Since no outer semi-rigid lip exists in this embodiment, an inflation compartment 192 and relief valve 194 for the inflation and deflation, respectively, of the condom 180 are shown installed on the membrane 184 of the condom 182 instead of on the outer semi-rigid lip as shown in the twelfth embodiment of the invention. The inflation compartment 192 and relief valve 194 should preferably be installed close enough to the open end 186 of the condom 180 to allow these to be conveniently activated when the condom 180 is fully inserted into the vagina. For this purpose, the condom 180 should be of such length that, when fully inserted in the vagina, it extends a sufficient distance beyond the labia majora to allow the installation of the inflation compartment 192 and the relief valve 194 at positions on the membrane 184 also beyond the labia majora.

Figure 21:
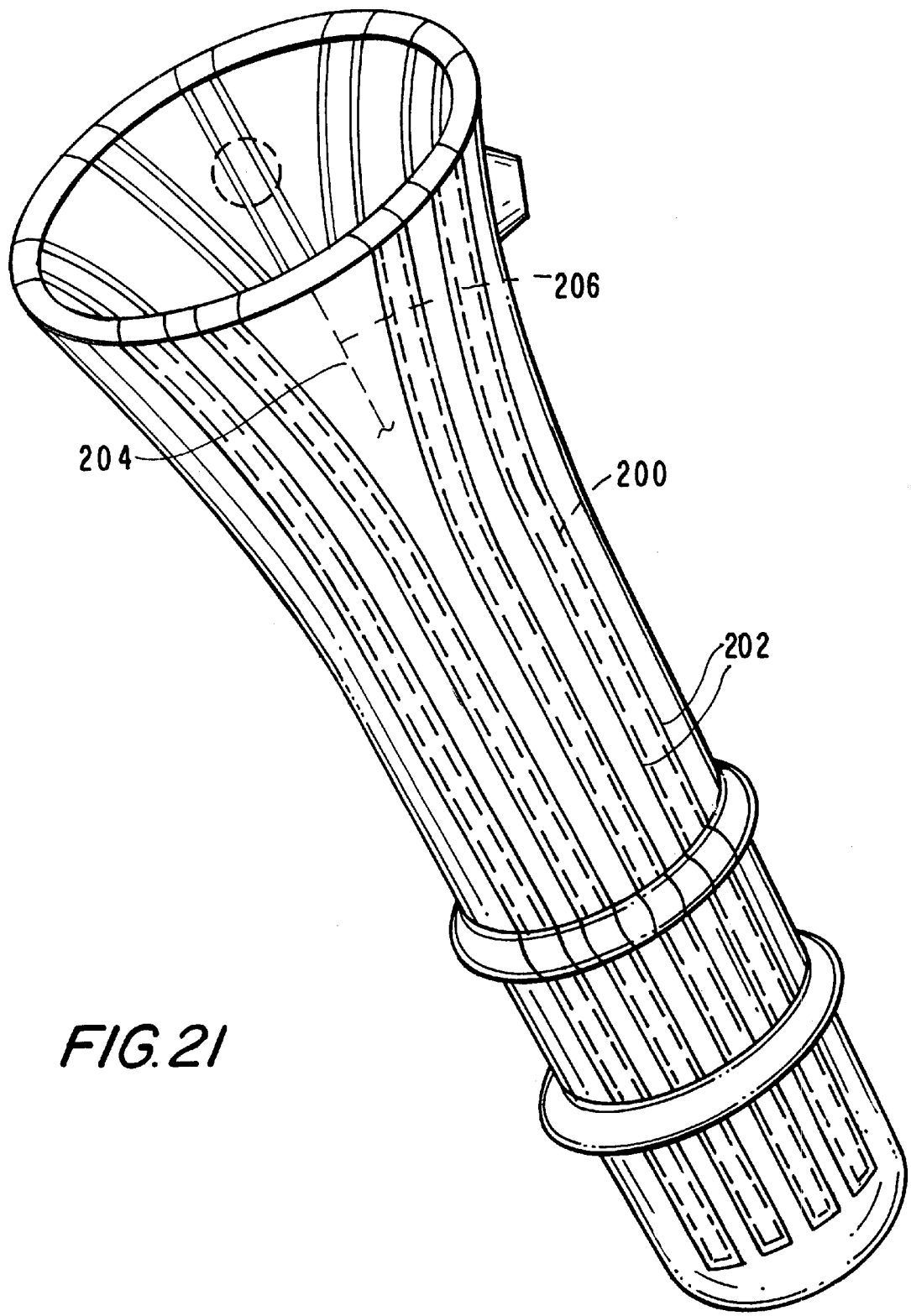
FIG. 21 is a perspective view of a fourteenth embodiment of the invention.

FIG. 21 shows a fourteenth embodiment of the invention. It differs from the thirteenth embodiment of the invention in that instead of at least one conical shaped pleat enclosing some of the longitudinal microtubules and extending a variable distance from the open end of the condom, each longitudinal microtubule 200 is enclosed on either side by its own pair of pleats 202 extending down the entire length of the longitudinal microtubule 202. This greatly increases the number and length of pleats which in turn greatly increases the circumferential adjustability of the condom and the length of the condom over which such adjustment may be made. Although FIG. 21 shows pleats 202 only around each longitudinal microtubule and limited by the number of such longitudinal microtubules 202, it is certainly possible to place additional pleats in the membrane 204 between each adjacent pair of longitudinal microtubules to increase such circumferential adjustability even further (a dotted line 206 indicates such an optional pleat). Of course, the longitudinal microtubules 202 maybe located so closely together that there is no membrane 204 between each adjacent pair of longitudinal microtubules in which to place additional pleats. The depth and number of pleats is only limited by the circumference or length of the cross-sectional perimeter of the condom and the length of that perimeter occupied by the longitudinal microtubules 200. Thus, the adjustability of the female condom can be varied by varying the circumference or length of the cross-sectional perimeter of the condom, the number of longitudinal microtubules 200, and the depth and number of pleats.

Figure 22:
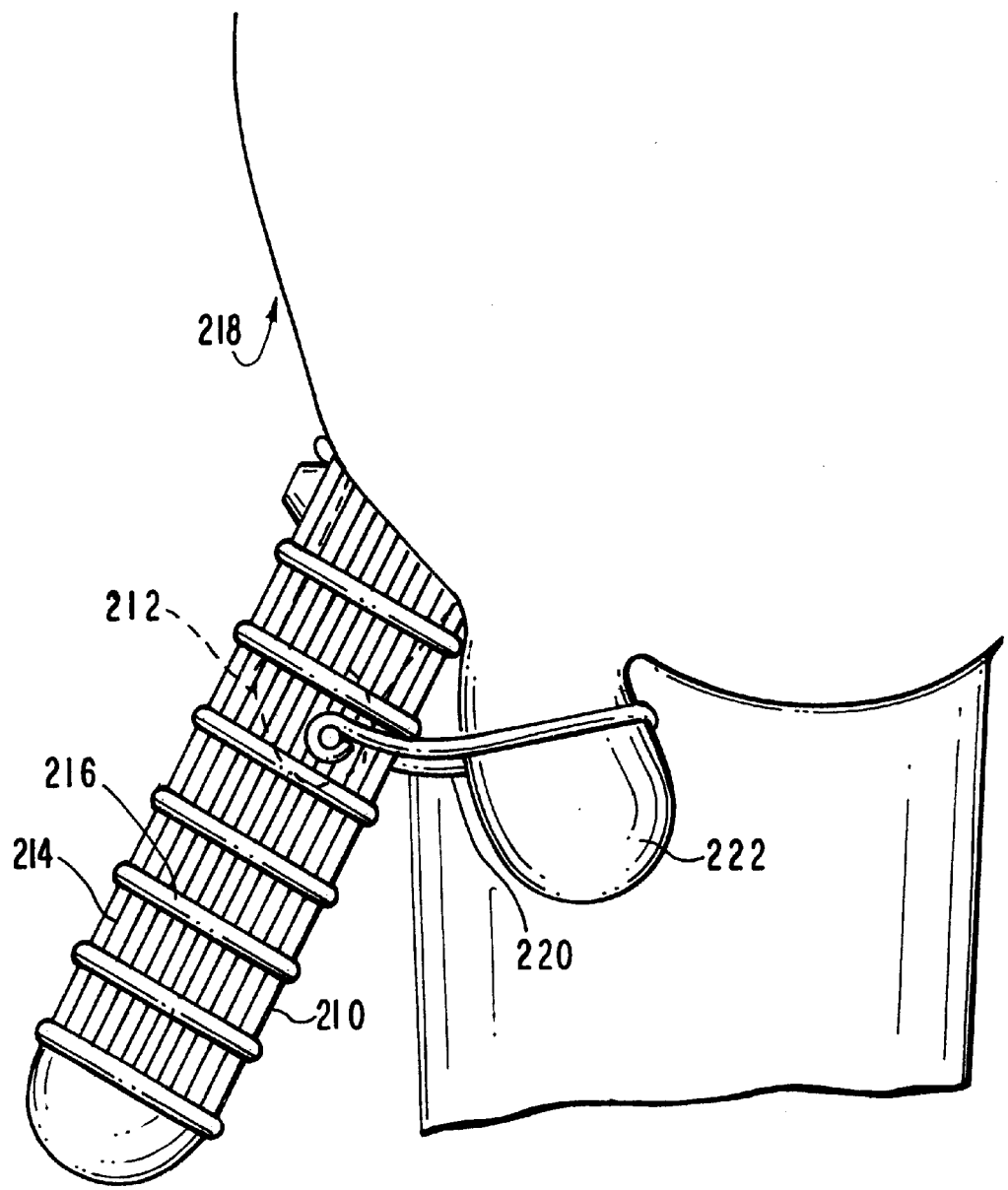
FIG. 22 is an elevation view of a fifteenth embodiment of the invention as worn on a male user.

FIG. 22 shows a fifteenth embodiment of the invention. A male condom 210, similar to the first eleven embodiments of the invention, is shown on the flaccid or partially erect penis 212 of a user. The male condom 210 is similar to the first eleven embodiments of the invention in that it too has longitudinal microtubules 214 and circumferential microtubules 216. It differs from the first eleven embodiments of the invention in that it does not assume application on a fully erect penis as do the first eleven embodiments and conventional condoms. In fact, it is designed to simulate an erect penis for a user whose penis is flaccid or partially erect, despite any effort by the user to achieve an erection. To this end, the condom 210 is provided, in general, with many more longitudinal microtubules and circumferential microtubules than the first eleven embodiments. These microtubules when expanded will thus simulate an erect penis by forming a stiff cylindrical structure. It may be necessary to place so many longitudinal microtubules on the condom to achieve the required rigidity that they abut each other and this possibile structure is, in fact, depicted in FIG. 22. Similarly, although the circumferential microtubules 216 are shown in FIG. 22 separated by spaces along the length of the condom, it may also be necessary to place a sufficient number of these circumferential microtubules 216 on the condom so that they abut each other in order to achieve the necessary rigidity of the condom. The condom 210 is secured to the flaccid or partially erect penis 212 of the user by the lateral compressive pressure exerted by the inflated microtubules on the flaccid or partially erect penis 212. In addition, the condom 210 is secured to the body 218 of the user by, for example, an elastic band 220 attached to the condom 210 and adapted to be extended around the scrotum 222 of the user.

Figure 23A:
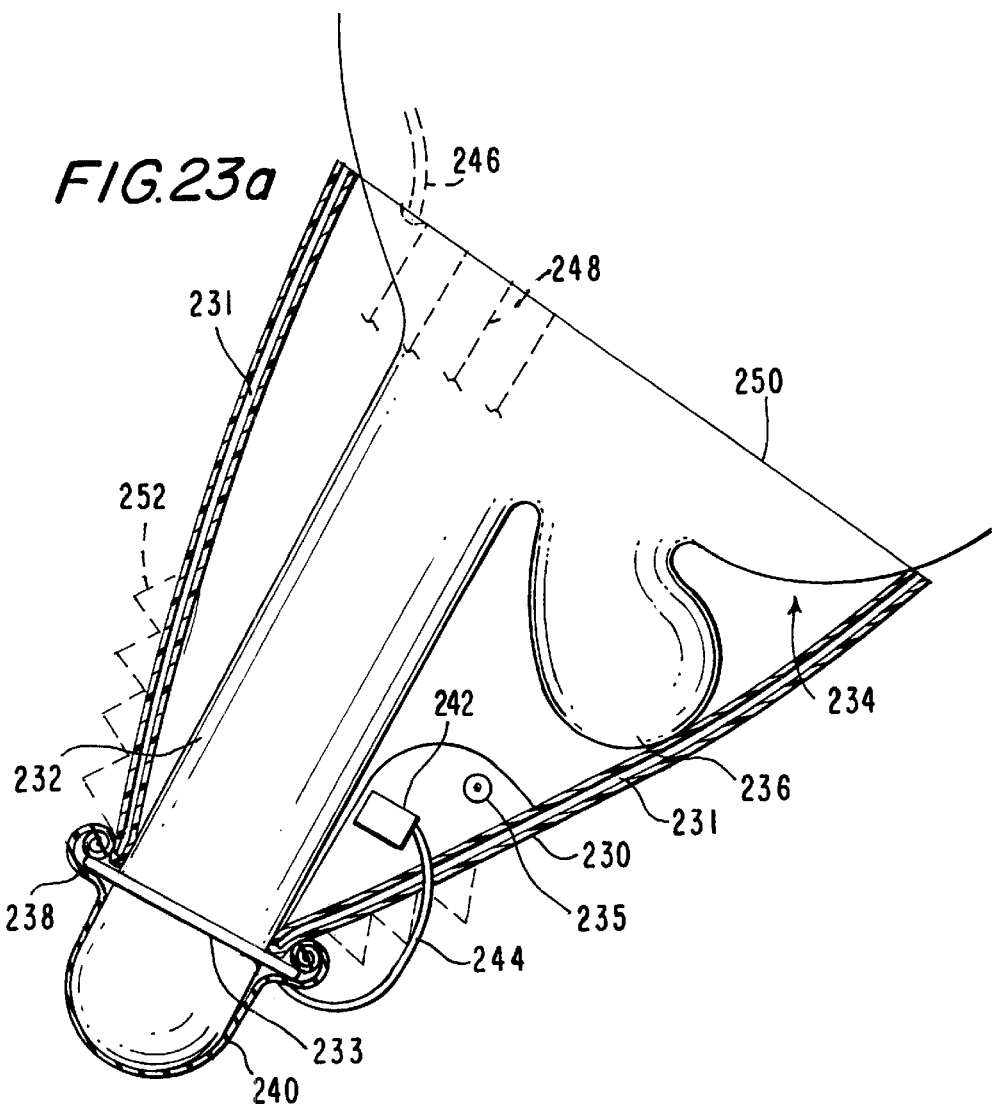
FIG. 23a is a partial detail of an alternate embodiment of the condom applicator shown in FIG. 23.
Figure 23:
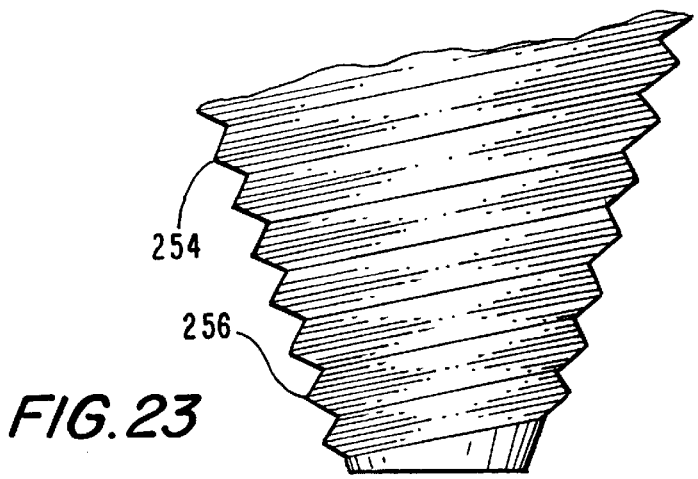
FIG. 23 is a partial cross-sectional elevation view of a condom applicator being used to apply any one of the first eleven embodiments of the invention to a male user.

FIG. 23 shows a condom applicator 230 designed to apply one of the first eleven embodiments of the invention to the erect penis 232 of the user. The condom applicator may be made out of plastic or other light material. The condom applicator 230 is conical in shape, open at a base end 250 and at a top end 233, and the base end 250 of the condom applicator 230 is so dimensioned that it may be placed comfortably against and be braced by the genital area 234 of the user during application of the condom and during possible use of the condom applicator 230 for inflation of the lateral compressive pressure exerting means on the condom. In particular, the sloping walls of the condom applicator 230 should preferably be dimensioned such that they do not cause discomfort to the scrotum 236 of the user during the bracing process. A top lip 238 of the condom applicator 230 holds the condom 240 in its initially unstretched state forming a flat "lid" for the aperture of the top end 233 of the condom applicator 230. The condom applicator 230 is preferably sold separately from the condom 240, and may be reused to apply multiple condoms 240, each condom 240 being placed on the applicator 230 in the position described. Of course, in FIG. 23, the condom applicator 230 is shown in position braced against the body 234 of the user where the head of the erect penis 232 of the user has stretched the condom from its initially flat unstretched state.

The condom applicator 230 is double walled, the double walls enclosing a leak proof chamber 231 which may be initially charged with an air supply by a one-way valve 235, the air supply being provided to inflate the microtubules or other lateral compressive pressure exerting means on the condom 240. In such a case, the air supply is conducted to the condom 240 by a user-activated relief valve 242 and a tube 244 leading from the user-activated relief valve 242 to the pressure exerting means on the condom 240. The condom applicator 230 may, alternatively, act as a conduit for transmitting air supplied from an external source to the condom 240. The air may be supplied to the condom applicator 230 by, for example, a tube 246 leading from an air pump (not shown) to the condom applicator 230.

If adjustability of the circumferential dimension of the condom applicator is needed due to variability of the geometry of the genital areas 234 and of the length of erect penises of users, pleats 248 may be introduced into the walls of the condom applicator 230. Such pleats could, for example, begin at the base end 250 of the condom applicator 230 and extend upward for any portion of the height of the condom applicator 230 desired, depending on the height over which circumferential adjustability of the condom applicator 230 is desired. In addition, if the height of the condom applicator must also be adjusted due to variability of the geometry of the genital areas 234 and the length of erect penises of users, a series of pleats 252, each pleat extending around the circumferential dimensions of the condom applicator 230, and the series of pleats 252 extending along the length of the condom applicator 230, could be used to vary the height of the condom applicator 230. These pleats 252 may be extended over the entire height of the condom applicator 230 or, similarly to the pleats 248, over any portion thereof. Finally, a combination of the two sets of pleats 248, 252 could be used to obtain the desired dimensional adjustability of the condom applicator 230.

FIG. 23a shows a partial detail of an alternate embodiment of the condom applicator shown in FIG. 23. This condom applicator 254 differs from the condom applicator 230 in that it possesses a series of circumferential pleats 256 forming a bellows-like arrangement. Although the condom applicator 230 optionally possesses a series of pleats 252 with a similar geometry, the function of these pleats 256 is different than those optionally found in the condom applicator 230. These pleats 256 act as a bellows in pumping air into a condom placed on the top end of the condom applicator 254. The condom applicator 254 thus acts as a pump for a condom placed on its top end. Atmospheric air is drawn into an internal chamber of the condom applicator 254 by suction through an air inlet (not shown) at the base end of the condom applicator 254 and forced out of the condom applicator 254 as the bellows arrangement formed by the pleats 256 is compressed and expanded by forces manually applied near or at the base end of the condom applicator 254. The pumped atmospheric air is conducted from the condom applicator 254 to the pressure exerting means on the condom by a tube (not shown) similar to that shown in FIG. 23. Since the forces manually applied at or near the base end of the condom applicator 254 will move the base end toward and away from the body of the user, no bracing of the condom applicator 254 against the body of the user will be possible during inflation of the pressure exerting means on the condom as was true of the condom applicator 230. Instead, the user will be required to hold the base end of the condom applicator 254 as he applies forces to that end during inflation of the pressure exerting means.

Figure 24:
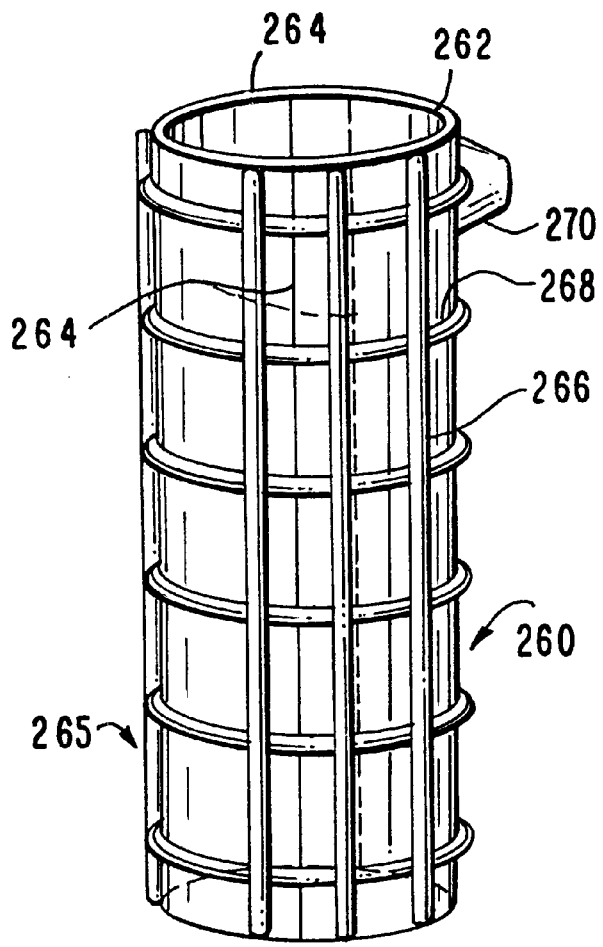
FIG. 24 is an elevation view of a sixteenth embodiment of the invention comprising a removable mesh of microtubules, the removable mesh of microtubules being adapted to be applied to a conventional male condom.

FIG. 24 shows a sixteenth embodiment of the invention comprising a removable mesh 260 of microtubules that may be applied to a conventional male condom. The mesh comprises a sheet 262, preferably of one of the materials found suitable for condoms as specified in connection with the first embodiment of the invention, with a backing 264 allowing it to removably adhere to the tubular membrane of a conventional condom on which the sheet 262 fits like a sleeve. To allow for circumferential adjustment and continuous contact between the sheet 262 and varying sizes of the underlying condom, the edges 264 of the sheet 262 overlap each other and can be removed from contact with each other and reattached to make any required circumferential adjustment within the width of the sheet. Attached to the sheet is a network 265 of longitudinal microtubules 266 and circumferential microtubules 268 similar to those described in embodiments of the invention described above. An inflation compartment 270 containing an air supply or other equivalent means for supplying an expansive substance is attached to the network 265 of microtubules so that the network 265 of microtubules may be inflated. The inflation compartment 270 is also attached to the sheet 262.

The mesh 260 allows the user to transform any conventional male condom into a condom exerting lateral pressure on the penis simply by applying the mesh 260 to the condom after the condom is applied to his erect penis. The condom may be adjusted to assure a tight fit by adjustment of the edges 264 of the sheet 262, either pulling those edges 264 so that they move away from each other, thus decreasing the circumference of the sheet 262, or pushing the edges 264 so that they move toward each other, thus increasing the circumference of the sheet 262. In any event, once a tight fit between the underlying condom and the sheet 262 is achieved, the network of microtubules may be inflated by activating the air supply source or other expansive substance source. Areas of texturing or other equivalent means for gripping the edges 264 of the sheet 262 could be added to the sheet 262 if users experience difficulty in stretching the sheet 262 over their erect penises. The need for the sheet 262 may be eliminated if the microtubule network 265 is so constructed that the microtubules in both the longitudinal and circumferential directions abut each other forming a continuous network 265 of microtubules. In such a case, the continuous network 265 of microtubules would be removably attachable directly to a conventional male condom.

Figure 24A:
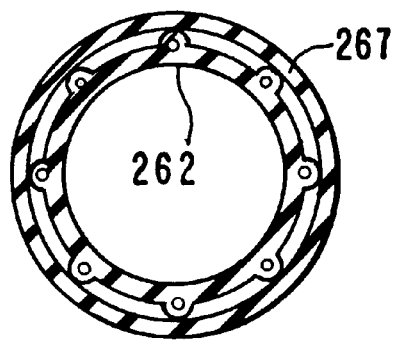
FIG. 24a is a cross-sectional view of an alternate embodiment of the removable mesh of microtubules shown in FIG. 24 that may possibly be reusable.
Figure 24B:
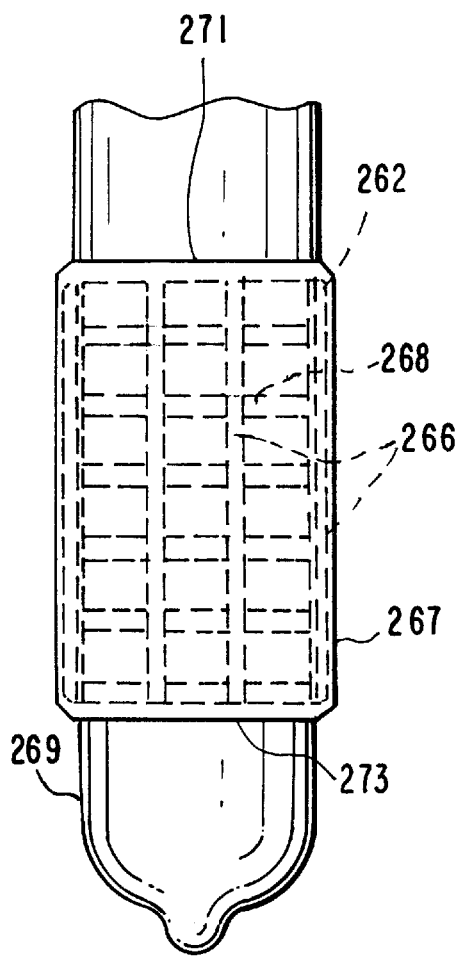
FIG. 24b is an elevation view of the alternate embodiment of the removable mesh of microtubules shown in FIG. 24a, the alternate embodiment being attached to a conventional male condom.

At least part of the mesh could possibly be made reusable if a second sheet 267 is removably attached on top of the network 265 of microtubules when the mesh 260 is manufactured, (see FIG. 24a). The second sheet 267 would be used once during the initial use of the mesh 260 and afterward removed from the remainder of the mesh 260 and discarded. The second sheet 267 would be acting as a false outer surface of the male condom 269 on which the mesh 260 was applied. The second sheet 267 would, thus, contact the vagina instead of the remainder of the mesh 260. This contact of the second sheet 267 with the vagina would disqualify it for a second use because of sanitary concerns. Since it is hoped, however, that the remainder of the mesh 260 comprising the first sheet 262 and the network 265 of microtubules never contacts the vagina, it should be reusable on a second condom. To insure no contact between the vagina and the remainder of the mesh 260, the second sheet should preferably be of such length that its opposite edges 271, 273 along the length of the underlying condom 269 overlap the length of the remainder of the mesh 260 underneath by an amount sufficient to allow the second sheet 267 to be removably attached directly to the condom 269, (see FIG. 24b). Such an arrangement results in a total enclosure of the remainder of the mesh 260, and prevents the remainder of the mesh 260 from contacting the vagina. In such a case, the remainder of the mesh 260 may be reused indefinitely, provided that a new second sheet 267 is obtained and arranged as set forth above every time the remainder of the mesh 260 is reused. Second sheets 267 could preferably be separately sold. The reusability of the remainder of the mesh 260 may depend, at least in part, on the reliability of the attachment of the second sheet 267 to the condom 269 and to the remainder of the mesh 260 in preventing any contact between the remainder of the mesh 260 and the vagina. The reusability of the mesh 260 may also depend on the reliability of users in correctly attaching the second sheet 267 to the remainder of the mesh 260 and to the underlying condom 269.

It should be understood that the concept of a removable and reusable mesh of microtubules could also be applied to variations of any of the purely feminine condoms disclosed in this application. Such feminine condoms could be fully extended outside of the vagina as a somewhat stiff structure prior to use for the purpose of application of a removable and possibly reusable mesh of microtubules. Such feminine condoms could be extended to form the somewhat stiff structure suitable for such application by the presence of, for example, a "skeleton" of preexisting microtubules on the feminine condom comprising, for example, one longitudinal microtubule and one circumferential microtubule. The remainder of the microtubule network would be supplied by the removable and possibly reusable mesh of microtubules.

Figure 25:
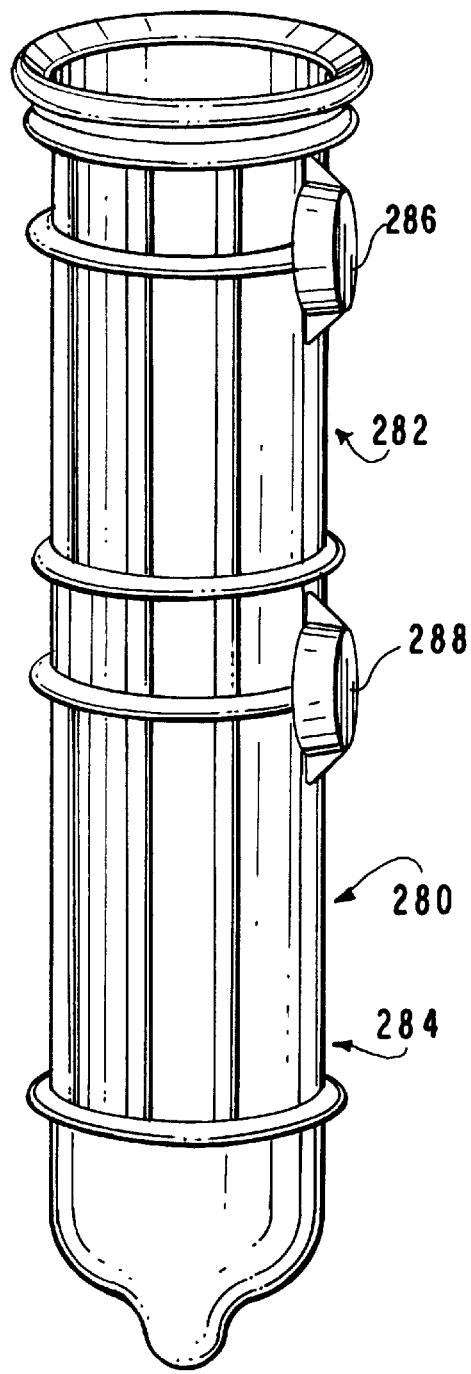
FIG. 25 is an elevation view of a seventeenth embodiment of the invention.

FIG. 25 shows a seventeenth embodiment of the invention. It differs from the first embodiment of the invention in that the condom 280 has two independent and unconnected networks of microtubules 282, 284 supplied by two independent expansive substance sources supplying an expansive substance through two inflation compartments 286, 288. The use of two (or even more than two) independent networks of microtubules might be advantageous if different levels of lateral pressure could be advantageously applied to different regions of the condom 280. It should, of course, be understood that this concept of two or more independent networks of microtubules shown here as applied to the male condom disclosed in the first embodiment of the invention could be as easily applied to any of the other embodiments of the invention where a male or hermaphroditic condom is disclosed, namely, the second through eleventh embodiments of the invention, inclusive, and the fifteenth embodiment of the invention.

Figure 26:
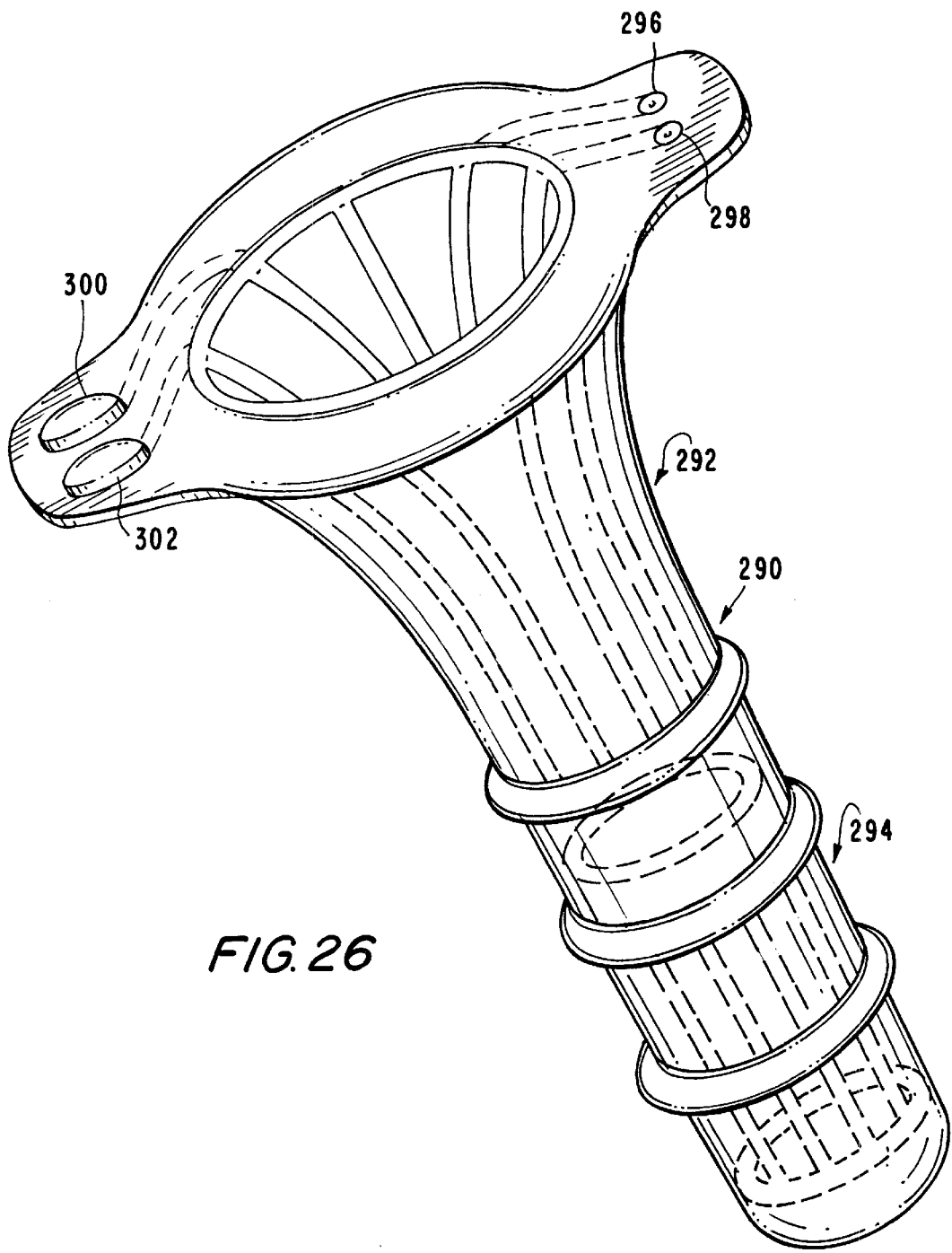
FIG. 26 is an elevation view of an eighteenth embodiment of the invention.

FIG. 26 shows an eighteenth embodiment of the invention. Analogously to the sixteenth embodiment of the invention which shows the application of two or more independent networks of microtubules to a male condom embodiment of the invention, FIG. 26 shows the application of the same concept to a female condom embodiment of the invention, namely, the twelfth embodiment of the invention. Thus, the eighteenth embodiment of the invention differs from the twelfth embodiment of the invention in that the condom 290 has at least two independent and unconnected networks of microtubules 292, 294, each network inflated by one of at least two air sources or sources of another expansive substance 296, 298 and each network deflated by one of at least two relief valves 300, 302. As in the seventeenth embodiment of the invention, the use of two (or even more than two) independent networks of microtubules might is be advantageous if different levels of lateral pressure could be advantageously applied to different regions of the condom 290. It should, of course, be understood that this concept of two or more independent networks of microtubules shown here as applied to the female condom disclosed in the twelfth embodiment of the invention could be as easily applied to any of the other embodiments of the invention where a female condom is disclosed, namely, the thirteenth and fourteenth embodiments of the invention.

While preferred embodiments have been described herein, it will be understood by those with ordinary skill in the art that various modifications, changes, or alterations may be made to the invention disclosed and described herein without departing from its scope or its equivalent as claimed in the appended claims.

Thus, for example, as mentioned above, the condom disclosed and claimed herein may be of a circular cross-section, substantially triangular cross-section, or any other closed cross-sectional shape as appropriate to achieve maximum comfortable and safe lateral pressure on the penis of a user. In particular, although the first six embodiments of the invention and the ninth through the seventeenth embodiments of the invention, inclusive, were shown or could be assumed to have circular cross-sections, even if such circular cross-sections varied in diameter along the length of the condom, (see FIGS. 1b, 9a, 10a, 12a), and, therefore, being cylindrical or tubular with a cross-section of circles of varying diameter when extended, it would readily occur to one with ordinary skill in the art that their cross-sections could be made in a substantially triangular shape or any other closed shape appropriate to produce maximum safe and comfortable lateral pressure on the penis of a user.

In addition, the position of the microtubules as shown in the first ten embodiments of the invention so that they protrude from the exterior wall of the membrane of the condom, from the interior wall of the membrane of the condom, both from the exterior and interior walls of the membrane of the condom, or from neither the exterior nor interior walls of the membrane of the condom should be understood to be equally available as alternatives for the eleventh through fifteenth and seventeeth and eighteenth embodiments of the invention.

Analogously, with regard to the removable mesh 260, we assumed in the description above that the network 265 of microtubules are placed such that they protrude beyond the exterior surface of the sheet 262 when theremovable mesh 260 is placed on a condom. However, as previously described in other embodiments of the invention, it should also be understood that the microtubules can be placed so that some or all of them protrude from the interior surface of the sheet 262 and contact the condom on which the sheet is placed. Finally, as also described in previous embodiments, some or all of the microtubules may be placed such that they protrude from neither of or both of the interior and exterior surfaces of the sheet 262.

Furthermore, some or all of the microtubules 6 or the toroidal chamber 16 may be prefilled with air or another pressure exerting gas or substance, instead of filling them with air upon application of the condom.

What is claimed is:

1. A device for acting as a barrier between a genital area of a male person and a genital area of a female person immediately before, during and immediately after sexual intercourse, said barrier device comprising:
   a. a tubular membrane open at a first end and closed at a second end, said membrane adapted to be interposed between a penis of said male person and the vagina of said female person when said penis is inserted in said vagina:
   b. a means for exerting lateral compressive pressure on said penis and on said vagina;
   c. means for seating the barrier device on a labia major of said female person, said means for seating comprising a lip attached to said first end of said tubular membrane; and
   d. an expansive substance source and a relief valve located in said lip.

2. A device for acting as a barrier as claimed in claim 1, wherein an initially rolled up membrane is integrally attached to an outer periphery of said lip.

3. A device for acting as a barrier as claimed in claim 2, wherein said membrane when unrolled is adapted to cover a combination of:
   a. a pubic region; and
   b. any one of or any combination of: a portion of a lower abdomen, a right groin, a left groin, a right inner thigh, a left inner thigh, and a perineum and an anus of said female person.

4. A device for acting as a barrier as claimed in claim 1, wherein said means for seating further comprises a flexible ring attached to said first end of said tubular membrane.

5. A device for acting as a barrier as claimed in claim 1, wherein said tubular membrane is made from a polymer.

6. A device for acting as a barrier as claimed in claim 5, wherein said polymer is not an elastomer.

7. A device for acting as a barrier as claimed in claim 1, wherein said tubular membrane has a circular cross-section, said cross-section being taken perpendicularly to a central axis of said tubular membrane.

8. A device for acting as a barrier as claimed in claim 1, further comprising a means for maintaining a nondecreasing amount of said lateral compressive pressure on said penis and said vagina and a means for decreasing said lateral compressive pressure on said penis and said vagina.

9. A device for acting as a barrier as claimed in claim 1, wherein at least one region of said tubular membrane is of reduced interior diameter.

10. A device for acting as a barrier as claimed in claim 1, wherein said first end of said tubular membrane is initially covered by a means for sealing said first end.

11. A device for acting as a barrier as claimed in claim 1, wherein said tubular membrane is of increased thickness in a region adjacent to said first end of said tubular membrane, said region being adapted to be in at least close proximity to a clitoris of said female person when said tubular membrane is inserted into said vagina.

12. A device for acting as a barrier as claimed in claim 1, wherein said tubular membrane is of continually increasing external diameter in a region adjacent to said first end of said tubular membrane.

13. A device for acting as a barrier as claimed in claim 1, wherein said tubular membrane is made from an elastomeric material.

14. A device for acting as a barrier as claimed in claim 13, wherein said elastomeric material is latex.

15. A device for acting as a barrier as claimed in claim 13, wherein said elastomeric material is polyurethane.

16. A device for acting as a barrier as claimed in claim 1, wherein said tubular membrane has a circular cross-section, said cross-section being taken perpendicularly to a central axis of said tabular membrane.

17. The barrier device of claim 1 where said means for exerting lateral compressive pressure on a penis of a male person and on a vagina of a female person is adapted to be removably attached to a tubular membrane open at a first end and closed at a second end adapted to be applied to the exterior of the skin of said penis.

18. A device for exerting lateral compressive pressure as claimed in claim 17, wherein said means for exerting lateral compressive pressure is adapted to be removed from said tubular membrane and attached to at least another tubular membrane for reuse.

19. A device for exerting lateral compressive pressure as claimed in claim 17, wherein said means for exerting lateral compressive pressure comprises a sheet adapted to be removably attached to said tubular membrane and adapted to be removably attached at its opposite longitudinal edges to form a cylinder.

20. A device for exerting lateral compressive pressure as claimed in claim 19, wherein said sheet is made from a polymer.

21. A device for exerting lateral compressive pressure as claimed in claim 20, wherein said polymer is not an elastomeric material.

22. A device for exerting lateral compressive pressure as claimed in claim 19, wherein said means for exerting lateral compressive pressure further comprises at least one microtubule.

23. A device for exerting lateral compressive pressure as claimed in claim 22, wherein said at least one microtubule comprises at least one circumferential microtubule.

24. A device for exerting lateral compressive pressure as claimed in claim 23, wherein at least one of said at least one circumferential microtubule is located such that a wall of said at least one of said at least one circumferential microtubule protrudes from an exterior surface of said tubular membrane.

25. A device for exerting lateral compressive pressure as claimed in claim 22, wherein said at least one microtubule comprises at least one longitudinal microtubule.

26. A device for exerting lateral compressive pressure as claimed in claim 25, wherein at least one of said at least one longitudinal microtubule is located such that a wall of said at least one of said at least one longitudinal microtubule protrudes from an exterior surface of said tubular membrane.

27. A barrier device as claimed in claim 1, wherein said lip is of varying radial dimension, said lip having at least two protrusions on an outer periphery of said lip.

28. A barrier device as claimed in claim 27, wherein said lip is of asymmetrical dimension along a greatest diameter of said lip, said asymmetry being with respect to a center of said opening at said first end of said tubular membrane.

29. A device for tightly enclosing a user's penis to improve the user's erection when the user's penis is in an erect state, said device comprising:
    a. a tubular membrane open at a first end and closed at a second end, said tubular membrane adapted to be applied to the exterior of the skin of the user's penis; and
    b. means for exerting lateral compressive pressure on said user's penis, at least a portion of said means for exerting lateral compressive pressure being irremovably joined with said tubular membrane, said lateral compressive pressure being exerted in at least one region to improve the user's erection, said lateral compressive pressure being exerted without the use of any shear stress applied to said tubular membrane as a result of sexual intercourse;
wherein said tubular membrane has a substantially triangular cross-section, said cross-section being taken perpendicularly to a central axis of said tubular membrane.

30. A device for tightly enclosing a user's penis to improve the user's erection when the user's penis is in an erect state, said device comprising:
    a. a tubular membrane open at a first end and closed at a second end, said tubular membrane adapted to be applied to the exterior of the skin of the user's penis; and
    b. means for exerting lateral compressive pressure on said user's penis, at least a portion of said means for exerting lateral compressive pressure being irremovably joined with said tubular membrane, said lateral compressive pressure being exerted in at least one region to improve the user's erection, said lateral compressive pressure being exerted without the use of any shear stress applied to said tubular membrane as a result of sexual intercourse;
wherein said means for exerting lateral compressive pressure on said user's penis comprises a hollow lip at said first end of said tubular membrane, said hollow lip forming a toroidal chamber contained within said lip.

31. A device for tightly enclosing a user's penis to improve the user's erection when the user's penis is in an erect state, said device comprising:
    a. a tubular membrane open at a first end and closed at a second end, said tubular membrane adapted to be applied to the exterior of the skin of the user's penis; and
    b. means for exerting lateral compressive pressure on said user's penis, at least a portion of said means for exerting lateral compressive pressure being irremovably joined with said tubular membrane, said lateral compressive pressure being exerted in at least one region to improve the user's erection, said lateral compressive pressure being exerted without the use of any shear stress applied to said tubular membrane as a result of sexual intercourse;
wherein said means for exerting lateral compressive pressure on said user's penis comprises a hollow lip at said first end of said tubular membrane, said means for exerting lateral compressive pressure on said user's penis further comprising means for tightening around said user's penis, said means for tightening being contained within said hollow lip.

32. A device for tightly enclosing a user's penis as claimed in claim 31, wherein said means for tightening around said user's penis comprises a cord and means for tightening said cord.

33. A device for tightly enclosing a user's penis as claimed in claim 32, wherein said means for tightening said cord comprises a means for locking said means for tightening said cord in a certain position on said cord and a means for manually releasing said means for tightening said cord when said means for tightening said cord is in a locked position.

34. A device for enclosing a user's penis, said means comprising:
    a. a tubular membrane open at a first end and closed at a second end, said tubular membrane adapted to be applied to the exterior of the skin of the user's penis; and
    b. means for expansion to simulate an erection of said user's penis, at least a portion of said means for expansion being irremovably joined with said tubular membrane, said expansion being produced without the use of any shear stress applied to said tubular membrane as a result of sexual intercourse;
wherein said tubular membrane has a substantially triangular cross-section, said cross-section being taken perpendicularly to a central axis of said tubular membrane.

35. A device for enclosing a user's penis as claimed in claim 34, wherein said means for expansion comprises at least one microtubule.

36. A device for enclosing a user's penis as claimed in claim 35, wherein said at least one microtubule comprises at least one circumferential microtubule.

37. A device for enclosing a user's penis as claimed in claim 36, wherein at least one of said at least one circumferential microtubule is located such that a wall of said at least one of said at least one circumferential microtubule protrudes from an exterior surface of said tubular membrane.

38. A device for enclosing a user's penis as claimed in claim 36, wherein said means for expansion further comprises an inflation compartment.

39. A device for enclosing a user's penis as claimed in claim 38, further comprising a means for maintaining a nondecreasing amount of said expansion.

40. A device for enclosing a user's penis as claimed in claim 35, wherein said at least one microtubule comprises at least one longitudinal microtubule.

41. A device for enclosing a user's penis as claimed in claim 40, wherein at least one of said at least one longitudinal microtubule is located such that a wall of said at least one of said at least one longitudinal microtubule protrudes from an exterior surface of said tubular membrane.

42. A device for enclosing a user's penis as claimed in claim 40, wherein said means for expansion further comprises an inflation compartment.

43. A device for enclosing a user's penis as claimed in claim 42, further comprising a means for maintaining a nondecreasing amount of said expansion.

44. A device for acting as a barrier between a genital area of a male person and a genital area of a female person immediately before, during and immediately after sexual intercourse, said barrier device comprising:
   a. a tubular membrane open at a first end and closed at a second end, said membrane adapted to be interposed between a penis of said male person and the vagina of said female person when said penis is inserted in said vagina;
   b. a means for exerting lateral compressive pressure on said penis and on said vagina,
   c. means for seating the barrier device on a labia major of said female person, said means for seating comprising a lip attached to said first end of said tubular membrane and wherein said means for seating further comprises a flexible ring attached to said first end of said tubular membrane, said flexible ring having indentations across the thickness of said ring in two locations, dividing said ring into separate parts.

45. A device for acting as a barrier as claimed in claim 44, wherein said means for exerting lateral pressure comprises at least one microtubule.

46. A device for acting as a barrier as claimed in claim 45, wherein said at least one microtubule comprises at least one circumferential microtubule.

47. A device for acting as a barrier as claimed in claim 46, wherein at least one of said at least one circumferential microtubule is located such that a wall of said at least one of said at least one circumferential microtubule protrudes from an exterior surface of said tubular membrane.

48. A device for acting as a barrier as claimed in claim 47, wherein at least one of said at least one circumferential microtubule is in a region adjacent to said first end of said tubular membrane.

49. A device for acting as a barrier as claimed in claim 46, wherein at least one of said at least one circumferential microtubule is located such that a wall of said at least one of said at least one circumferential microtubule protrudes from an interior surface of said tubular membrane.

50. A device for acting as a barrier as claimed in claim 45, wherein said at least one microtubule exerts forces which vary in different directions.

51. A device for acting as a barrier as claimed in claim 44, wherein said tubular membrane comprises at least one pleat.

52. A device for acting as a barrier between a genital area of a male person and a genital area of a female person immediately before, during and immediately after sexual intercourse, said barrier device comprising:
   a. tubular membrane open at a first end and closed at a second end, said membrane adapted to be interposed between a penis of said male person and the vagina of said female person when said penis is inserted in said vagina;
   b. a means for exerting lateral compressive pressure on said penis and on said vagina;
   c. means for seating the barrier device on a labia major of said female person,
wherein said means for exerting lateral pressure comprises at least one microtubule, said at least one microtubule comprising, at least two circumferential microtubules, at least one of said at least two circumferential inscrutables being unconnected to at least another of said at least two circumferential microtubules.

53. A device for acting as a barrier as claimed in claim 52, wherein said at least one microtubule comprises at least one longitudinal microtubule.

54. A device for acting as a barrier as claimed in claim 53, wherein at least one of said at least one longitudinal microtubule is located such that a wall of said at least one of said at least one longitudinal microtubule protrudes from an exterior surface of said tubular membrane.

55. A device for acting as a barrier as claimed in claim 53, wherein at least one of said at least one longitudinal microtubule is located such that a wall of said at least one of said at least one longitudinal microtubule protrudes from an interior surface of said tubular membrane.

56. A device for acting as a barrier between a genital area of a male person and a genital area of a female person immediately before, during and immediately after sexual intercourse, said barrier device comprising:
   a. a tubular membrane open at a first end and closed at a second end, said membrane adapted to be interposed between a penis of said male person and the vagina of said female person when said penis is inserted in said vagina;
   b. a means for exerting lateral compressive pressure on said penis and on said vagina,
wherein said means for exerting lateral pressure comprises at least one microtubule, said at least one microtubule comprising at least one circumferential microtubule, comprising at least two circumferential microtubules, at least one of said at least two circumferential microtubules being unconnected to at least another of said at least two circumferential microtubules.

57. A device for acting as a barrier as claimed in claim 56, wherein said at least one microtubule comprises at least one longitudinal microtubule.

58. A device for acting as a barrier as claimed in claim 56, wherein at least one of said at least one longitudinal microtubule is located such that a wall of said at least one of said at least one longitudinal microtubule protrudes from an exterior surface of said tubular membrane.

59. A device for acting as a barrier between a genital area of a male person and a genital area of a female person immediately before, during and immediately after sexual intercourse, said barrier device comprising:
   a. a tubular membrane open at a first end and closed at a second end, said membrane adapted to be interposed between a penis of said male person and the vagina of said female person when said penis is inserted in said vagina;
   b. a means for exerting lateral compressive pressure on said penis and on said vagina,
wherein said means for exerting lateral pressure comprises at least one microtubule said at least one microtubule comprising at least one longitudinal microtubule which comprises at least two longitudinal microtubules, at least one of said at least two longitudinal microtubules being unconnected to at least another of said at least two longitudinal microtubules.

60. A device for acting as a barrier as claimed in claim 59, wherein said at least one microtubule exerts forces which vary in different directions.

61. A device for acting as a barrier between a genital area of a male person and a genital area of a female person immediately before, during and immediately after sexual intercourse, said barrier device comprising:
   a. a tubular membrane open at a first end and closed at a second end, said membrane adapted to be interposed between a penis of said male person and the vagina of said female person when said penis is inserted in said vagina;

b. a means for exerting lateral compressive pressure on said penis and on said vagina wherein said means for exerting lateral pressure comprises at least one microtubule and said at least one microtubule comprises at least one circumferential microtubule and at least one longitudinal microtubule, at least one of said at least one longitudinal microtubule being unconnected to at least one of said at least one circumferential microtubule.

62. A device for acting as a barrier as claimed in claim 61, wherein at least one of said at least one circumferential microtubule is located such that a wall of said at least one of said at least one circumferential microtubule protrudes from an exterior surface of said tubular membrane.

63. A device for acting as a barrier as claimed in claim 61, wherein said means for exerting lateral compressive pressure further comprises an expansive substance source.

64. A device for acting as a barrier as claimed in claim 63, further comprising a means for maintaining a nondecreasing amount of said lateral compressive pressure on said penis and said vagina.

65. A device for acting as a barrier between a genital area of a male person and a genital area of a female person immediately before, during and immediately after sexual intercourse, said barrier device comprising:

a. a tubular membrane open at a first end and closed at a second end, said membrane adapted to be interposed between a penis of said male person and the vagina of said female person when said penis is inserted in said vagina;

b. a means for exerting lateral compressive pressure on said penis and on said vagina, said tubular membrane adapted to be applied to the exterior of the skin of said penis, said lateral compressive pressure being exerted in at least one region to improve said male person's erection when said penis is in an erect state, said lateral compressive pressure being exerted without the application of shear stress to said tubular membrane, at least a portion of said means for exerting lateral compressive pressure being irremovably joined with said tubular membrane, said means for exerting lateral pressure comprises at least one circumferential microtubule, wherein at least one of said at least one circumferential microtubule is located such that a wall of said at least one of said at least one circumferential microtubule protrudes from an interior surface of said tubular membrane.

66. A device for acting as a barrier as claimed in claim 65, wherein said tubular membrane is made from an elastomeric material.

67. A device for acting as a barrier as claimed in claim 66, wherein said tubular membrane has a circular cross-section, said cross-section being taken perpendicularly to a central axis of said tubular membrane.

68. A device for acting as a barrier as claimed in claim 65, wherein said at least one region in which said lateral compressive pressure is being exerted comprises a perimeter of said user's penis, said perimeter being located at a base of said user's penis.

69. A device for acting as a barrier as claimed in claim 65, wherein said at least one microtubule comprises at least one circumferential microtubule.

70. A device for acting as a barrier as claimed in claim 65, wherein at least one of said at least one circumferential microtubule is located such that a wall of said at least one of said at least one circumferential microtubule protrudes from an exterior surface of said tubular membrane.

71. A method for applying a device for acting as a barrier as claimed in claim 65 to said penis, comprising the steps of:

a. Applying said tubular membrane to said penis when said penis is an erect state; and b. exerting lateral pressure on said penis using said means for exerting lateral compressive pressure on said penis.

72. A method for applying a device for acting as a barrier as claimed in claim 71, wherein said lateral compressive pressure is exerted by air.

73. A method for applying a device for acting as a barrier as claimed in claim 71, wherein said lateral compressive pressure is exerted by means for tightening around said penis.

74. A method for applying a device for acting as a barrier as claimed in claim 73, wherein said means for tightening around said penis comprises a cord and means for tightening said cord.

75. A device for acting as a barrier between a genital area of a male person and a genital area of a female person immediately before, during and immediately after sexual intercourse, said barrier device comprising:

a. tubular membrane open at a first end and closed at a second end, said membrane adapted to be interposed between a penis of said male person and the vagina of said female person when said penis is inserted in said vagina; a means for exerting lateral compressive pressure on said penis and on said vagina, said tubular membrane adapted to be applied to the exterior of the skin of said penis, said lateral compressive pressure being exerted in at least one region to improve said male person's erection when said penis is in an erect state, said lateral compressive pressure being exerted without the application of shear stress to said tubular membrane, at least a portion of said means for exerting lateral compressive pressure being irremovably joined with said tubular membrane, said means for is exerting lateral compressive pressure comprising at least one microtubule, wherein at least one of said at least one longitudinal microtubule is located such that a wall of said at least said at least one longitudinal microtubule protrudes from an interior surface of said tubular membrane.

76. A device for acting as a barrier as claimed in claim 75, wherein at least one of said at least one longitudinal microtubule is located such that a wall of said at least one of said at least one longitudinal microtubule protrudes from an exterior surface of said tubular membrane.

77. A device for acting as a barrier as claimed in claim 75, wherein said means for exerting lateral compressive pressure further comprises an inflation compartment.

78. A device for acting as a barrier as claimed in claim 77, further comprising a means for maintaining a nondecreasing amount of said lateral compressive pressure.

79. A device for acting as a barrier as claimed in claim 75, wherein said means for exerting lateral compressive pressure further comprises an inflation compartment.

80. A device for acting as a barrier as claimed in claim 79, further comprising a means for maintaining a nondecreasing amount of said lateral compressive pressure.

81. A device for acting as a barrier between a genital area of a male person and a genital area of a female person immediately before, during and immediately after sexual intercourse, said barrier device comprising;

a. a tubular membrane open at a first end and closed at a second end, said membrane adapted to be interposed between a penis of said male person and the vagina of said female person when said penis is inserted in said vagina;

b. a means for exerting lateral compressive pressure on said penis and on said vagina, said tubular membrane adapted to be applied to the exterior of the skin of said penis, said lateral compressive pressure being exerted in at least one region to improve said male person's erection when said penis is in an erect state, said lateral compressive pressure being exerted without the application of shear stress to said tubular membrane, at least a portion of said means for exerting lateral compressive pressure being is irremovably joined with said tubular membrane, wherein said means for exerting lateral compressive pressure comprises a hollow lip at said first end of said tubular membrane, said hollow lip forming a torroidal chamber within said lip.

82. A device for acting as a barrier as claimed in claim 81, wherein said means for exerting lateral compressive pressure further comprises means for tightening around said penis, said means for tightening being contained within said hollow lip.

83. A device for acting as a barrier as claimed in claim 82, wherein said means for tightening around said penis comprises a cord and means for tightening said cord.

84. A device for acting as a barrier as claimed in claim 83, wherein said means for tightening said cord comprises a means for locking said means for tightening said cord in a certain position on said cord and a means for manually releasing said means for tightening said cord when said means for tightening said cord is in a locked position.

85. A device for acting as a barrier between a genital area of a male person and a genital area of a female person immediately before, during and immediately after sexual intercourse, said barrier device comprising:

a. a tubular membrane open at a first end and closed at a second end, said membrane adapted to be interposed between a penis of said male person and the vagina of said female person when said penis is inserted in said vagina;

b. a means for exerting lateral compressive pressure on said penis and on said vagina;

c. means for seating the barrier device on a labia major of said female person, wherein said tubular membrane has a substantially triangular cross-section, said cross-section being taken perpendicularly to a central axis of said tubular membrane.

86. A device for acting as a barrier between a genital area of a male person and a genital area of a female person immediately before, during and immediately after sexual intercourse, said barrier device comprising:

a. a tubular membrane open at a first end and closed at a second end, said membrane adapted to be interposed between a penis of said male person and the vagina of said female person when said penis is inserted in said vagina;

b. a means for exerting lateral compressive pressure on said penis and on said vagina;

c. means for seating the barrier device on a labia major of said female person, wherein said means for exerting lateral pressure comprises at least one longitudinal microtubule, said at least one longitudinal microtubule comprising at least two longitudinal microtubules, at least one of said at least two longitudinal microtubules being unconnected to at least another of said at least two longitudinal microtubules.

87. A device for acting as a barrier between a genital area of a male person and a genital area of a female person immediately before, during and immediately after sexual intercourse, said barrier device comprising:

a. tubular membrane open at a first end and closed at a second end, said membrane adapted to be interposed between a penis of said male person and the vagina of said female person when said penis is inserted in said vagina;

b. a means for exerting lateral compressive pressure on said penis and an said vagina;

c. means for seating the barrier device on a labia major of said female person, wherein said means for exerting lateral pressure comprises at least one microtubule, and said at least one microtubule is of varying thickness along a perimeter of said at least one microtubule.

88. A device for acting as a barrier between a genital area of a male person and a genital area of a female person immediately before, during and immediately after sexual intercourse, said barrier device comprising:

a. a tubular membrane, open at a first end and closed at a second end, said membrane adapted to be interposed between a penis of said male person and the vagina of said female person when said penis is inserted in said vagina;

b. a means for exerting lateral compressive pressure on said penis and on said vagina;

c. means for seating the barrier device on a labia major of said female person, wherein said means for exerting lateral pressure comprises at least one microtubule and said at least one microtubule comprises at least one circumferential microtubule and at least one longitudinal microtubule, at least one of said longitudinal microtubule being unconnected to at least one of said at least one circumferential microtubule.

89. A device for inserting a device for acting as a barrier between a genital area of a male person and a genital area of a female person immediately before, during and immediately after sexual intercourse said barrier device comprising:

a. a tubular membrane open at a first end and closed at a second end, said membrane adapted to be interposed between a penis of said male person and the vagina of said female person when said penis is inserted in said vagina;

b. a means for exerting lateral compressive pressure on said penis and on said vagina;

c. means for seating the barrier device on a labia major of said female person, in said vagina, said device for inserting comprising a telescoping handle and a fibrous element attached to said telescoping handle.

90. A method for inserting a device for acting as a barrier between a genital area of a male person and a genital area of a female person immediately before, during and immediately after sexual intercourse, said barrier device comprising:

a. a tubular membrane open at a first end and closed at a second end, said membrane adapted to be interposed between a penis of said male person and the vagina of said female person when said penis is inserted in said vagina;

b. a means for exerting lateral compressive pressure on said penis and on said vagina;

c. means for seating the barrier device on a labia major of said female person, in said vagina, said method comprising the steps of:
- (i) providing a device for inserting said barrier device comprising a telescoping handle and a fibrous element attached to said telescoping handle;
- (ii) extending said telescoping handle to a desired length,
- (iii) locating a vaginal orifice of said female person;
- (iv) placing said closed end of said tubular membrane over the vaginal orifice, said means for seating being located over a labia majora of said female person;
- (v) placing said fibrous element in contact with said closed end; and
- (vi) advancing said telescoping handle to insert said closed end through said vaginal orifice and as far as desired into said vagina, subject to said length of said telescoping handle, thereby extending said tubular membrane into the vagina.

91. A method for inserting a device for acting as a barrier between a genital area of a male person and a genital area of a female person immediately before, during and immediately after sexual intercourse, said barrier device comprising:
- a. a tubular membrane open at a first end and closed at a second end, said membrane adapted to be interposed between a penis of said male person and the vagina of said female person when said penis is inserted in said vagina;
- b. a means for exerting lateral compressive pressure on said penis and on said vagina;
- c. means for seating the barrier device on a labia major of said female person, using a device for inserting said barrier device in said vagina, said method comprising the steps of:
    - (i) providing an insertion device comprising a means for expanding when filled with an expansive substance and a source of said expansive substance attached to said means for expanding, said source possessing a valve adapted to control a release of said expansive substance;
    - (ii) locating a vaginal orifice of said female person;
    - (iii) placing said closed end of said tubular membrane over said vaginal orifice, said means for seating being located over a labia majora of said female person;
    - (iv) placing a first end of said means for expanding in contact with said closed end of said tubular membrane, said first end being opposite to a second end of said means for expanding, said second end being attached to said source of said expansive substance; and
    - (v) expanding said means for expanding by manipulating said valve, thereby pressing said closed end of said tubular membrane through said vaginal orifice and as far as desired into said vagina, thereby extending said tubular membrane into said vagina as far as desired.

92. A device for packaging a barrier device for acting as a barrier between a genital area of a male person and a genital area of a female person immediately before, during and immediately after sexual intercourse, said barrier device comprising;
- a. a tubular membrane open at a first end and closed at a second end, said membrane adapted to be interposed between a penis of said male person and the vagina of said female person when said penis is inserted in said vagina;
- b. a means for exerting lateral compressive pressure on said penis and on said vagina;
- c. means for seating the barrier device on a labia major of said female person, said packaging device comprising a container possessing indicia, wherein said indicia are luminescent under visible light and retain their luminescence for a time in darkness.

93. The device for packaging of claim 92, further comprising perforations to facilitate the folding of said packaging and the extraction of said barrier device.

94. A method for inserting said barrier device in said vagina using said device for packaging of claim 93, said method comprising the steps of:
- a. folding said packaging and rupturing a first set of said perforations to form a configuration of said device for packaging adapted to support said device for packaging at a distance from said genital area of said female person when said device for packaging is attached to said genital area;
- b. locating said device for acting as a barrier over a vaginal orifice of said female person by using said indicia;
- c. removably attaching said device for packaging to said genital area;
- d. placing a device for inserting in said vagina said device for acting as a barrier in said vagina in contact with a location on said packaging indicated by said indicia;
- e. advancing said device for inserting so as to rupture a second set of said perforations and bring said device for inserting into contact with said closed end of said tubular membrane;
- f. further advancing said device for inserting so as to push said means for acting as a barrier through said device for packaging, thereby rupturing a third set of said perforations; and
- g. further advancing said device for inserting so as to insert said closed end of said tubular membrane through said vaginal orifice and as far as desired into said vagina, thereby extending said tubular membrane into said vagina as far as desired.

95. A device for acting as a barrier between a genital area of a male person and a genital area of a female person immediately before, during and immediately after sexual intercourse, said barrier device comprising:
- a. a tubular membrane open at a first end and closed at a second end, said membrane adapted to be interposed between a penis of said male person and the vagina of said female person when said penis is inserted in said vagina;
- b. a means for exerting lateral compressive pressure on said penis and on said vagina, wherein said tubular membrane has a substantially triangular cross-section, said cross-section being taken perpendicularly to a central axis of said tubular membrane.

96. A device for acting as a barrier between a genital area of a male person and a genital area of a female person immediately before, during and immediately after sexual intercourse, said barrier device comprising;
- a. a tubular membrane open at a first end and closed at a second end, said membrane adapted to be interposed between a penis of said male person and the vagina of said female person when said penis is inserted in said vagina;
- b. a means for exerting lateral compressive pressure on said penis and on said vagina, wherein said means for exerting lateral pressure comprises at least one microtubule of varying thickness along a perimeter of said at least one microtubule.

97. A device for acting as a barrier between a genital area of a male person and a genital area of a female person immediately before, during and immediately after sexual intercourse, said barrier device comprising:
   a. a tubular membrane open at a first end and closed at a second end, said membrane adapted to be interposed between a penis of said male person and the vagina of said female person when said penis is inserted in said vagina;
   b. a means for exerting lateral compressive pressure on said penis and on said vagina wherein said means for exerting lateral pressure comprises at least one microtubule and said at least one microtubule comprises at least one circumferential microtubule, and at least one of said at least one circumferential microtubule is located such that a wall of said at least one of said at least one circumferential microtubule protrudes from an interior surface of said tubular membrane.

98. A device for acting as a barrier between a genital area of a male person and a genital area of a female person immediately before, during and immediately after sexual intercourse, said barrier device comprising:
   a. a tubular membrane open at a first end and closed at a second end, said membrane adapted to be interposed between a penis of said male person and the vagina of said female person when said penis is inserted in said vagina;
   b. a means for exerting lateral compressive pressure on said penis and on said vagina, said means for extorting lateral pressure comprising at least one microtubule and said at least one microtubule comprises at least one longitudinal microtubule at least one of said at least one longitudinal microtubule is located such that a wall of said at least one of said at least one longitudinal microtubule protrudes from an interior surface of said tubular membrane.

99. A device for acting as a barrier between a genital area of a male person and a genital area of a female person immediately before, during and immediately after sexual intercourse, said barrier device comprising:
   a. a tubular membrane open at a first end and closed at a second end, said membrane adapted to be interposed between a penis of said male person and the vagina of said female person when said penis is inserted in said vagina;
   b. a means for exerting lateral compressive pressure on said penis and on said vagina said tubular membrane is adapted to be applied to the exterior of the skin of said penis, said lateral compressive pressure being exerted in at least one region to improve said male person's erection when said penis is in an erect state, said lateral compressive pressure being exerted without the application of shear stress to said tubular membrane, at least a portion of said means for exerting lateral compressive pressure being irremovably joined with said tubular membrane wherein said tubular membrane has a substantially triangular cross-section, said cross-section being taken perpendicularly to a central axis of said tubular membrane.

100. A device for acting as a barrier between a genital area of a male person and a genital area of a female person immediately before, during and immediately after sexual intercourse, said barrier device comprising:
   a. a tubular membrane open at a first end and closed at a second end, said membrane adapted to be interposed between a penis of said male person and the vagina of said female person when said penis is inserted in said vagina;
   b. a means for exerting lateral compressive pressure on said penis and on said vagina;
   c. means for seating the barrier device on a labia major of said female person, said tubular membrane adapted to be applied to the exterior of the skin of said penis, said lateral compressive pressure being exerted in at least one region to improve said male person's erection when said penis is is an erect state, said lateral compressive pressure being exerted without the application of shear stress to said tubular membrane, at least a portion of said means for exerting lateral compressive pressure being irremovably joined with said tubular membrane, wherein said means for seating comprises a lip attached to said first end of said tubular membrane, said lip being of varying radial dimension and possessing at least two protrusion on an outer periphery of said lip.

101. A device for exerting lateral compressive pressure on a penis of a male person and on a vagina of a female person, said lateral compressive pressure being exerted when said penis is inserted into said vagina, said device being adapted to be removably attached to a tubular membrane open at a first end and closed at a second end adapted to be interposed between said penis and said vagina when said penis is inserted into said vagina, said device for exerting lateral compressive pressure comprising a sheet adapted to be removably attached to said tubular membrane and adapted to be removably attached at its opposite longitudinal edges to form a cylinder, and further comprising at least one microtubule, wherein said at least one microtubule comprises at least one circumferential microtubule, said at least one circumferential microtubule is located such that a wall of said at least one of said at least one circumferential microtubule protrudes from an interior surface of said tubular membrane.

102. A device for exerting lateral compressive pressure on a penis of a male person and on a vagina of a female person, said lateral compressive pressure being exerted when said penis is inserted into said vagina, said device being adapted to be removably attached to a tubular membrane open at a first end and closed at a second end adapted to be interposed between said penis and said vagina when said penis is inserted into said vagina, said device for exerting lateral compressive pressure comprising a sheet adapted to be removably attached to said tubular membrane and adapted to be removably attached at its opposite longitudinal edges to form a cylinder, and further comprising at least one microtubule, said at least one microtubule comprises at least one longitudinal microtubule, wherein at least one of said at least one longitudinal microtubule is located such that a wall of said at least one of said at least one longitudinal microtubule protrudes from an interior surface of said tubular membrane.

103. A device for exerting lateral compressive pressure on a penis of a male person and on a vagina of a female person, said lateral compressive pressure being exerted when said penis is inserted into said vagina, said means being adapted to be removably attached to a tubular membrane open at a first end and closed at a second end adapted to be applied to the exterior of the skin of said penis, said means for exerting lateral compressive pressure comprises a sheet adapted to be removably attached to said tubular membrane and adapted to be removably attached at its opposite longitudinal edges to form a cylinder, said means for exerting lateral compressive pressure further comprises at least one microtubule, said at least one microtubule comprises at least one circumferential microtubule, wherein at least one of said at least one circumferential microtubule is located such that a wall of said at least one of said at least one circumferential microtubule protrudes from an interior surface of said tubular membrane.

104. A device for exerting lateral compressive pressure on a penis of a male person and on a vagina of a female person, said lateral compressive pressure being exerted when said penis is inserted into said vagina, said means being adapted to be removably attached to a tubular membrane open at a first end and closed at a second end adapted to be applied to the exterior of the skin of said penis, said means for exerting lateral compressive pressure comprises a sheet adapted to be removably attached to said tubular membrane and adapted to be removably attached at its opposite longitudinal edges to form a cylinder, said means further comprising at least one microtubule, said at least one microtubule comprises at least one longitudinal microtubule, wherein at least one of said at least one longitudinal microtubule is located such that a wall of said at least one of said at least one longitudinal microtubule protrudes from an interior surface of said tubular membrane.

105. A device for enclosing a user's penis, said means comprising:
  a. a tubular membrane open at a first end and closed at a second end, said tubular membrane adapted to be applied to the exterior of the skin of the user's penis; and
  b. means for expansion to simulate an erection of said user's penis, at least a portion of said means for expansion being irremovably joined with said tubular membrane, said expansion being produced without the use of any shear stress applied to said tubular membrane as a result of sexual intercourse, at least atmospheric pressure being maintained on said exterior of the skin of the user's penis while said tubular membrane is applied to said exterior of the skin of the user's penis, said means for expansion comprising at least one microtubule, said at least one microtubule comprises at least one circumferential microtubule, wherein at least one of said at least one circumferential microtubule is located such that a wall of said at least one of said at least one circumferential microtubule protrudes from an interior surface of said tubular membrane.

106. A device for enclosing a user's penis, said means comprising:
  a. a tubular membrane open at a first end and closed at a second end, said tubular membrane adapted to be applied to the exterior of the skin of the user's penis; and
  b. means for expansion to simulate an erection of said user's penis, at least a portion of said means for expansion being irremovably joined with said tubular membrane, said expansion being produced without the use of any shear stress applied to said tubular membrane as a result of sexual intercourse, at least atmospheric pressure being maintained on said exterior of the skin of the user's penis while said tubular membrane is applied to said exterior of the skin of the user's penis, said means for expansion comprising at least one microtubule, at least one microtubule comprising at least one longitudinal microtubule, wherein at least one of said at least one longitudinal microtubule is located such that a wall of said at least one of said at least one longitudinal microtubule protrudes from an interior surface of said tubular membrane.

* * * * *